United States Patent
Takimiya et al.

(10) Patent No.: US 9,018,630 B2
(45) Date of Patent: Apr. 28, 2015

(54) HETEROCYCLIC DINAPHTHO THIENO THIOPHENE (DNTT) COMPOUNDS FOR USE AS ORGANIC SEMICONDUCTOR THIN FILMS IN FIELD EFFECT TRANSISTORS AND RELATED METHODS

(75) Inventors: Kazuo Takimiya, Higashihiroshima (JP); Kazuki Niimi, Higashihiroshima (JP); Hirokazu Kuwabara, Tokyo (JP); Yuichi Sadamitsu, Tokyo (JP); Eisei Kanoh, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/000,440

(22) PCT Filed: Feb. 24, 2012

(86) PCT No.: PCT/JP2012/054604
§ 371 (c)(1),
(2), (4) Date: Aug. 20, 2013

(87) PCT Pub. No.: WO2012/115236
PCT Pub. Date: Aug. 30, 2012

(65) Prior Publication Data
US 2013/0330876 A1    Dec. 12, 2013

(30) Foreign Application Priority Data

Feb. 25, 2011 (JP) .................................. 2011-039403

(51) Int. Cl.
*H01L 51/05* (2006.01)
*H01L 51/40* (2006.01)
(Continued)

(52) U.S. Cl.
CPC .......... *H01L 51/0074* (2013.01); *C07C 319/20* (2013.01); *C07D 495/04* (2013.01);
(Continued)

(58) Field of Classification Search
USPC ......................................................... 568/52
See application file for complete search history.

(56) References Cited

U.S. PATENT DOCUMENTS

2006/0052612 A1    3/2006 Stossel et al.
2009/0043113 A1    2/2009 Park et al.
(Continued)

FOREIGN PATENT DOCUMENTS

CN    1671675 A    9/2005
CN    101528753 A    9/2009
(Continued)

OTHER PUBLICATIONS
International Search Report and Written Opinion mailed Mar. 27, 2012 in corresponding PCT application No. PCT/JP2012/054604.
(Continued)

*Primary Examiner* — Stephen W Smoot
(74) *Attorney, Agent, or Firm* — Nields, Lemack & Frame, LLC

(57) ABSTRACT

Provided are a novel heterocyclic compound represented by formula (1), and a field-effect transistor having a semiconductor layer comprising the aforementioned compound. Also provided is a method for producing an intermediate enabling the production of the aforementioned novel heterocyclic compound. (In the formula, $R^1$ and $R^2$ represent a hydrogen atom, a $C_{2-16}$ alkyl group or an aryl group. However, when $R^1$ each independently represents a $C_{2-16}$ alkyl group or an aryl group, $R^2$ represents a hydrogen atom or each independently represents an aryl group; and when $R^1$ represents a hydrogen atom, $R^2$ each independently represents an aryl group.)

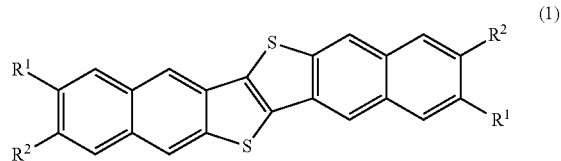

(1)

18 Claims, 3 Drawing Sheets

(51) Int. Cl.
*C07D 495/04* (2006.01)
*H01L 51/00* (2006.01)
*C07C 319/20* (2006.01)
*C09K 11/06* (2006.01)

(52) U.S. Cl.
CPC ............ *C09K 11/06* (2013.01); *H01L 51/0558* (2013.01); *C09K 2211/1011* (2013.01); *C09K 2211/1092* (2013.01)

(56) References Cited

U.S. PATENT DOCUMENTS

| | | |
|---|---|---|
| 2010/0032655 A1 | 2/2010 | Takimiya et al. |
| 2010/0065826 A1 | 3/2010 | Takimiya et al. |
| 2011/0303910 A1 | 12/2011 | Kuwabara et al. |

FOREIGN PATENT DOCUMENTS

| | | |
|---|---|---|
| CN | 101529609 B | 10/2010 |
| EP | 1138328 A1 | 10/2001 |
| EP | 1847544 A1 | 10/2007 |
| EP | 2077590 A1 | 7/2009 |
| EP | 2098527 A1 | 9/2009 |
| JP | 6-177380 A | 6/1994 |
| JP | 2001-94107 A | 4/2001 |
| JP | 2008-10541 A | 1/2008 |
| JP | 2009-152355 A | 7/2009 |
| JP | 2009-196975 A | 9/2009 |
| JP | 2010-258214 A | 11/2010 |
| KR | 10-2008-0100982 A | 11/2008 |
| WO | 2006/077888 A1 | 7/2006 |
| WO | 2008/047896 A1 | 4/2008 |
| WO | 2008/050726 A1 | 5/2008 |
| WO | 2009/009790 A1 | 1/2009 |
| WO | 2010/098372 A1 | 9/2010 |

OTHER PUBLICATIONS

International Preliminary Report on Patentability mailed Sep. 6, 2013 in corresponding PCT application No. PCT/JP2012/054604.
J. Am. Chem. Soc., 2007, vol. 129, pp. 2224-2225, "Facile Synthesis of Highly Pi-Extended Heteroarenes, Dinaphtho [2,3-b:2',3'-f]chalcogeneopheno[3,2-b]chalcogenophenes, and Their Application to Field-Effect Transistors", Yamamoto, et al.
Tetrahedron Letters, 1988, vol. 29, No. 23, pp. 2783-2786, "Palladium(0) Catalyzed Coupling of trans-1,2-Bis(tri-n-butylstannyl)ethylene with Aromatic Halides: A Convenient Synthesis of Substituted trans-B-Bromostyrenes", Haack, et al.
Eur. J. Org. Chem., 2002, No. 2, pp. 319-326, "Developments in the Simmons-Smith-Mediated Epoxidation Reaction", Aggarwal, et al.
European communication dated Jun. 16, 2014 in corresponding European patent application No. EP 12750215.1.
Advanced Materials, 2011, vol. 23, No. 14, published online Feb. 10, 2011, XP 55121933, pp. 1626-1629, "Patternable Solution-Crystallized Organic Transistors with High Charge Carrier Mobility", Nakayama, et al.
Advanced Materials, 2011, vol. 23, No. 10, published online Aug. 20, 2010, XP 55121923, pp. 1222-1225, "Alkylated Dinaphtho[2,3-b:2',3'-f]Thieno[3,2-b]Thiophenes (Cn-DNTTs): Organic Semiconductors for High-Performance Thin-Film Transistors", Kang, et al.
Chemical Science, 2010, vol. 1, No. 2, Accepted Mar. 26, 2010, published May 20, 2010, XP 55121919, pp. 179-183, "Unique three-dimensional (3D) molecular array in dimethyl-DNTT crystals: a new approach to 3D organic semiconductors", Kang, et al.
Applied Physics Letters, American Institute of Physics, 2009, vol. 94, No. 10, published online Mar. 13, 2009, XP 012118363, pp. 103307-1-103307-3, "Three-dimensional organic field-effect transistors with high output current and high on-off ratio", Uno, et al.
Applied Physics Letters, American Institute of Physics, 2009, vol. 94, No. 22, published online Jun. 5, 2009, XP 012121523, pp. 223308-1-223308-3, "Moderately anisotropic field-effect mobility in dinaphtho[2,3-b:2',3'-f]thiopheno [3,2-b]thiophenes single-crystal transistors", Uno, et al.
English translation of Chinese communication, issued Aug. 8, 2014 in corresponding Chinese patent application No. CN 201280010570.8.
International Search Report mailed Apr. 13, 2010 in co-pending PCT application No. PCT/JP2010/052923.
English translation of Written Opinion mailed Apr. 13, 2010 in co-pending PCT application No. PCT/JP2010/052923.
English translation of International Preliminary Report on Patentability issued Sep. 13, 2011 in co-pending PCT application No. PCT/JP2010/052923.
European communication mailed May 18, 2012 in co-pending European patent application No. EP 10746251.7.
Chinese communication, with English translation, issued Apr. 22, 2013 in co-pending Chinese patent application No. CN 201080009791.4.
Japanese communication dated Nov. 13, 2013 in co-pending Japanese patent application No. JP 2011-501631.
Partial English translation of Japanese communication dated Nov. 13, 2013 in co-pending Japanese patent application No. JP 2011-501631.
Journal of the American Chemical Society, 2007, V. 129, No. 51, pp. 15732-15733, Highly Soluble [1]Benzothieno[3.2-b]benzothiophene (BTBT) Derivatives for High-Performance, Solution-Processed Organic Field-Effect Transistors, Ebata, et al.
Advanced Materials, 2008, vol. 20, No. 18, pp. 3388-3392, "Molecular Ordering of High-Performance Soluble Molecular Semiconductors and Re-evaluation of Their Field-Effect Transistor Characteristics", Izawa, et al.
Office Action mailed Nov. 6, 2012 in co-pending U.S. Appl. No. 13/203,494.
Final Rejection mailed Apr. 11, 2013 in co-pending U.S. Appl. No. 13/203,494.
Advisory Action mailed Jul. 26, 2013 in co-pending U.S. Appl. No. 13/203,494.
Office Action mailed Jan. 14, 2014 in co-pending U.S. Appl. No. 13/203,494.
Final Rejection mailed Sep. 9, 2014 in co-pending U.S. Appl. No. 13/203,494.
Office Action mailed Feb. 9, 2015 in co-pending U.S. Appl. No. 13/203,494.

A

B

C

D

E

HETEROCYCLIC DINAPHTHO THIENO THIOPHENE (DNTT) COMPOUNDS FOR USE AS ORGANIC SEMICONDUCTOR THIN FILMS IN FIELD EFFECT TRANSISTORS AND RELATED METHODS

TECHNICAL FIELD

The present invention relates to a novel heterocyclic compound, a novel method for producing an intermediate enabling synthesis of the compound, and use of the compound. More specifically, the present invention relates to a novel [1]benzothieno[3,2-b][1]benzothiophene derivative usable as an organic semiconductor or the like, and an effective method for producing an intermediate enabling synthesis of the derivative. The present invention also relates to a field effect transistor using the compound.

BACKGROUND ART

The field effect transistor is typically an element having a semiconductor layer (semiconductor film), a source electrode, a drain electrode, and a gate electrode for each of these electrodes provided with an insulator layer being interposed therebetween, and the like on a substrate. The field effect transistor is used as a logic circuit element in integrated circuits, and widely used as a switching element and the like. The semiconductor layer is typically formed of a semiconductor material. The field effect transistor at present is formed using an inorganic semiconductor material, which is mainly silicon. A thin film transistor having a semiconductor layer created on a substrate such as glass using amorphous silicon in particular is used for displays or the like. In use of such an inorganic semiconductor material, the workpiece needs to be treated at a high temperature or in vacuum during production of the field effect transistor. Therefore, large investment in facility and a large amount of energy during production are necessary, leading to very high production cost. Moreover, because these components are exposed to a high temperature during production of the field effect transistor, a material having insufficient heat resistance such as films and plastics is difficult to use as the substrate. A flexible material that can be bent, for example, is difficult to use as the substrate. Thus, the application area of the field effect transistor is limited.

Meanwhile, field effect transistors using an organic semiconductor material have been studied and developed actively. Use of the organic material can eliminate the treatment at a high temperature, and allow the process at a low temperature, leading to variety of substrate materials that can be used.

As a result, recently, a field effect transistor more flexible, lighter, and more difficult to break than the conventional field effect transistor has been able to be created. In a step of creating the field effect transistor, a method such as application of a solution prepared by dissolving a semiconductor material and printing of the solution by inkjet may be used, and can produce a field effect transistor having a large area at low cost. A variety of compounds for the organic semiconductor material can be selected, and utilization of the properties of the compound and development of the functions that do not exist before are expected.

As an example in which an organic compound is used as the semiconductor material, a variety of organic compounds have been studied. For example, organic materials using pentacene, thiophene, or an oligomer or polymer thereof are already known as a material having hole transport properties (see Patent Literature 1 and Patent Literature 2). Pentacene is an acene aromatic hydrocarbon including 5 benzene rings linearly condensed. It is reported that the field effect transistor using pentacene as the semiconductor material exhibits mobility of charges (carrier mobility) equal to that of amorphous silicon that is used in practice. The field effect transistor using pentacene, however, deteriorates due to an environment, and has problems with stability. The field effect transistor using a thiophene compound also has the same problems, and it is hard to say that these materials have high practicality. Dinaphtho[2,3-b:2',3'-f]thieno[3,2-b]thiophene (DNTT) being stable in the air and having high carrier mobility has been developed recently, and received attention (see Patent Literature 3 and Non Patent Literature 1). Unfortunately, even these compounds need to have higher carrier mobility for use in applications of displays such as organic ELs. Development of a high quality and high performance organic semiconductor material is demanded from the viewpoint of durability.

Citation list on a DNTT derivative having a substituent includes Patent Literatures 3, 4, and 5. Specific examples of the substituent include a methyl group, a hexyl group, an alkoxyl group, and a substituted ethynyl group. The substituents in the DNTT derivative described as Examples are only a methyl group and a substituted ethynyl group. These groups exhibit only semiconductor properties equal to or less than those of DNTT having no substituent.

Later, Patent Literature 6 describes dinaphtho[2,3-b:2',3'-f]thieno[3,2-b]thiophene in Formula 1 (Alkyl DNTT, wherein Alkyl represents a C5 to C16 alkyl group) wherein dinaphtho[2,3-b:2',3'-f]thieno[3,2-b]thiophene has properties more excellent than those of the conventional organic semiconductor material in the respect above. Patent Literature 6 shows that the field effect transistor element using this compound is not influenced by the states of the substrate and insulation film during creation of the element (or irrespective of whether a substrate is treated or not), and has extremely improved semiconductor properties; and that the effect is remarkably enhanced by performing a heat treatment during creation of the element.

Formula 1

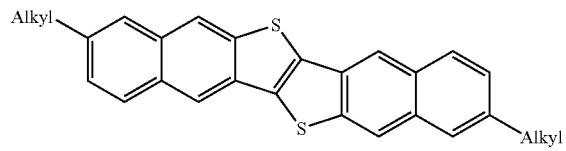

As described above, these DNTT derivatives useful for the organic semiconductors have been developed, but the conventional production methods have limitation in a method for constructing particularly a thienothiophene structure portion. Namely, a DNTT having a substituent selectively in a position other than the 2,9-positions is difficult to produce, leading to delay of development of a derivative of DNTT. The following three methods of producing a DNTT derivative are mainly known. These will be described below.

The first method is a method in which a derivative is constructed using a starting material tetrabromothienothiophene having a thienothiophene structure from the beginning (Patent Literature 5). In this production method, unsubstituted benzaldehyde causes no problem, but the method has a disadvantage in which use of benzaldehyde having a substituent produces a mixture of DNTT derivatives having substituents at various positions.

Reaction formula 1

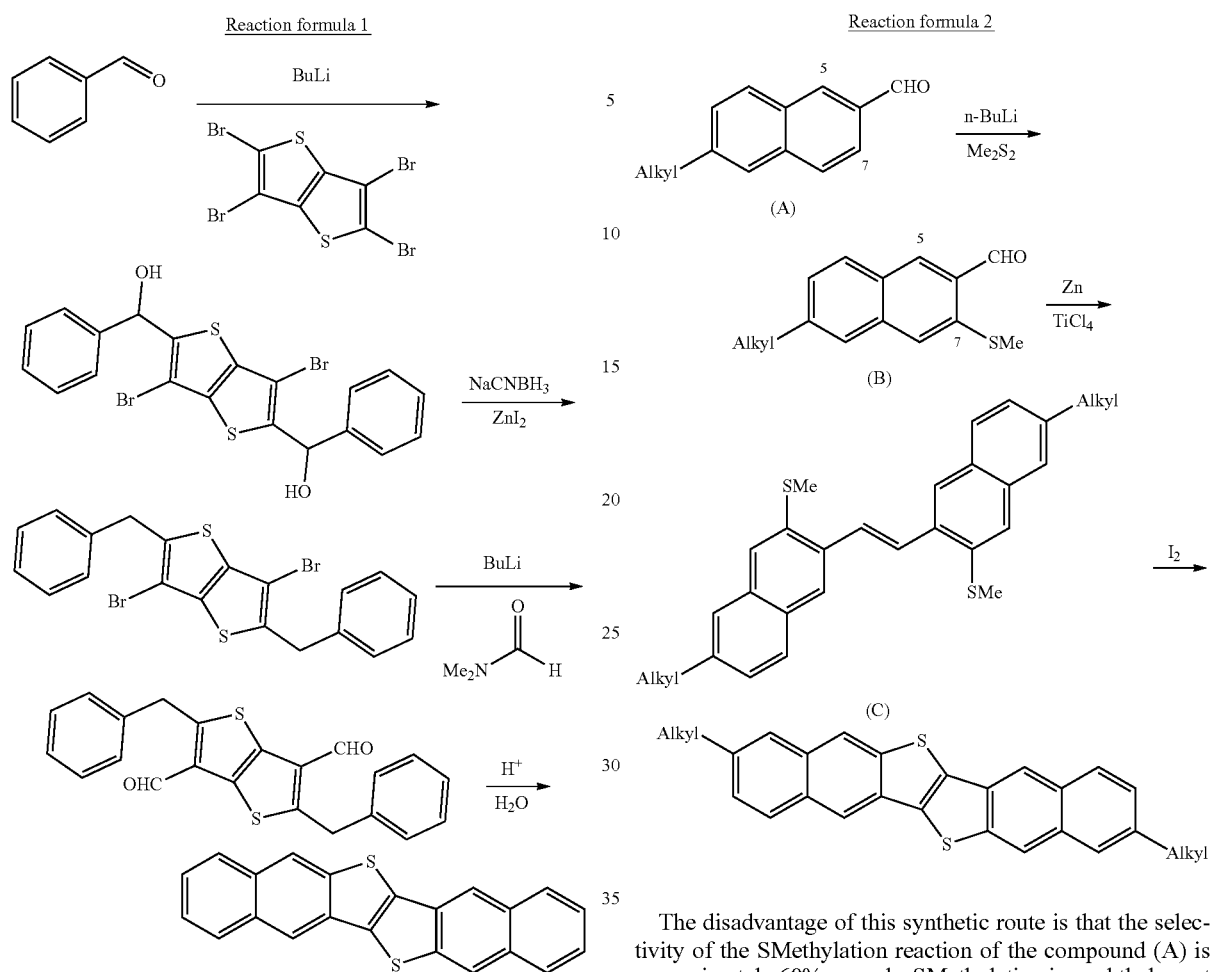

Reaction formula 2

The second method is a method of producing a derivative from an ethylene derivative. Most of DNTT derivatives have been synthesized by this method (Non Patent Literature 1, Patent Literature 3, Patent Literature 6, Patent Literature 7, and Patent Literature 8).

For example, Patent Literature 6 discloses that according to the known methods disclosed in Patent Literature 3 and Non Patent Literature 1,2-alkyl-7-methylthio-6-naphthoaldehyde (B) is obtained from 2-alkyl-6-naphthoaldehyde (A), and condensed to obtain 1,2-bis(2-alkyl-7-methylthio-6-naphthyl)ethylene (C). Patent Literature 6 also discloses that 1,2-bis(2-alkyl-7-methylthio-6-naphthyl)ethylene (C) can be further ring closed to obtain a target compound 2,9-dialkyldinaphtho[2,3-b:2',3'-f]thieno[3,2-b]thiophene (2,9-dialkyl DNTT).

Namely, in Patent Literature 6, the compound (B) is obtained by reacting dimethyl sulfide with the compound (A), and the condensate (C) is obtained by McMurry coupling. Further, the target DNTT derivative is obtained by making a ring close reaction in chloroform using the condensate (C) and iodine. Unlike the above first method, the second method is a production method that can produce only a DNTT derivative having a substituent in the target position.

The disadvantage of this synthetic route is that the selectivity of the SMethylation reaction of the compound (A) is approximately 60%, namely, SMethylation in naphthalene at the 7-position as desired occurs only approximately 60%. In approximately 30% of the compound (A), SMethylation undesirably occurs at the 5-position, and approximately 10% of the raw material is recovered. As a result, the compound (B) is extremely difficult to separate and refine.

From above, this method has disadvantages in that the Alkyl-substituted compound (B) cannot be separated by recrystallization that is a method at industrially low cost or the like, needs to be subjected to column refining using an adsorbent (such as silica gel) accompanied by large investment in facility, and cannot be produced at low cost. When the substituent is an aryl group, the separation and the production are more difficult. Additionally, the reaction shown in the reaction formula (2) cannot produce the DNTT having a substituent at 3,10-positions because of limitation in the raw material. This method has such problems, but the method using the compound (B) as the raw material have to be selected in the related art to generate the compound (C) efficiently.

As above, the compound (C) is important in development of the DNTT derivative, but difficulties in synthesis and separation of the compound (B) as the raw material for the DNTT derivative at industrially low cost are known. These difficulties lead to delay of development of the DNTT having a substituent. For this reason, it is easily presumed that if development of an intermediate compound for producing the compound (C) progresses, following this, development of a derivative of the DNTT having a substituent significantly progresses. Development of such a method for producing an intermediate has been required.

The third method is a typical synthesis method using an acetylene derivative (E) (Patent Literature 7). In this synthetic method, it cannot be said yet that an industrial method for producing a Br body (D) as a raw material is established, and a problem of the method is the difficulties in synthesis of an acetylene derivative (E) (Patent Literature 7, Patent Literature 9). Another problem of the method is that cyclization reaction of an acetylene derivative with iodine usually has a low yield (in Patent Literature 7, a yield of approximately 10% to 40%).

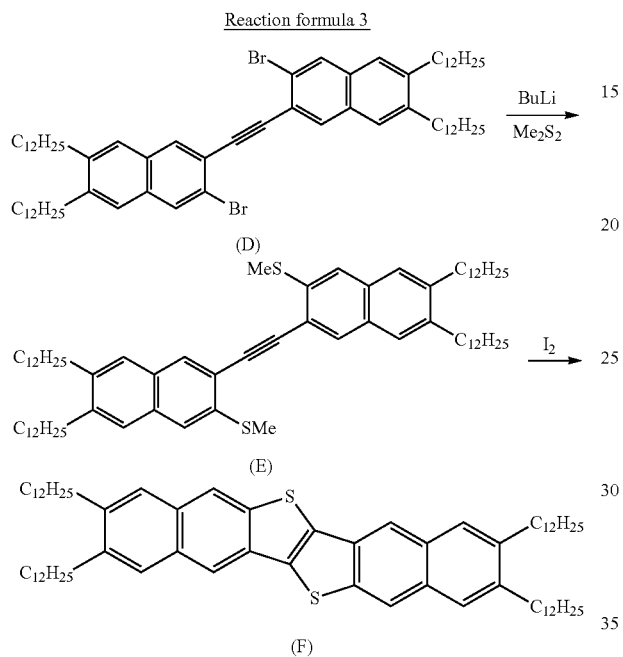

Reaction formula 3

CITATION LIST

Patent Literature

[Patent Literature 1] JP 2001-94107 A
[Patent Literature 2] JP 06-177380 A
[Patent Literature 3] WO2008/050726
[Patent Literature 4] JP 2008-10541 A
[Patent Literature 5] KR2008100982
[Patent Literature 6] WO2010/098372
[Patent Literature 7] JP 2009-196975 A
[Patent Literature 8] WO2009/009790
[Patent Literature 9] JP 2010-258214 A

Non Patent Literature

[Non Patent Literature 1] J. Am. Chem. Soc., Vol. 129, 2224-2225 (2007)

SUMMARY OF INVENTION

Technical Problem

An object of the present invention is to provide a novel heterocyclic compound exhibiting high carrier mobility and having practical properties as a semiconductor, a novel method for producing an intermediate enabling synthesis of the compound, a semiconductor material comprising the compound, and a field effect transistor having an organic semiconductor thin film formed of the compound, and a production method therefor.

Solution to Problem

As result of an extensive research to solve the problems above, the present inventors succeeded in development of a novel heterocyclic compound and a novel method for producing an intermediate enabling synthesis of the compound. The present inventors found out that the novel heterocyclic compound exhibits high carrier mobility and has practical properties as a semiconductor, and can provide a semiconductor material comprising the compound, a field effect transistor having an organic semiconductor thin film formed of the compound, and a production method therefor. Thus, the present invention has been completed.

Namely, one aspect of the present invention relates to:

[1] A heterocyclic compound represented by the following formula (1):

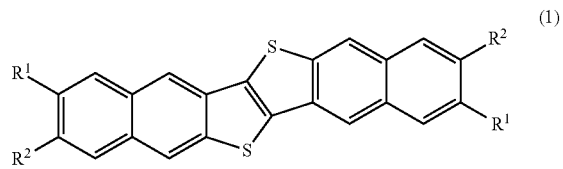

(wherein $R^1$ and $R^2$ each represent one of a hydrogen atom, a C2-C16 alkyl group, and an aryl group; when $R^1$ each independently represents a C2-C16 alkyl group or an aryl group, $R^2$ each represents a hydrogen atom or $R^2$ each independently represents an aryl group; and when $R^1$ represents a hydrogen atom, $R^2$ each independently represents an aryl group).

[2] The heterocyclic compound according to [1], wherein in the formula (1), $R^1$ each independently is a linear C5-C12 alkyl group, and $R^2$ each is a hydrogen atom.

[3] The heterocyclic compound according to [1], wherein in the formula (1), $R^1$ each independently is an aryl group having one of a phenyl structure, a naphthyl structure, and a biphenyl structure, and $R^2$ each is a hydrogen atom.

[4] The heterocyclic compound according to [1], wherein in the formula (1), $R^1$ is a hydrogen atom, and $R^2$ each independently is an aryl group having one of a phenyl structure, a naphthyl structure, and a biphenyl structure.

[5] The heterocyclic compound according to [3], wherein in the formula (1), $R^1$ each independently is an aryl group selected from the group consisting of a phenyl group, a 4-alkylphenyl group, a 1-naphthyl group, and a biphenyl group, and $R^2$ is a hydrogen atom.

[6] The heterocyclic compound according to [4], wherein in the formula (1), $R^1$ each is a hydrogen atom, and $R^2$ each independently is an aryl group selected from the group consisting of a phenyl group, a 4-alkylphenyl group, a 1-naphthyl group, and a biphenyl group.

[7] A method for producing an intermediate compound represented by a formula (4) in production of a heterocyclic compound represented by a formula (2), the method comprising reacting a compound represented by a formula (3) with dimethyl disulfide:

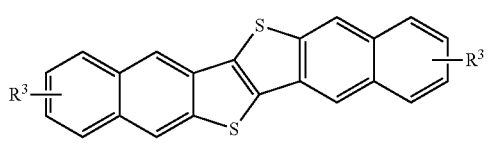

(2)

(wherein R³ represents a substituent);

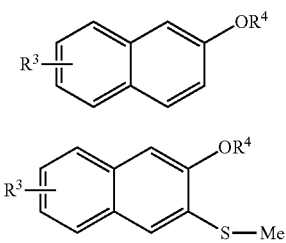

(wherein R³ and R⁴ represent a substituent).

[8] A method for producing an intermediate compound represented by a formula (6) in production of a heterocyclic compound represented by a formula (2), the method comprising reacting a compound represented by a formula (4) with a tin compound represented by a formula (5):

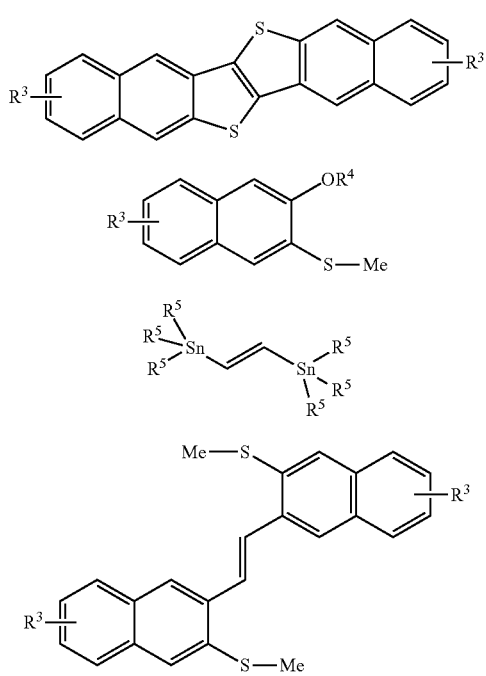

(wherein R³, R⁴, and R⁵ represent a substituent).

[9] An organic semiconductor material comprising one or two or more heterocyclic compounds represented by the formula (1) according to any one of [1] to [6].

[10] An ink for creating a semiconductor device, comprising one or two or more heterocyclic compounds represented by the formula (1) according to any one of [1] to [6].

[11] An organic thin film comprising one or two or more heterocyclic compounds represented by the formula (1) according to any one of [1] to [6].

[12] A method for producing an organic thin film, wherein the organic thin film according to [11] is formed by a deposition method.

[13] A method for producing an organic thin film, wherein the organic thin film according to [11] is formed by applying the ink for creating a semiconductor device according to [10].

[14] A field effect transistor comprising an organic thin film according to [11].

[15] The field effect transistor according to [14], wherein the field effect transistor is a bottom contact type.

[16] The field effect transistor according to [14], wherein the field effect transistor is a top contact type.

[17] A method for producing a field effect transistor, comprising the step of forming an organic thin film on a substrate by the method according to [12] or [13], the organic thin film comprising one or two or more heterocyclic compounds represented by the formula (1) according to any one of [1] to [6].

Advantageous Effects of Invention

A field effect transistor including an organic thin film comprising the novel heterocyclic compound represented by the formula (1) as a semiconductor layer can provide a field effect transistor having more excellent semiconductor properties such as carrier mobility and durability than those of the transistor including an organic thin film comprising the conventional organic semiconductor material. Further, the novel method for producing a key intermediate enabling production of these compounds in industrial scale is a reaction having high selectivity. This novel method also can produce the DNTT having an aryl group at the 2,9-positions and DNTT having a substituent at the 3,10-positions that cannot be produced in the related art, and provide a production method that can be used in industrial scale.

DESCRIPTION OF EMBODIMENTS

Figure 1:
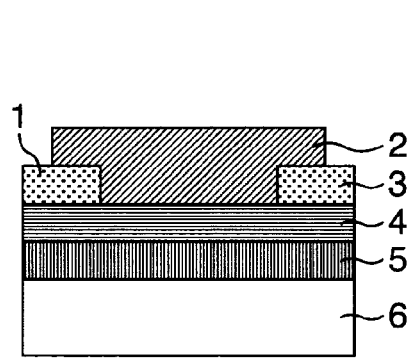
FIG. 1 is a schematic view showing one embodiment of a field effect transistor according to the present invention.
Figure 1:
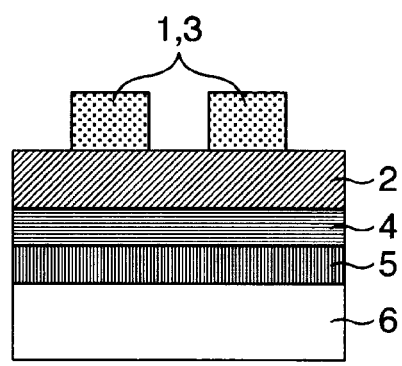
Figure 1:
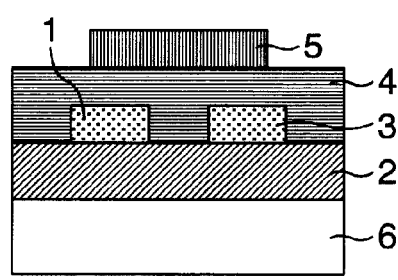
Figure 1:
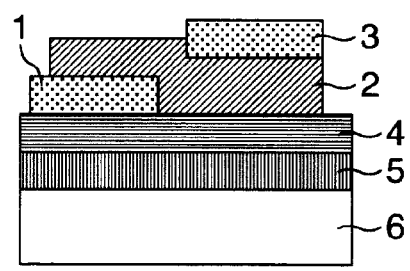
Figure 1:
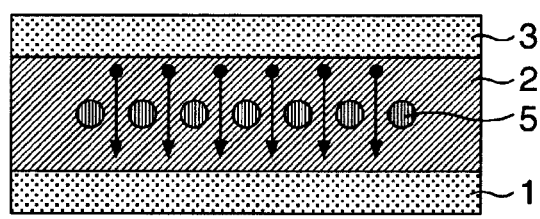

The present invention will be specifically described. The present invention relates to an organic field effect transistor using a specific organic compound as the semiconductor material. A compound represented by the formula (1) is used as the semiconductor material, and a semiconductor layer is formed of the compound. First, the compound represented by formula (1) will be described.

In the formula (1), R¹ and R² represent a hydrogen atom, a C2-C16 alkyl group, or an aryl group. When R¹ each independently represents a C2-C16 alkyl group or an aryl group, R² represents a hydrogen atom or R² represents each independently an aryl group. When $R^1$ is a hydrogen atom, $R^2$ each independently represents an aryl group.

Examples of the alkyl group for $R^1$ include linear, branched, or cyclic alkyl groups. The alkyl groups have carbon atoms usually 2 to 16, preferably 4 to 14, more preferably 6 to 12.

Here, specific examples of linear alkyl groups include ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, and n-hexadecyl.

Specific examples of branched alkyl groups include C3-C16 saturated branched alkyl groups such as i-propyl, i-butyl, i-pentyl, i-hexyl, and i-decyl.

Specific examples of cyclic alkyl groups include C5-C16 cycloalkyl groups such as cyclohexyl, cyclopentyl, adamantyl, and norbornyl.

The C2-C16 alkyl group is preferably saturated alkyl groups rather than unsaturated alkyl groups, and preferably has no substituent rather than has a substituent. Among these, C4-C14 saturated linear alkyl groups are preferable, C6-C12 saturated linear alkyl groups are more preferable, and an n-hexyl group, an n-octyl group, an n-decyl group, and an n-dodecyl group are still more preferable.

The aryl group for $R^1$ and $R^2$ represents an aromatic hydrocarbon group such as a phenyl group, a biphenyl group, a pyrene group, a 2-methylphenyl group, a 3-methylphenyl group, a 4-methylphenyl group, a 4-butylphenyl group, a 4-hexylphenyl group, a 4-octylphenyl group, a 4-decylphenyl group, a xylyl group, a mesityl group, a cumenyl group, a benzyl group, a phenylethyl group, an α-methylbenzyl group, a triphenylmethyl group, a styryl group, a cinnamyl group, a biphenylyl group, a 1-naphthyl group, a 2-naphthyl group, an anthryl group, and a phenanthryl group; and a heterocyclic group such as a 2-thienyl group. These groups may have substituent(s) which may be the same or different.

The aryl group is preferably an aryl group having a phenyl, naphthyl, or biphenyl structure, and more preferably a phenyl group, a 4-methylphenyl group, a 4-hexylphenyl group, a 4-octylphenyl group, a 4-decylphenyl group, a 1-naphthyl group, a 2-naphthyl group, and a biphenyl group.

When both of $R^1$ represent a C2-C16 alkyl group or an aryl group, $R^2$ is a hydrogen atom or $R^2$ each independently represents an aryl group. When $R^1$ is a hydrogen atom, $R^2$ each independently represents an aryl group. $R^1$ may be the same or different, and $R^2$ may be the same or different. More preferably, $R^1$ and $R^2$ each independently are the same. This means that preferably $R^1$ on the left side and $R^1$ on the right side are the same and $R^2$ on the left side and $R^2$ on the right side are the same, but $R^1$ and $R^2$ do not need to be the same.

The compound represented by the formula (1) can be synthesized by the method for producing a compound represented by the formula (2) described later.

The method for refining the compound represented by the formula (1) is not particularly limited, and a known method such as recrystallization, column chromatography, and vacuum sublimation refining can be used. These methods can be used in combination when necessary.

Specific examples of the compound represented by the formula (1) are shown in the Table 1. n indicates normal, i indicates iso, s indicates secondary, t indicates tertiary, and cy indicates cyclo. Ph indicates a phenyl group, Tolyl indicates a tolyl group, PhPh indicates a biphenyl group, Nap indicates a naphthyl group, and 2-thienyl indicates a 2-thiophene group. The blank indicates hydrogen.

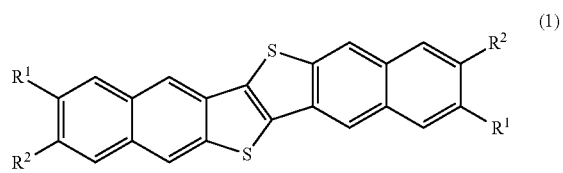

(1)

TABLE 1

| Compound No. | $R^1$ | $R^2$ |
|---|---|---|
| (1)-01 | Et | |
| (1)-02 | n-Pr | |
| (1)-03 | i-Pr | |
| (1)-04 | n-Bu | |
| (1)-05 | i-Bu | |
| (1)-06 | t-Bu | |
| (1)-07 | n-$C_5H_{11}$ | |
| (1)-08 | n-$C_6H_{13}$ | |
| (1)-09 | n-$C_7H_{15}$ | |
| (1)-10 | n-$C_8H_{17}$ | |
| (1)-11 | n-$C_9H_{19}$ | |
| (1)-12 | n-$C_{10}H_{21}$ | |
| (1)-13 | n-$C_{11}H_{23}$ | |
| (1)-14 | n-$C_{12}H_{25}$ | |
| (1)-15 | n-$C_{13}H_{27}$ | |
| (1)-16 | n-$C_{14}H_{29}$ | |
| (1)-17 | n-$C_{16}H_{33}$ | |
| (1)-18 | cy-$C_5H_9$ | |
| (1)-19 | cy-$C_6H_{11}$ | |
| (1)-20 | cy-$C_8H_{15}$ | |
| (1)-21 | cy-$C_{10}H_{19}$ | |
| (1)-22 | Ph | |
| (1)-23 | 4-Tolyl | |
| (1)-24 | PhPh | |
| (1)-25 | 1-Nap | |
| (1)-26 | 2-Nap | |
| (1)-27 | 2-thienyl | |
| (1)-28 | 4-HexylPh | |
| (1)-29 | 4-OctylPh | |
| (1)-30 | 4-DecylPh | |
| (1)-31 | | Ph |
| (1)-32 | | 4-Tolyl |
| (1)-33 | | PhPh |
| (1)-34 | | 1-Nap |
| (1)-35 | | 2-Nap |
| (1)-36 | | 2-thienyl |
| (1)-37 | | 4-HexylPh |
| (1)-38 | | 4-OctylPh |
| (1)-39 | | 4-DecylPh |
| (1)-40 | n-Bu | Ph |
| (1)-41 | n-$C_6H_{13}$ | Ph |
| (1)-42 | n-$C_8H_{17}$ | Ph |
| (1)-43 | n-$C_{10}H_{21}$ | Ph |
| (1)-44 | n-$C_{12}H_{25}$ | Ph |
| (1)-45 | Ph | Ph |
| (1)-46 | 4-Tolyl | Ph |
| (1)-47 | PhPh | Ph |
| (1)-48 | 1-Nap | Ph |
| (1)-49 | 2-thienyl | Ph |
| (1)-50 | Ph | 4-Tolyl |
| (1)-51 | Ph | PhPh |
| (1)-52 | n-$C_8H_{17}$ | n-$C_8H_{17}$ |
| (1)-53 | n-$C_{12}H_{25}$ | n-$C_{12}H_{25}$ |

Hereinafter, a method for producing the compound of the present invention will be specifically described. The method for producing the compound of the present invention is a novel production method. This production method enables production at a very high yield of not only the compound represented by the formula (1) that is a novel compound, but also a known DNTT such as a DNTT wherein $R^1$ is a hydrogen atom and $R^2$ is an alkyl group (e.g. (C2-C16) alkyl group).

The reaction formulas in the present invention are shown as follows. Hereinafter, reaction formulas (4), (5), and (6) will be described in order.

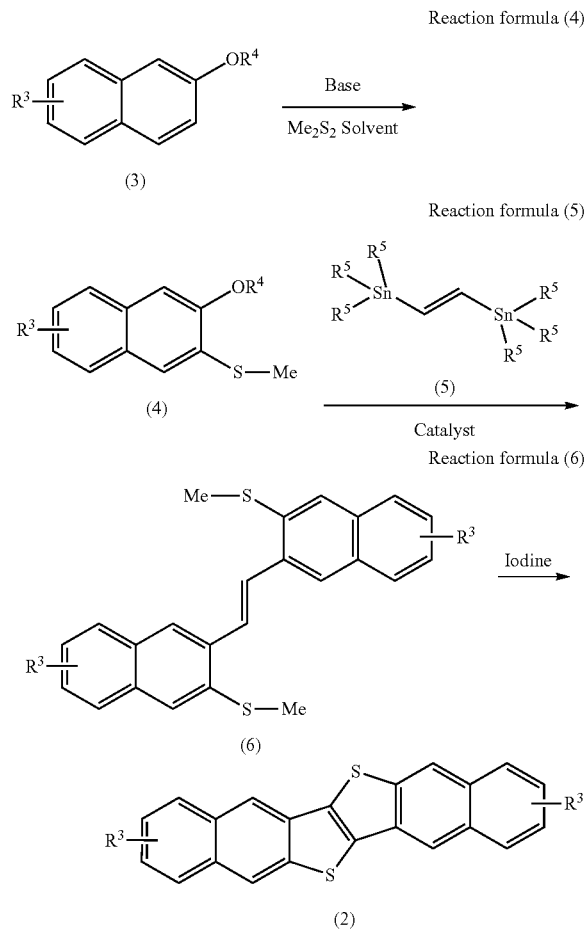

First, the compound (3) that is a starting material for the compound (2), and the compound (4) that is a product of the reaction formula (4) will be described.

In the compound (3) and the compound (4), $R^3$ represents a substituent. Examples of the substituent include a hydrogen atom, an alkyl group, an aryl group, an ether group, a thioether group, an ester group, an acyl group, an amino group, a cyano group, and a nitro group. These groups may have a substituent, and may be the same or different.

Here, the alkyl group for $R^3$ is a linear, branched, or cyclic C1 to C16 alkyl group. The aryl group means the same as the aryl group for $R^1$ and $R^2$ in the compound (1).

The ether group is an alkoxy group having an alkyl group having 1 to 16 carbon atoms and bonded to an oxygen atom, or an aryl group bonded to an oxygen atom (aryloxy group).

The thioether group is a thioalkoxy group having an alkyl group having 1 to 16 carbon atoms and bonded to a sulfur atom, or an aryl group bonded to a sulfur atom (arylthio group).

$R^3$ is preferably C1-C16 saturated linear alkyl groups, and aryl groups having a phenyl, naphthyl, or biphenyl structure. $R^3$ is more preferably C4-C14 saturated linear alkyl groups, a phenyl group, a 4-methylphenyl group, and a biphenyl group.

In the compound (3) and the compound (4), $R^4$ represents a hydrogen atom; an alkyl group; an aryl group; an alkyl $SO_2$ group; an aryl $SO_2$ group; and an alkyl group, aryl group, alkyl $SO_2$ group or aryl $SO_2$ group having one or more fluorine atoms which one or more hydrogen atoms have been substituted with.

Here, the alkyl group means the same as the alkyl group for $R^3$. The aryl group means the same as the aryl group for $R^1$ and $R^2$. The alkyl $SO_2$ group is an $SO_2$ group having the alkyl group as a substituent, and the aryl $SO_2$ group is an $SO_2$ group having the aryl group as a substituent.

The alkyl group having one or more fluorine atoms which one or more hydrogen atoms have been substituted with is an alkyl group in which at least one hydrogen atom in the alkyl group is substituted with a fluorine atom, and includes the alkyl group in which all the hydrogen atoms are substituted with a fluorine atom (hereinafter, these are generally referred to as a fluorinated alkyl group as an abbreviation). Examples of preferable fluorinated alkyl groups include an alkyl group in which all the hydrogen atoms are substituted with a fluorine atom, and specifically include a trifluoromethyl group and a perfluorohexyl group (n-$C_6F_{13}$).

The aryl group having one or more fluorine atoms which one or more hydrogen atoms have been substituted with is an aryl group in which at least one hydrogen atom in the aryl group for the substituent $R^3$ is substituted with a fluorine atom, and includes the aryl group in which all the hydrogen atoms are substituted with a fluorine atom (hereinafter, these are generally referred to as a fluorinated aryl group as an abbreviation). Examples of preferable fluorinated aryl groups include a 4-trifluoromethylphenyl group (4-$CF_3C_6H_5$), and a pentafluorophenyl group ($C_6F_5$) that is an aryl group in which all the hydrogen atoms are substituted with a fluorine atom.

The alkyl $SO_2$ group having one or more fluorine atoms which one or more hydrogen atoms have been substituted with is a fluorinated alkyl $SO_2$ group. A preferable fluorinated alkyl $SO_2$ group is an alkyl $SO_2$ group in which all the hydrogen atoms are substituted with a fluorine atom. Examples thereof include a trifluoromethyl $SO_2$ group and a perfluorohexyl $SO_2$ group.

The aryl $SO_2$ group having one or more fluorine atoms which one or more hydrogen atoms have been substituted with is the fluorinated aryl $SO_2$ group. Examples of preferable fluorinated aryl $SO_2$ groups include a 4-fluorophenyl $SO_2$ group, a 4-trifluoromethylphenyl $SO_2$ group, and a pentafluorophenyl $SO_2$ group that is an aryl $SO_2$ group in which all the hydrogen atoms are substituted with fluorine atoms.

$R^4$ is preferably a methyl group, a trifluoromethyl group, a perfluorohexyl group, a 4-trifluoromethylphenyl group, a pentafluorophenyl group that is an aryl group in which all the hydrogen atoms are substituted with fluorine atoms, a trifluoromethyl $SO_2$ group, a perfluorohexyl $SO_2$ group, a 4-trifluoromethylphenyl $SO_2$ group, and a pentafluorophenyl $SO_2$ group that is an aryl group in which all the hydrogen atoms are substituted with a fluorine atom. $R^4$ is more preferably a methyl group and a trifluoromethyl $SO_2$ group.

Next, the reaction formula (4) will be described. The compound represented by the following formula (3) as the starting material is often available as commercially available products, and can be easily synthesized by the method described in Examples.

Hereinafter, specific examples of the compound as the starting raw material represented by the formula (3), namely the compounds (3)-01 to (3)-85 will be shown, but the present invention will not be limited to these. For convenience, $R^3$ is written as $R^{31}$ and $R^{32}$ below. The blank indicates a hydrogen atom.

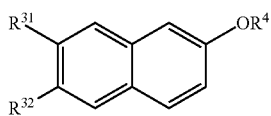

(3)

TABLE 2

| Compound No. | $R^{31}$ | $R^{32}$ | $R^4$ |
|---|---|---|---|
| (3)-01 | Et | | Me |
| (3)-02 | n-Pr | | Me |
| (3)-03 | i-Pr | | Me |
| (3)-04 | n-Bu | | Me |
| (3)-05 | i-Bu | | Me |
| (3)-06 | t-Bu | | Me |
| (3)-07 | n-$C_5H_{11}$ | | Me |
| (3)-08 | n-$C_6H_{13}$ | | Me |
| (3)-09 | n-$C_7H_{15}$ | | Me |
| (3)-10 | n-$C_8H_{17}$ | | Me |
| (3)-11 | n-$C_9H_{19}$ | | Me |
| (3)-12 | n-$C_{10}H_{21}$ | | Me |
| (3)-13 | n-$C_{11}H_{23}$ | | Me |
| (3)-14 | n-$C_{12}H_{25}$ | | Me |
| (3)-15 | n-$C_{13}H_{27}$ | | Me |
| (3)-16 | n-$C_{14}H_{29}$ | | $CF_3PhSO_2$ |
| (3)-17 | n-$C_{16}H_{33}$ | | $CF_3PhSO_2$ |
| (3)-18 | cy-$C_5H_9$ | | $C_5F_5$ |
| (3)-19 | cy-$C_6H_{11}$ | | $CF_3PhSO_2$ |
| (3)-20 | cy-$C_8H_{15}$ | | n-$C_6F_{13}$ |
| (3)-21 | cy-$C_{10}H_{19}$ | | Me |
| (3)-22 | Ph | | Me |
| (3)-23 | 4-Tolyl | | Me |
| (3)-24 | PhPh | | Me |
| (3)-25 | 1-Nap | | Me |
| (3)-26 | 2-Nap | | Me |
| (3)-27 | 2-thienyl | | Me |
| (3)-28 | 4-HexylPh | | Me |
| (3)-29 | 4-OctylPh | | Me |
| (3)-30 | 4-DecylPh | | Me |
| (3)-31 | | Ph | Me |
| (3)-32 | | 4-Tolyl | Me |
| (3)-33 | | PhPh | Me |
| (3)-34 | | 1-Nap | Me |
| (3)-35 | | 2-Nap | Me |
| (3)-36 | | 2-thienyl | Me |
| (3)-37 | | 4-HexylPh | Me |
| (3)-38 | | 4-OctylPh | Me |
| (3)-39 | | 4-DecylPh | Me |
| (3)-40 | n-Bu | Ph | $CF_3SO_2$ |
| (3)-41 | n-$C_6H_{13}$ | Ph | $CF_3SO_2$ |
| (3)-42 | n-$C_8H_{17}$ | Ph | $CF_3SO_2$ |
| (3)-43 | n-$C_{10}H_{21}$ | Ph | $CF_3SO_2$ |
| (3)-44 | n-$C_{12}H_{25}$ | Ph | $CF_3PhSO_2$ |
| (3)-45 | Ph | Ph | Me |
| (3)-46 | 4-Tolyl | Ph | Me |
| (3)-47 | PhPh | Ph | Me |
| (3)-48 | 1-Nap | Ph | Me |
| (3)-49 | 2-thienyl | Ph | Me |
| (3)-50 | Ph | 4-Tolyl | $CF_3SO_2$ |
| (3)-51 | Ph | PhPh | $CF_3SO_2$ |
| (3)-52 | n-$C_8H_{17}$ | n-$C_8H_{17}$ | $CF_3SO_2$ |
| (3)-53 | n-$C_{12}H_{25}$ | n-$C_{12}H_{25}$ | $CF_3SO_2$ |
| (3)-54 | Me | | Me |
| (3)-55 | | Me | Me |
| (3)-56 | | Et | Me |
| (3)-57 | | n-Pr | Me |
| (3)-58 | | n-Bu | Me |
| (3)-59 | | i-Bu | Me |
| (3)-60 | | t-Bu | Me |
| (3)-61 | | n-$C_5H_{11}$ | Me |
| (3)-62 | | n-$C_6H_{13}$ | Me |
| (3)-63 | | n-$C_8H_{17}$ | Me |
| (3)-64 | | n-$C_{10}H_{21}$ | Me |
| (3)-65 | | n-$C_{12}H_{25}$ | Me |
| (3)-66 | | n-$C_{14}H_{29}$ | $CF_3SO_2$ |
| (3)-67 | | n-$C_{16}H_{33}$ | $CF_3SO_2$ |

TABLE 2-continued

| Compound No. | $R^{31}$ | $R^{32}$ | $R^4$ |
|---|---|---|---|
| (3)-68 | | cy-$C_5H_9$ | Me |
| (3)-69 | | cy-$C_6H_{11}$ | Me |
| (3)-70 | | cy-$C_8H_{15}$ | $CF_3SO_2$ |
| (3)-71 | | cy-$C_{10}H_{19}$ | $CF_3SO_2$ |
| (3)-72 | Ph | | $CF_3SO_2$ |
| (3)-73 | | Ph | $CF_3SO_2$ |
| (3)-74 | n-Bu | | $CF_3SO_2$ |
| (3)-75 | n-$C_6H_{13}$ | | $CF_3SO_2$ |
| (3)-76 | n-$C_8H_{17}$ | | $CF_3SO_2$ |
| (3)-77 | n-$C_{10}H_{21}$ | | $CF_3SO_2$ |
| (3)-78 | n-$C_{12}H_{25}$ | | $CF_3SO_2$ |
| (3)-79 | | n-$C_6H_{13}$ | $CF_3SO_2$ |
| (3)-80 | | n-$C_8H_{17}$ | $CF_3SO_2$ |
| (3)-81 | | n-$C_{10}H_{21}$ | $CF_3SO_2$ |
| (3)-82 | 4-Tolyl | | $CF_3SO_2$ |
| (3)-83 | | 4-Tolyl | $CF_3SO_2$ |
| (3)-84 | PhPh | | $CF_3SO_2$ |
| (3)-85 | | PhPh | $CF_3SO_2$ |

Hereinafter, specific examples of the compound (4) as an intermediate (compounds (4)-01 to (4)-85) will be shown, but the present invention will not be limited to these. The blank indicates a hydrogen atom.

TABLE 3

| Compound No. | $R^{31}$ | $R^{32}$ | $R^4$ |
|---|---|---|---|
| (4)-01 | Et | | Me |
| (4)-02 | n-Pr | | Me |
| (4)-03 | i-Pr | | Me |
| (4)-04 | n-Bu | | Me |
| (4)-05 | i-Bu | | Me |
| (4)-06 | t-Bu | | Me |
| (4)-07 | n-$C_5H_{11}$ | | Me |
| (4)-08 | n-$C_6H_{13}$ | | Me |
| (4)-09 | n-$C_7H_{15}$ | | Me |
| (4)-10 | n-$C_8H_{17}$ | | Me |
| (4)-11 | n-$C_9H_{19}$ | | Me |
| (4)-12 | n-$C_{10}H_{21}$ | | Me |
| (4)-13 | n-$C_{11}H_{23}$ | | Me |
| (4)-14 | n-$C_{12}H_{25}$ | | Me |
| (4)-15 | n-$C_{13}H_{27}$ | | Me |
| (4)-16 | n-$C_{14}H_{29}$ | | $CF_3PhSO_2$ |
| (4)-17 | n-$C_{16}H_{33}$ | | $CF_3PhSO_2$ |
| (4)-18 | cy-$C_5H_9$ | | $C_6F_5$ |
| (4)-19 | cy-$C_6H_{11}$ | | $CF_3PhSO_2$ |
| (4)-20 | cy-$C_8H_{15}$ | | n-$C_6F_{13}$ |
| (4)-21 | cy-$C_{10}H_{19}$ | | Me |
| (4)-22 | Ph | | Me |
| (4)-23 | 4-Tolyl | | Me |
| (4)-24 | PhPh | | Me |
| (4)-25 | 1-Nap | | Me |
| (4)-26 | 2-Nap | | Me |
| (4)-27 | 2-thienyl | | Me |
| (4)-28 | 4-HexylPh | | Me |
| (4)-29 | 4-OctylPh | | Me |
| (4)-30 | 4-DecylPh | | Me |
| (4)-31 | | Ph | Me |
| (4)-32 | | 4-Tolyl | Me |
| (4)-33 | | PhPh | Me |
| (4)-34 | | 1-Nap | Me |
| (4)-35 | | 2-Nap | Me |
| (4)-36 | | 2-thienyl | Me |
| (4)-37 | | 4-HexylPh | Me |
| (4)-38 | | 4-OctylPh | Me |

TABLE 3-continued

| Compound No. | R³¹ | R³² | R⁴ |
|---|---|---|---|
| (4)-39 | | 4-DecylPh | Me |
| (4)-40 | n-Bu | Ph | CF₃SO₂ |
| (4)-41 | n-C₆H₁₃ | Ph | CF₃SO₂ |
| (4)-42 | n-C₈H₁₇ | Ph | CF₃SO₂ |
| (4)-43 | n-C₁₀H₂₁ | Ph | CF₃SO₂ |
| (4)-44 | n-C₁₂H₂₅ | Ph | CF₃PhSO₂ |
| (4)-45 | Ph | Ph | Me |
| (4)-46 | 4-Tolyl | Ph | Me |
| (4)-47 | PhPh | Ph | Me |
| (4)-48 | 1-Nap | Ph | Me |
| (4)-49 | 2-thienyl | Ph | Me |
| (4)-50 | Ph | 4-Tolyl | CF₃SO₂ |
| (4)-51 | Ph | PhPh | CF₃SO₂ |
| (4)-52 | n-C₈H₁₇ | n-C₈H₁₇ | CF₃SO₂ |
| (4)-53 | n-C₁₂H₂₅ | n-C₁₂H₂₅ | CF₃SO₂ |
| (4)-54 | Me | | Me |
| (4)-55 | | Me | Me |
| (4)-56 | | Et | Me |
| (4)-57 | | n-Pr | Me |
| (4)-58 | | n-Bu | Me |
| (4)-59 | | i-Bu | Me |
| (4)-60 | | t-Bu | Me |
| (4)-61 | | n-C₅H₁₁ | Me |
| (4)-62 | | n-C₆H₁₃ | Me |
| (4)-63 | | n-C₈H₁₇ | Me |
| (4)-64 | | n-C₁₀H₂₁ | Me |
| (4)-65 | | n-C₁₂H₂₅ | Me |
| (4)-66 | | n-C₁₄H₂₉ | CF₃SO₂ |
| (4)-67 | | n-C₁₆H₃₃ | CF₃SO₂ |
| (4)-68 | | cy-C₅H₉ | Me |
| (4)-69 | | cy-C₆H₁₁ | Me |
| (4)-70 | | cy-C₈H₁₅ | CF₃SO₂ |
| (4)-71 | | cy-C₁₀H₁₉ | CF₃SO₂ |
| (4)-72 | Ph | | CF₃SO₂ |
| (4)-73 | | Ph | CF₃SO₂ |
| (4)-74 | n-Bu | | CF₃SO₂ |
| (4)-75 | n-C₆H₁₃ | | CF₃SO₂ |
| (4)-76 | n-C₈H₁₇ | | CF₃SO₂ |
| (4)-77 | n-C₁₀H₂₁ | | CF₃SO₂ |
| (4)-78 | n-C₁₂H₂₅ | | CF₃SO₂ |
| (4)-79 | | n-C₆H₁₃ | CF₃SO₂ |
| (4)-80 | | n-C₈H₁₇ | CF₃SO₂ |
| (4)-81 | | n-C₁₀H₂₁ | CF₃SO₂ |
| (4)-82 | 4-Tolyl | | CF₃SO₂ |
| (4)-83 | | 4-Tolyl | CF₃SO₂ |
| (4)-84 | PhPh | | CF₃SO₂ |
| (4)-85 | | PhPh | CF₃SO₂ |

Next, the reaction formula (4) will be specifically described. The reaction is a novel reaction. In the compound (3) as the starting material in which an oxygen atom is bonded at the 2-position, the 3-position is highly selectively SMethylated using dimethyl disulfide (Me₂S₂). To develop this reaction, the present inventors studied the base for metalating by hydrogen drawing (alkyl metal reagent, alkyl earth metal reagent) at the 3-position, the reaction solvent, the reaction temperature, and the operation procedure, and found out a production method for highly selectively SMethylating the compound (3) at 3-position using dimethyl disulfide.

Reaction formula (4)

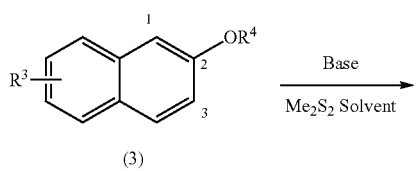

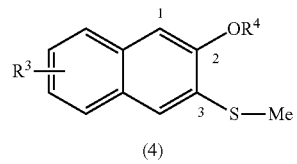

The base used for the reaction is desirably an alkali metal reagent, that is, a lithium reagent, a sodium reagent, and a potassium reagent; and an alkyl earth metal reagent, that is, a magnesium reagent and a calcium reagent. Specifically, methyllithium, n-butyllithium, t-butyllithium, phenyllithium, methylmagnesium chloride, butylmagnesium chloride, and the like can be used. Particularly preferably, use of butyllithium is desirable because it is a stable and strong base.

The amount of the base to be used is desirably 0.5 mol or more and 10 mol or less based on 1 mol of the compound (3). The base may be further added in the range of the above amount to the reaction solution prepared by adding the compound (3) to the base. By adding the base in two steps as above, the hydrogen atom at the 3-position in the compound (3) may be smoothly drawn.

In the method for producing the compound according to the present embodiment, a basic compound (an additive) may be added together with the alkyl metal reagent for stabilization of the lithium reagent and the like. Examples of the basic compound can include N,N,N'-trimethylethylenediamine, dimethylamine, diisopropylamine, and morpholine.

The reaction is desirably carried out under an inert gas atmosphere such as under an argon atmosphere, under a nitrogen replacement, under a dry argon atmosphere, and under a dry nitrogen stream.

The reaction temperature in reacting the compound (3) with the base is preferably in the range of −100° C. to 30° C., and more preferably −80° C. to 10° C.

In the reaction, any solvent can be used. Desirably, the solvent to be used is an ether solvent, an aliphatic solvent, or an aromatic solvent. These solvents are desirably dehydrated and used.

Examples of the ether solvent to be used for the reaction include tetrahydrofuran (THF), diethyl ether, dimethoxyethane, and dioxane. Examples of the aliphatic solvent include n-pentane, n-hexane, and n-heptane. Examples of the aromatic solvent include toluene and xylene.

The amount of dimethyl disulfide to be used in the reaction is desirably 0.5 mol or more and 10 mol or less based on 1 mol of the compound (3).

In refining the compound (4) obtained above, the refining method is not particularly limited. A known refining method can be used depending on the physical properties of the compound. Specifically, the compound can be refined by recrystallization, column chromatography, and the like.

The reaction for highly selective SMethylation at the 3-position of the compound (3) having an oxygen atom at the 2-position by using dimethyl disulfide had not been known in the related art. To develop the reaction, the present inventors studied the base for metalating to the 3-position by hydrogen drawing as above (alkyl metal reagent, alkyl earth metal reagent), the reaction solvent, the reaction temperature, and the operation procedure, and as a result, found out the method for highly selective SMethylation at the 3-position in the compound (3) using dimethyl disulfide, namely, the method for highly selectively producing the compound (4).

Subsequently, the compound (5) to be reacted with the compound (4) and the compound (6) as a product of the reaction formula (5) will be described.

In the formula (5) that is a tin compound, $R^5$ represents an alkyl group. Examples of the alkyl group include linear or branched alkyl groups. The alkyl groups have 1 to 8 carbon atoms, preferably 1 to 4 carbon atoms, and more preferably 4 carbon atoms. Here, specific examples of the linear alkyl group include methyl, ethyl, n-propyl, n-butyl, n-pentyl, and n-hexyl. Specific examples of the branched alkyl group include C3-C6 saturated branched alkyl groups such as i-propyl, i-butyl, t-butyl, i-pentyl, and i-hexyl. An n-butyl group is preferable because of its availability.

Hereinafter, specific examples of the tin compound represented by the formula (5) will be shown, but the present invention will not be limited to these.

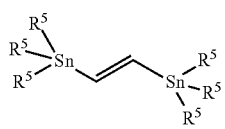
(5)

TABLE 4

| Compound No. | $R^5$ |
| --- | --- |
| (5)-01 | Me |
| (5)-02 | Et |
| (5)-03 | n-Pr |
| (5)-04 | i-Pr |
| (5)-05 | n-Bu |
| (5)-06 | i-Bu |
| (5)-07 | t-Bu |

$R^3$ ($R^{31}$ and $R^{32}$) in the compound (6) means the same as $R^3$ ($R^{31}$ and $R^{32}$) in the compound (3).

Hereinafter, specific examples of the compound (6) (compounds (6)-01 to (6)-71) will be shown, but the present invention will not be limited to these. $R^3$ in the compound (6) is also written as $R^{31}$ and $R^{32}$ for convenience.

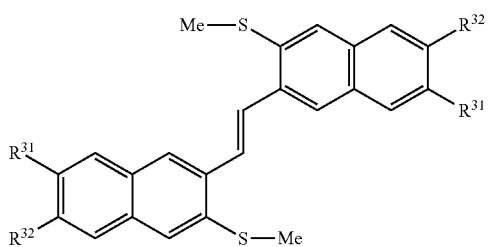
(6)

TABLE 5

| Compound No. | $R^{31}$ | $R^{32}$ |
| --- | --- | --- |
| (6)-01 | Et | |
| (6)-02 | n-Pr | |
| (6)-03 | i-Pr | |
| (6)-04 | n-Bu | |
| (6)-05 | i-Bu | |
| (6)-06 | t-Bu | |
| (6)-07 | n-C$_5$H$_{11}$ | |
| (6)-08 | n-C$_6$H$_{13}$ | |
| (6)-09 | n-C$_7$H$_{15}$ | |
| (6)-10 | n-C$_8$H$_{17}$ | |
| (6)-11 | n-C$_9$H$_{19}$ | |
| (6)-12 | n-C$_{10}$H$_{21}$ | |
| (6)-13 | n-C$_{11}$H$_{23}$ | |
| (6)-14 | n-C$_{12}$H$_{25}$ | |
| (6)-15 | n-C$_{13}$H$_{27}$ | |
| (6)-16 | n-C$_{14}$H$_{29}$ | |
| (6)-17 | n-C$_{16}$H$_{33}$ | |
| (6)-18 | cy-C$_5$H$_9$ | |
| (6)-19 | cy-C$_6$H$_{11}$ | |
| (6)-20 | cy-C$_8$H$_{15}$ | |
| (6)-21 | cy-C$_{10}$H$_{19}$ | |
| (6)-22 | Ph | |
| (6)-23 | 4-Tolyl | |
| (6)-24 | PhPh | |
| (6)-25 | 1-Nap | |
| (6)-26 | 2-Nap | |
| (6)-27 | 2-thienyl | |
| (6)-28 | 4-HexylPh | |
| (6)-29 | 4-OctylPh | |
| (6)-30 | 4-DecylPh | |
| (6)-31 | | Ph |
| (6)-32 | | 4-Tolyl |
| (6)-33 | | PhPh |
| (6)-34 | | 1-Nap |
| (6)-35 | | 2-Nap |
| (6)-36 | | 2-thienyl |
| (6)-37 | | 4-HexylPh |
| (6)-38 | | 4-OctylPh |
| (6)-39 | | 4-DecylPh |
| (6)-40 | n-Bu | Ph |
| (6)-41 | n-C$_6$H$_{13}$ | Ph |
| (6)-42 | n-C$_8$H$_{17}$ | Ph |
| (6)-43 | n-C$_{10}$H$_{21}$ | Ph |
| (6)-44 | n-C$_{12}$H$_{25}$ | Ph |
| (6)-45 | Ph | Ph |
| (6)-46 | 4-Tolyl | Ph |
| (6)-47 | PhPh | Ph |
| (6)-48 | 1-Nap | Ph |
| (6)-49 | 2-thienyl | Ph |
| (6)-50 | Ph | 4-Tolyl |
| (6)-51 | Ph | PhPh |
| (6)-52 | n-C$_8$H$_{17}$ | n-C$_8$H$_{17}$ |
| (6)-53 | n-C$_{12}$H$_{25}$ | n-C$_{12}$H$_{25}$ |
| (6)-54 | Me | |
| (6)-55 | | Me |
| (6)-56 | | Et |
| (6)-57 | | n-Pr |
| (6)-58 | | n-Bu |
| (6)-59 | | i-Bu |
| (6)-60 | | t-Bu |
| (6)-61 | | n-C$_5$H$_{11}$ |
| (6)-62 | | n-C$_6$H$_{13}$ |
| (6)-63 | | n-C$_8$H$_{17}$ |
| (6)-64 | | n-C$_{10}$H$_{21}$ |
| (6)-65 | | n-C$_{12}$H$_{25}$ |
| (6)-66 | | n-C$_{14}$H$_{29}$ |
| (6)-67 | | n-C$_{16}$H$_{33}$ |
| (6)-68 | | cy-C$_5$H$_9$ |
| (6)-69 | | cy-C$_6$H$_{11}$ |
| (6)-70 | | cy-C$_8$H$_{15}$ |
| (6)-71 | | cy-C$_{10}$H$_{19}$ |

In the conventional techniques, a raw material aldehyde body for synthesizing the compound (6) (the compound (B) in the reaction formula 2) is very difficult to synthesize (Patent Literature 3 and Non Patent Literature 1). In the present invention, the compound (5) is reacted when the oxygen atoms at the 2-positions in the two molecules of compound (4) having an MeS group at the 3-position are eliminated. This reaction enables highly selective production of the compound (6) (see the reaction formula (5)). Usually, the reaction shown in the reaction formula (5) uses a Pd compound as a catalyst. Pd is easily poisoned by a sulfur compound, and may lose activity quickly. For this reason, the present inventors studied the catalyst, reaction solvent, reaction temperature, and operation procedure that allowed oxygen in the compound (4) to be effectively eliminated and the compound (4) to react with the compound (5) as above, and found out the production method that can produce the compound (6) from the two molecules of compound (4) at a high selectively and at a high yield.

Hereinafter, the reaction formula (5) will be specifically described.

Reaction formula (5)

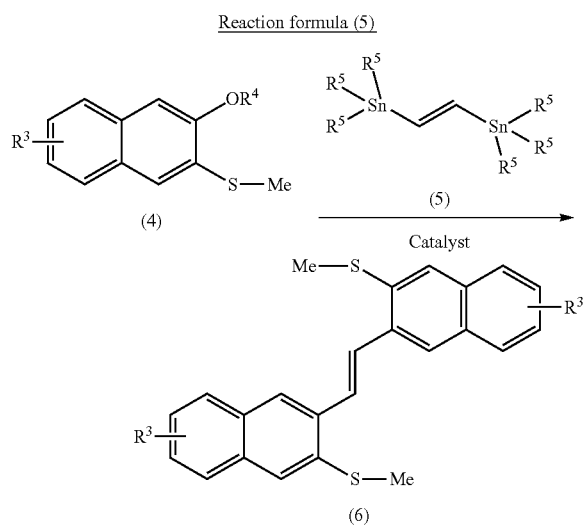

Here, R⁴ in the compound (4) can be converted to an optimal substituent when necessary for use when the reaction shown in the reaction formula (5) is carried out. Namely, R⁴ can be converted properly as shown in Examples.

In the reaction shown in the reaction formula (5), the mixing ratio of the compound (4) to the compound (5) is preferably 1.8 mol to 2.5 mol based on 1 mol of the compound (5). The reaction is carried out at the mixing ratio of more preferably 1.95 mol to 2.10 mol, and still more preferably 1.95 mol to 2.05 mol.

Alternatively, first, the compound (4) can be reacted with the compound (5) at a proportion of approximately 1:1. Subsequently, the compound (4) having a different substituent from that in the compound (4) previously added is added, and the reaction is carried out. This can synthesize an asymmetric intermediate (6).

The catalyst used in the reaction can be any Pd or Ni catalyst. At least one catalyst may contain at least one compound selected from the group consisting of nickel and palladium catalysts having a ligand selected from the group consisting of tri-tert-butylphosphine, triadamantylphosphine, 1,3-bis(2,4,6-trimethylphenyl)imidazolidinium chloride, 1,3-bis(2,6-diisopropylphenyl)imidazolidinium chloride, 1,3-diadamantylimidazolidinium chloride, or a mixture thereof; metal Pd, Pd/C (hydrous or nonhydrous), bis(triphenyl phosphino)palladium dichloride (Pd(PPh₃)₂Cl₂), palladium(II) acetate (Pd(OAc)₂), tetrakis(triphenylphosphine) palladium (Pd(PPh₃)₄), tetrakis(triphenylphosphine)nickel (Ni(PPh₃)₄), nickel(II) acetylacetonate Ni(acac)₂, dichloro(2, 2'-bipyridine)nickel, dibromobis(triphenylphosphine)nickel (Ni(PPh₃)₂Br₂), bis(diphenylphosphino)propanenickel dichloride (Ni((dppp)Cl₂), bis(diphenylphosphino)ethanenickel dichloride Ni(dppe)Cl₂, and a mixture thereof. Examples of preferable catalysts include Pd/C (hydrous or nonhydrous), Pd(PPh₃)₂Cl₂, and Pd(PPh₃)₄, and examples of more preferable catalysts include Pd(PPh₃)₂Cl₂ and Pd(PPh₃)₄.

The amount of the catalyst to be used is desirably 0.001 mol or more and 0.5 mol or less based on 1 mol of the compound (4). The catalyst may be added in the range of the amount used above to the reaction solution prepared by adding the compound (4), the compound (5), and the catalyst. When the catalyst is poisoned by sulfur or the like to deactivate the catalyst, addition of the catalyst in two or more steps is effective because such operation may prevent reduction in the reaction rate.

The reaction temperature in reacting the compound (4) with the compound (5) is usually −10° C. to 200° C. The reaction temperature is more preferably 40° C. to 180° C., and still more preferably 80° C. to 150° C.

The reaction is desirably carried out under an inert gas atmosphere such as under an argon atmosphere, under nitrogen replacement, under a dry argon atmosphere, and under a dry nitrogen stream.

In the reaction, the solvent may or may not be used. Any solvent can be used as long as it is a solvent used in typical organic synthesis. Examples of the solvent can include aromatic compounds such as chlorobenzene, o-dichlorobenzene, bromobenzene, nitrobenzene, toluene, and xylene; saturated aliphatic hydrocarbons such as n-hexane, n-heptane, and n-pentane; alicyclic hydrocarbons such as cyclohexane, cycloheptane, and cyclopentane; saturated aliphatic halogenated hydrocarbons such as n-propyl bromide, n-butyl chloride, n-butyl bromide, dichloromethane, dibromomethane, dichloropropane, dibromopropane, dichloroethane, dibromoethane, dichloropropane, dibromopropane, dichlorobutane, chloroform, bromoform, carbon tetrachloride, carbon tetrabromide, trichloroethane, tetrachloroethane, and pentachloroethane; halogenated cyclic hydrocarbons such as chlorocyclohexane, chlorocyclopentane, and bromocyclopentane; esters such as ethyl acetate, propyl acetate, butyl acetate, methyl propionate, ethyl propionate, propyl propionate, butyl propionate, methyl butyrate, ethyl butyrate, propyl butyrate, and butyl butyrate; and ketones such as acetone, methyl ethyl ketone, and methyl isobutyl ketone. These solvents may be used singly, or may be used by mixing two or more.

At least one high boiling point solvent having a boiling point of 100° C. or more is preferably used as the reaction solvent because the reaction rate significantly improves or the selectivity of the reaction increases.

The high boiling point solvent having a boiling point of 100° C. or more is preferably amides (N-methyl-2-pyrrolidone (hereinafter, NMP), N,N-dimethylformamide (hereinafter, abbreviated to DMF), N,N-dimethylacetamide (hereinafter, DMAc)); glycols (ethylene glycol, propylene glycol, and polyethylene glycol); and sulfoxides (dimethyl sulfoxide (hereinafter, abbreviated to DMSO)), and more preferably N-methyl-2-pyrrolidone, N,N-dimethylformamide, and N,N-dimethylacetamide.

In refining of the obtained compound (6), the refining method is not particularly limited. A known refining method can be used depending on the properties of the compound (6). Specifically, the compound can be refined by recrystallization, column chromatography, and the like.

Next, the reaction formula (6) will be described. Hereinafter, specific examples of the compound (2) obtained by cyclizing the compound (6) obtained by the reaction shown in the reaction formula (5) will be described, but the present invention will not be limited to these. The compounds (2)-01 to 53 are the same compounds as the compounds (1)-01 to 53. Hereinafter, the compounds are referred using the compounds (1)-01 to 53. The production method of the present invention can provide the compound (2) at a high yield from the compound (6) by the same method specifically described in Non Patent Literature 1, Patent Literature 3, Patent Literature 6, Patent Literature 7, and Patent Literature 8. In the compound (2), $R^3$ is written as $R^{31}$ and $R^{32}$ for convenience.

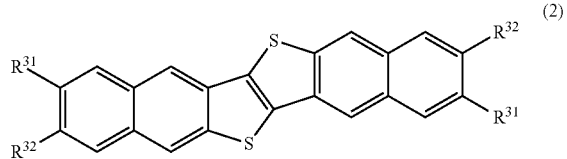

(2)

TABLE 6

| Compound No. | $R^{31}$ | $R^{32}$ |
|---|---|---|
| (2)-01 | Et | |
| (2)-02 | n-Pr | |
| (2)-03 | i-Pr | |
| (2)-04 | n-Bu | |
| (2)-05 | i-Bu | |
| (2)-06 | t-Bu | |
| (2)-07 | n-$C_5H_{11}$ | |
| (2)-08 | n-$C_6H_{13}$ | |
| (2)-09 | n-$C_7H_{15}$ | |
| (2)-10 | n-$C_8H_{17}$ | |
| (2)-11 | n-$C_9H_{19}$ | |
| (2)-12 | n-$C_{10}H_{21}$ | |
| (2)-13 | n-$C_{11}H_{23}$ | |
| (2)-14 | n-$C_{12}H_{25}$ | |
| (2)-15 | n-$C_{13}H_{27}$ | |
| (2)-16 | n-$C_{14}H_{29}$ | |
| (2)-17 | n-$C_{16}H_{33}$ | |
| (2)-18 | cy-$C_5H_9$ | |
| (2)-19 | cy-$C_6H_{11}$ | |
| (2)-20 | cy-$C_8H_{15}$ | |
| (2)-21 | cy-$C_{10}H_{19}$ | |
| (2)-22 | Ph | |
| (2)-23 | 4-Tolyl | |
| (2)-24 | PhPh | |
| (2)-25 | 1-Nap | |
| (2)-26 | 2-Nap | |
| (2)-27 | 2-thienyl | |
| (2)-28 | 4-HexylPh | |
| (2)-29 | 4-OctylPh | |
| (2)-30 | 4-DecylPh | |
| (2)-31 | | Ph |
| (2)-32 | | 4-Tolyl |
| (2)-33 | | PhPh |
| (2)-34 | | 1-Nap |
| (2)-35 | | 2-Nap |
| (2)-36 | | 2-thienyl |
| (2)-37 | | 4-HexylPh |
| (2)-38 | | 4-OctylPh |
| (2)-39 | | 4-DecylPh |
| (2)-40 | n-Bu | Ph |
| (2)-41 | n-$C_6H_{13}$ | Ph |
| (2)-42 | n-$C_8H_{17}$ | Ph |
| (2)-43 | n-$C_{10}H_{21}$ | Ph |
| (2)-44 | n-$C_{12}H_{25}$ | Ph |
| (2)-45 | Ph | Ph |
| (2)-46 | 4-Tolyl | Ph |
| (2)-47 | PhPh | Ph |
| (2)-48 | 1-Nap | Ph |
| (2)-49 | 2-thienyl | Ph |
| (2)-50 | Ph | 4-Tolyl |
| (2)-51 | Ph | PhPh |
| (2)-52 | n-$C_8H_{17}$ | n-$C_8H_{17}$ |
| (2)-53 | n-$C_{12}H_{25}$ | n-$C_{12}H_{25}$ |
| (2)-54 | Me | |
| (2)-55 | | Me |

TABLE 6-continued

| Compound No. | $R^{31}$ | $R^{32}$ |
|---|---|---|
| (2)-56 | | Et |
| (2)-57 | | n-Pr |
| (2)-58 | | n-Bu |
| (2)-59 | | i-Bu |
| (2)-60 | | t-Bu |
| (2)-61 | | n-$C_5H_{11}$ |
| (2)-62 | | n-$C_6H_{13}$ |
| (2)-63 | | n-$C_8H_{17}$ |
| (2)-64 | | n-$C_{10}H_{21}$ |
| (2)-65 | | n-$C_{12}H_{25}$ |
| (2)-66 | | n-$C_{14}H_{29}$ |
| (2)-67 | | n-$C_{16}H_{33}$ |
| (2)-68 | | cy-$C_5H_9$ |
| (2)-69 | | cy-$C_6H_{11}$ |
| (2)-70 | | cy-$C_8H_{15}$ |
| (2)-71 | | cy-$C_{10}H_{19}$ |

The field effect transistor of the present invention (Field effect transistor, hereinafter, abbreviated to FET in some cases) has two electrodes (source electrode and drain electrode) contacting the semiconductor. The current flowing between the electrodes is controlled by the voltage applied to another electrode called the gate electrode.

Typically, the structure of the field effect transistor often used is the structure (Metal-Insulator-Semiconductor; MIS structure) in which the gate electrode is insulated with an insulation film. The structure of the field effect transistor using a metal oxide film as the insulation film is called a MOS structure. Besides, another known structure is the structure in which the gate electrode is formed with a Schottky barrier being interposed, namely, a MES structure. The MIS structure is often used for the FET using an organic semiconductor material.

Hereinafter, using the drawings, the organic field effect transistor according to the present invention will be more specifically described, but the present invention will not be limited to these structures.

Some examples of embodiments of the field effect transistor according to the present invention (element) are shown in FIG. 1. In the respective examples, a source electrode 1, a semiconductor layer 2, a drain electrode 3, an insulator layer 4, a gate electrode 5, and a substrate 6 are shown. The arrangement of the respective layers and electrodes can be properly selected depending on the application of the element. These field effect transistors shown in schematic views A to D are called the lateral FET in which the current flows in the direction parallel to the substrate. The structure shown in the schematic view A is called the bottom contact structure, and the structure shown in the schematic view B is called the top contact structure. The structure shown in the schematic view C is a structure often used in creation of an organic single-crystal FET, in which source and drain electrodes, and an insulator layer are provided on a semiconductor and a gate electrode is formed thereon. The structure shown in the schematic view D is a structure called the top & bottom contact type transistor. The schematic view E is a schematic view showing an FET having a vertical structure, namely, a static induction transistor (SIT). In the SIT, the flow of the current extends planarly, a large amount of carriers can move at one time. The source electrode and the drain electrode are arranged vertically. This arrangement can reduce the distance between the electrodes, attaining fast response. Consequently, the SIT is preferably used in applications in which a large amount of current is flown, high-speed switching is performed, or the like. In E of FIG. 1, no substrate is shown.

In typical cases, substrates are provided on the outer sides of the source and drain electrodes 1 and 3 in E of FIG. 1.

Components in the examples of the respective embodiments will be described.

The substrate 6 needs to hold the layers to be formed thereon without the layers being peeled off. For the substrate 6, insulation materials such as resin plates and films, paper, glass, quartz, and ceramics; a conductive substrate made of a metal, an alloy, or the like and having an insulator layer formed thereon by coating or the like; materials formed of a combination of various materials such as a resin and an inorganic material; and the like can be used, for example. Examples of usable resin films include polyethylene terephthalate, polyethylene naphthalate, polyethersulfone, polyamide, polyimide, polycarbonate, cellulose triacetate, and polyetherimide. Use of the resin film or paper can provide flexibility of the element, and can attain a flexible and light element. Practicality also improves. The thickness of the substrate is usually 1 μm to 10 mm, and preferably 5 μm to 5 mm.

A conductive material is used for the source electrode 1, the drain electrode 3, and the gate electrode 5. For example, metals such as platinum, gold, silver, aluminum, chromium, tungsten, tantalum, nickel, cobalt, copper, iron, lead, tin, titanium, indium, palladium, molybdenum, magnesium, calcium, barium, lithium, potassium, sodium and alloys containing these; conductive oxides such as $InO_2$, $ZnO_2$, $SnO_2$, and ITO; conductive high-molecular compounds such as polyaniline, polypyrrole, polythiophene, polyacetylene, poly-paraphenylene, vinylene, and polydiacetylene; semiconductors such as silicon, germanium, and gallium arsenic; carbon materials such as carbon black, fullerene, carbon nanotube, and graphite; and the like can be used. The conductive high-molecular compound or the semiconductor may be doped. Examples of the dopant include inorganic acids such as hydrochloric acid and sulfuric acid; organic acids having an acidic functional group such as sulfonic acid; Lewis acids such as $PF_5$, $AsF_5$, and $FeCl_3$; halogen atoms such as iodine; and metal atoms such as lithium, sodium, and potassium. Boron, phosphorus, arsenic, and the like are often used as a dopant for an inorganic semiconductor such as silicon. A conductive composite material prepared by dispersing carbon black or a metal particle in the dopant also is used.

The source and drain electrodes contact the semiconductor substance directly and have a role to inject charges such as electrons or holes into the semiconductor. To reduce the contact resistance to facilitate injection of charges, it is important to match the HOMO level and LUMO level of the semiconductor material with the work function of the electrode. To reduce the contact resistance to provide an ohmic element, semiconductor properties can be improved by interposing of an injection improvement layer formed of a material such as molybdenum oxide and tungsten oxide, doping of the metal electrode, surface modification by a single-molecular film, or the like.

The distance between the source electrode and the drain electrode (channel length) is an important factor that determines the properties of the element. The channel length is usually 0.1 to 300 μm, and preferably 0.5 to 100 μm. As the channel length is shorter, the amount of the current to be extracted increases but leakage current or the like occurs. For this reason, a proper channel length needs to be set. The width between the source electrode and the drain electrode (channel width) is usually 10 to 5000 μm, and preferably 100 to 2000 μm. The channel width can be longer by using a combed structure for the structure of the electrode or the like. The channel width may be properly set depending on the amount of the current needed, the structure of the element, and the like.

The structures (shapes) of the source electrode and drain electrode will be described. The structure of the source electrode and that of the drain electrode may be the same or different from each other. For the bottom contact structure, usually, the respective electrodes are preferably created using lithography, and formed into a rectangular parallelepiped. The length of the electrode may be equal to the channel width. The width of the electrode is not particularly limited. Preferably, the width is shorter for the purpose of reducing the area of the element in the range in which electrical properties can be stabilized. The width of the electrode is usually 0.1 to 1000 μm, and preferably 0.5 to 100 μm. The thickness of the electrode is usually 0.1 to 1000 nm, preferably 1 to 500 nm, and more preferably 5 to 200 nm. The electrodes 1, 3, and 5 each have wiring connected thereto. The wiring also is created using substantially the same material as that for the electrode.

For the insulator layer 4, a material having insulation properties is used. For example, polymers such as poly(paraxylylene), polyacrylate, polymethyl methacrylate, polystyrene, polyvinyl phenol, polyamide, polyimide, polycarbonate, polyester, polyvinyl alcohol, polyvinyl acetate, polyurethane, polysulfone, epoxy resins, phenol resins, fluorine resins and copolymers in combination thereof; metal oxides such as silicon dioxide, aluminum oxide, titanium oxide, and tantalum oxide; ferroelectric metal oxides such as $SrTiO_3$ and $BaTiO_3$; nitrides such as silicon nitride and aluminum nitride; sulfides; dielectric substances such as fluoride; or polymers prepared by dispersing particles of these dielectric substances; and the like can be used. The film thickness of the insulator layer 4 depends on the material, and is usually 0.1 nm to 100 μm, preferably 0.5 nm to 50 μm, and more preferably 1 nm to 10 μm.

For the semiconductor layer 2 in the present invention, an organic thin film comprising one or two or more heterocyclic compounds represented by the compound (1) above is used. The compound in the organic thin film may be a mixture. Preferably, the organic thin film contains usually 50% by mass or more, preferably 80% by mass or more, and still more preferably 95% by mass or more of the compound (1).

The field effect transistor of the present invention uses an organic thin film formed of at least one heterocyclic compound represented by the compound (1) as the semiconductor material. Substantially, the semiconductor material made of a single heterocyclic compound is preferably used rather than the semiconductor material made of a mixture of a plurality of heterocyclic compounds represented by the compound (1).

To improve the properties of the field effect transistor or give other properties, however, other organic semiconductor materials and a variety of additives may be mixed when necessary.

The additives can be added in the range of usually 0.01 to 10% by mass, preferably 0.05 to 5% by mass, and more preferably 0.1 to 3% by mass based on the total amount of the semiconductor material.

The semiconductor layer may be composed of a plurality of organic thin film layers, but the semiconductor layer more preferably has a single layer structure.

The film thickness of the semiconductor layer 2 is preferably thinner in the range in which the necessary function is not lost. The reason is as follows: in the lateral field effect transistors shown in the schematic views A, B, and D, when the semiconductor layer has a predetermined film thickness or more, the properties of the element do not depend on the film thickness; meanwhile, a thicker film thickness often increases leakage current. The film thickness of the semiconductor layer for exhibiting the necessary function is usually 1 nm to 10 μm, preferably 5 nm to 5 μm, and more preferably 10 nm to 3 μm.

The field effect transistor of the present invention can have other layers provided between the substrate and the insulation film layer, between the insulation film layer and the semiconductor layer, or on the outer surface of the element, for example, when necessary. For example, a protective layer is formed on the semiconductor layer directly or with another layer being interposed. The protective layer can reduce the influence of outside air such as humidity, and increase the ON/OFF ratio of the element. Thus, the protective layer can advantageously stabilize electrical properties.

The material for the protective layer is not particularly limited. For example, films formed of a variety of resins such as an acrylic resin such as an epoxy resin and polymethyl methacrylate, polyurethane, polyimide, polyvinyl alcohol, a fluorinated resin, and polyolefin; inorganic oxide films formed of silicon oxide, aluminum oxide, silicon nitride, or the like; and films formed of a dielectric substance such as nitride films; and the like are preferably used. Particularly, resins (polymers) having a low permeability or absorption rate of oxygen or moisture are preferable. A protective material developed for organic EL displays has also recently been able to be used. Any film thickness of the protective layer can be selected according to the purpose. The film thickness is usually 100 nm to 1 mm.

The substrate or insulator layer on which the semiconductor layer is laminated can be subjected to a surface treatment in advance to improve film forming properties of the semiconductor material and the properties of the element. Particularly, the properties of the organic semiconductor material may change depending on the state of the film such as orientation of the molecule. For example, by adjusting the degree of hydrophilicity/hydrophobicity of the substrate surface, the properties of the film to be formed on the substrate can be improved. Particularly, the properties of the organic semiconductor material may significantly change depending on the state of the film such as orientation of the molecule. Probably, for this reason, the surface treatment of the substrate can improve in the properties such as carrier mobility because the surface treatment controls orientation of the molecule at the interface between the substrate or the like and the semiconductor layer to be formed thereon, or reduces trap sites on the substrate or insulator layer.

The trap site means a functional group existing in the non-treated substrate such as a hydroxyl group. If such a functional group exists, the functional group attracts electrons, reducing carrier mobility. Consequently, reduction in the trap site is also effective in improving properties such as carrier mobility in many cases.

Examples of the treatment of the substrate for improving the properties include a hydrophobization treatment using hexamethyldisilazane, cyclohexene, octyltrichlorosilane, octadecyltrichlorosilane, or the like; an acid treatment using hydrochloric acid, sulfuric acid, acetic acid, and the like; an alkali treatment using sodium hydroxide, potassium hydroxide, calcium hydroxide, ammonia, or the like; an ozone treatment; a fluorination treatment; a plasma treatment using oxygen, argon, or the like; a Langmuir-Blodgett film forming treatment; a treatment of forming a thin film of other insulators or semiconductors; mechanical treatment; an electrical treatment such as corona discharge; or a rubbing treatment using fibers or the like. However, the field effect transistor using the compound of the present invention has a small influence of the material over the substrate or insulator layer. This feature eliminates more expensive treatments and adjustment of the state of the surface, and enables use of a broader range of materials, leading to general versatility and cost reduction.

In these embodiments, as a method for forming the layers such as an insulation film layer and a semiconductor layer, a vacuum evaporation method, a sputter method, a coating method, a printing method, a sol-gel method, and the like can be properly used, for example.

Next, the method for producing a field effect transistor according to the present invention will be described below based on FIG. 2 using the bottom contact type field effect transistor (FET) shown in Embodiment A in FIG. 1 as an example.

The production method can be used for the field effect transistor according to other embodiments.

(Substrate and Treatment of Substrate)

Figure 2:
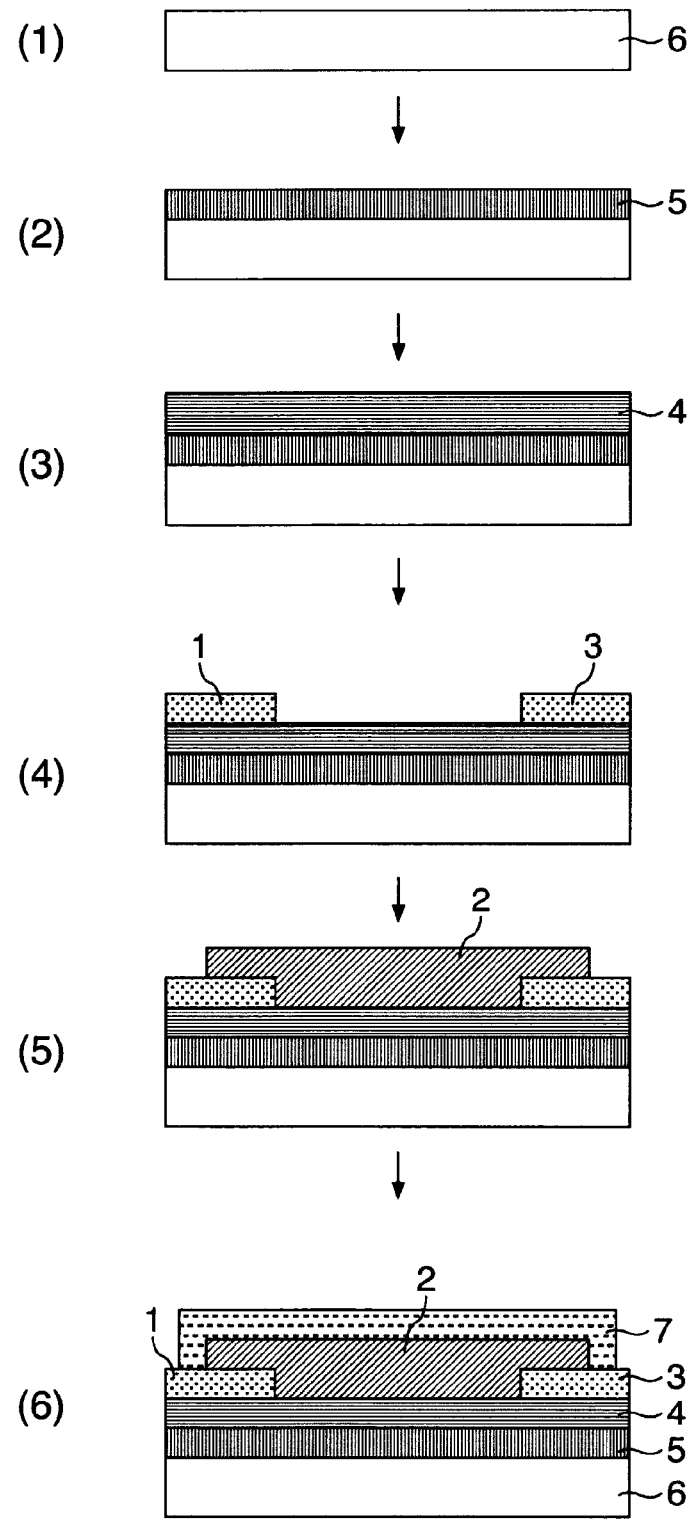
FIG. 2 is a schematic view showing steps for producing one embodiment of the field effect transistor according to the present invention.

The field effect transistor of the present invention is created by forming a variety of necessary layers and electrodes on the substrate 6 (see (1) of FIG. 2). The substrate described above can be used. The substrate can be subjected to the surface treatment described above. The thickness of the substrate 6 is preferably thinner in the range in which the necessary function is not inhibited. Depending on the material, the thickness is usually 1 μm to 10 mm, and preferably 5 μm to 5 mm. The substrate may function as an electrode when necessary.

(Formation of Gate Electrode)

The gate electrode 5 is formed on the substrate 6 (see (2) of FIG. 2). The electrode material described above is used. For the method for forming an electrode film, a variety of methods can be used: for example, a vacuum evaporation method, a sputter method, a coating method, a thermal transfer method, a printing method, a sol-gel method, and the like. During or after film formation, patterning is preferably performed when necessary to have a desired shape. Moreover, a variety of patterning methods can be used. Examples thereof include photolithography using patterning and etching of a photoresist in combination. The patterning can also be performed using a printing method such as inkjet printing, screen printing, offset printing, and relief printing, a soft lithography method such as a microcontact printing method, and a method using these in combination. The film thickness of the gate electrode 5 depends on the material, and is usually 0.1 nm to 10 μm, preferably 0.5 nm to 5 μm, and more preferably 1 nm to 1 μm. The film thickness may be larger than above when the substrate functions as the gate electrode.

(Formation of Insulator Layer)

The insulator layer 4 is formed on the gate electrode 5 (see (3) of FIG. 2). The insulator material described above is used, for example. In formation of the insulator layer 4, a variety of methods can be used. Examples of the method include coating methods such as spin coating, spray coating, dip coating, casting, bar coating, and blade coating; printing methods such as screen printing, offset printing, and inkjet printing; and dry process methods such as a vacuum evaporation method, a molecular beam epitaxial growth method, an ion cluster beam method, an ion plating method, a sputtering method, an atmospheric pressure plasma method, and a CVD method. Besides, a sol-gel method, a method for forming an oxide film on a metal, for example, forming anodized aluminum on aluminum or silicon dioxide on silicon, and the like are used.

In the portion in which the insulator layer contacts the semiconductor layer, the insulator layer may be subjected to a predetermined surface treatment to well orient the molecule that constitutes the semiconductor at the interface between these layers such as the molecule of the heterocyclic compound represented by the compound (1). For the method for the surface treatment, the same method as the surface treatment of the substrate can be used. The film thickness of the insulator layer 4 is preferably thinner in the range in which the function is not impaired. The film thickness is usually 0.1 nm to 100 µm, preferably 0.5 nm to 50 µm, and more preferably 5 nm to 10 µm.

(Formation of Source Electrode and Drain Electrode)

The source electrode 1 and the drain electrode 3 can be formed according to the method for producing the gate electrode 5 (see (4) of FIG. 2).

(Formation of Semiconductor Layer)

An organic thin film comprising one or two or more heterocyclic compounds represented by the compound (1) is formed on the insulator layer 4, the source electrode 1, and the drain electrode 3 as a semiconductor layer. For the semiconductor material, an organic material containing usually the total amount of 50% by mass or more of one heterocyclic compound represented by the compound (1) or a mixture of the heterocyclic compounds is used as described above. In formation of the semiconductor layer, a variety of methods can be used. The methods are mainly classified into vacuum process formation methods such as a sputtering method, a CVD method, a molecular beam epitaxial growth method, and a vacuum evaporation method; coating methods such as a dip coating method, a die coater method, a roll coater method, a bar coater method, and a spin coating method; solution process formation methods such as an inkjet method, a screen printing method, an offset printing method, and a microcontact printing method.

When the organic thin film functioning as the semiconductor layer is formed using the heterocyclic compound represented by the compound (1) of the present invention as the semiconductor material, a method for forming the organic thin film formed by the vacuum process as the semiconductor layer is preferable, and the vacuum evaporation method is more preferable. Film formation by the solution process can be used, and an inexpensive printing method can be used.

A method for forming a film using an organic material by a vacuum process to obtain an organic thin film will be described.

In the present invention, the method for heating the organic material in a crucible or a metal boat under vacuum, and applying (depositing) the evaporated organic material onto a substrate (exposed portions of the insulator layer, the source electrode, and the drain electrode), namely, the vacuum evaporation method is preferably used. At this time, the degree of vacuum is usually $1.0 \times 10^{-1}$ Pa or less, and preferably $1.0 \times 10^{-3}$ Pa or less. The substrate temperature during deposition may change the organic semiconductor film, and the properties of the field effect transistor as a result. The substrate temperature needs to be carefully selected. The substrate temperature during deposition is usually 0 to 200° C., preferably 10 to 150° C., more preferably 15 to 120° C., and still more preferably 25 to 100° C.

The deposition rate is usually 0.001 nm/sec to 10 nm/sec, and preferably 0.01 nm/sec to 1 nm/sec. The film thickness of the organic semiconductor layer formed of the organic material is usually 1 nm to 10 µm, preferably 5 nm to 5 µm, and more preferably 10 nm to 3 µm.

Instead of the deposition method for heating and evaporating the organic material for forming a semiconductor layer, and applying the organic material to the substrate, a sputtering method for colliding accelerated ions of argon or the like against the target of the material to knock the material atoms out of the target and applying the material onto the substrate may be used.

The semiconductor material in the present invention is an organic compound, and a relatively low molecular compound. Accordingly, such a vacuum process can be preferably used. Such a vacuum process needs a slightly expensive facility, but has advantages such as excellent film forming properties and easy formation of a uniform film.

Meanwhile, the present invention can also use the solution process, namely, a coating method suitably. The method will be described. The semiconductor material containing the heterocyclic compound represented by the compound (1) in the present invention can be dissolved or dispersed in an organic solvent. Practical semiconductor properties can be obtained by the solution process. The production method using a coating method does not need to provide a vacuum or high temperature environment during production. For this reason, the production method is advantageous because a field effect transistor having a large area can be attained at low cost.

First, the heterocyclic compound represented by the compound (1) is dissolved or dispersed in a solvent to prepare an ink for creating a semiconductor device. The solvent used at this time is not particularly limited as long as the compound can be dissolved or dispersed in the solvent to form a film on the substrate. The solvent is preferably an organic solvent. Specifically, halogenohydrocarbon solvents such as chloroform, methylene chloride, and dichloroethane; alcohol solvents such as methanol, ethanol, isopropyl alcohol, and butanol; fluorinated alcohol solvents such as octafluoropentanol and pentafluoropropanol; ester solvents such as ethyl acetate, butyl acetate, ethyl benzoate, and diethyl carbonate; aromatic hydrocarbon solvents such as toluene, hexylbenzene, xylene, mesitylene, chlorobenzene, dichlorobenzene, methoxybenzene, chloronaphthalene, methylnaphthalene, and tetrahydronaphthalene; ketone solvents such as acetone, methyl ethyl ketone, methyl isobutyl ketone, cyclopentanone, and cyclohexanone; amide solvents such as dimethylformamide, dimethylacetamide, and N-methyl pyrrolidone; ether solvents such as tetrahydrofuran, diisobutyl ether, diphenyl ether; and hydrocarbon solvents such as octane, decane, decalin, and cyclohexane can be used, for example. These can be used singly, or can be used by mixing.

For improvement in the film forming properties of the semiconductor layer or doping described later, for example, additives and other semiconductor materials can be mixed.

Examples of these additives include various additives depending on the function required such as conductive, semiconductive, and insulative high-molecular compounds and low-molecular compounds, a dopant, a dispersant, a surfactant, a leveling agent, and a surface tension adjuster.

The concentration of the total amount of the heterocyclic compound represented by the compound (1) or a mixture thereof in the ink depends on the kind of solvents or the film thickness of the semiconductor layer to be created, and is usually approximately 0.001% to 50%, and preferably approximately 0.01% to 20%.

In use of the ink, the semiconductor material containing the heterocyclic compound represented by the compound (1) or the like is dissolved or dispersed in the solvent, and a heat dissolution treatment is performed when necessary. Further, the obtained solution is filtered using a filter or the like to remove a solid content such as impurities. Thereby, an ink for creating a semiconductor device is obtained. Use of such an ink improves the film forming properties of the semiconductor layer, and is preferable for creation of the semiconductor layer.

The thus-prepared ink for creating a semiconductor element is applied onto the substrate (exposed portions of the insulator layer, the source electrode, and the drain electrode).

For the application method, coating methods such as casting, spin coating, dip coating, blade coating, wire bar coating, and spray coating; printing methods such as inkjet printing, screen printing, offset printing, and relief printing; a soft lithography method such as a microcontact printing method; and a method using these in combination can be used.

Further, as a method similar to the application method, a Langmuir-Blodgett method in which a single-molecular film of the semiconductor layer created by dropping the ink on the surface of water is transferred onto a substrate and laminated, a method in which a liquid crystal material or a molten material is sandwiched by two substrates, and introduced into the gap between the substrates using a capillary phenomenon, and the like can also be used.

The film thickness of the organic semiconductor layer created by the method is preferably thinner in the range in which the function is not impaired. A thicker film thickness may cause larger leakage current. The film thickness of the organic semiconductor layer is usually 1 nm to 10 μm, preferably 5 nm to 5 μm, and more preferably 10 nm to 3 μm.

The thus-formed semiconductor layer (see (5) of FIG. 2) can be subjected to a post treatment to further improve the properties. For example, the semiconductor properties can be improved or stabilized by a heat treatment. The reason is thought as follows: for example, strain in the film caused during film formation is relaxed by the heat treatment, pin holes and the like reduce, and arrangement and orientation in the film can be controlled. In creation of the field effect transistor of the present invention, the heat treatment is effective in improvement in properties. The heat treatment is performed by heating the substrate after the semiconductor layer is formed. The temperature of the heat treatment is not particularly limited. The temperature is usually approximately room temperature to 200° C. The heat treatment time at this time is not particularly limited, and is usually 1 minute to 24 hours. The atmosphere at this time may be in the air, or may be under an inert atmosphere of nitrogen or argon, for example.

As other post treatment methods for the semiconductor layer, a treatment with an oxidizing or reducing gas such as oxygen and hydrogen or an oxidizing or reducing liquid can be performed to induce change in the properties by oxidation or reduction. This treatment is often used to increase or decrease the carrier density in the film, for example.

The properties of the semiconductor layer can be changed using a method called doping by adding a slight amount of an element, an atomic group, a molecule, or a polymer to the semiconductor layer. For example, acids such as oxygen, hydrogen, hydrochloric acid, sulfuric acid, and sulfonic acid; Lewis acids such as $PF_5$, $AsF_5$, and $FeCl_3$; halogen atoms such as iodine; metal atoms such as sodium and potassium; and the like can be used for doping. The semiconductor layer can be doped by contacting the semiconductor layer with these gases, immersing the semiconductor layer in the solution thereof, or performing an electrochemical doping treatment on the semiconductor layer. Doping with these dopants may be performed not after creation of the semiconductor layer. These dopants can be added during synthesis of the semiconductor material. In the process for creating the semiconductor layer using the ink for creating a semiconductor element, these dopants can be added to the ink. Further, these dopants can be added during the step of forming a precursor thin film disclosed in Patent Literature 2, for example. A material used for doping can be added to the material for forming the semiconductor layer in deposition to perform co-evaporation, or can be mixed with the ambient atmosphere during creation of the semiconductor layer (the semiconductor layer is created under the environment in which a doping material exists). Further, doping can be performed by accelerating ions in vacuum and colliding the ions against the film.

The doping effects are changes in electric conductivity caused by an increased or decreased carrier density, changes in the polarity of the carrier (p type, n type), and changes in the Fermi level, for example. Such doping is often used particularly in the semiconductor elements using an inorganic material such as silicon.

(Protective Layer)

Advantageously, formation of the protective layer 7 on the organic semiconductor layer can minimize the influence of the outside air, and stabilize the electrical properties of the organic field effect transistor (see (6) of FIG. 2). For the protective layer material, the materials above are used.

The protective layer 7 can use any film thickness according to the purpose. The film thickness is usually 100 nm to 1 mm.

A variety of methods can be used in formation of the protective layer. When the protective layer is formed of a resin, a method in which a resin solution is applied and dried to form a resin film; a method in which a resin monomer is applied or deposited, and polymerized; and the like can be used, for example. Further, a crosslinking treatment may be performed after film formation. When the protective layer is formed of an inorganic substance, a formation method using a vacuum process such as a sputtering method and a deposition method, or a formation method using a solution process such as a sol-gel method can be used, for example.

In the field effect transistor of the present invention, the protective layer can be provided on the organic semiconductor layer, and when necessary between the layers. These protective layers may be effective in stabilizing the electrical properties of the organic field effect transistor.

The present invention uses the organic material as the semiconductor material, and enables production by the process at a relatively low temperature. Consequently, flexible materials such as plastic plates and plastic films can be used as the substrate although these flexible materials cannot be used under the high temperature condition. As a result, the present invention enables production of an element which is light, highly flexible, and difficult to break, and such an element can be used as a switching element of an active matrix for displays, and the like. Examples of the displays include liquid crystal displays, polymer dispersed liquid crystal displays, electrophoretic displays, EL displays, electrochromic displays, and particle rotation displays.

The field effect transistor of the present invention can also be used as digital elements such as memory circuit elements, signal driver circuit elements, signal processing circuit elements and analog elements. Further, a combination of these enables creation of IC cards and IC tags. Further, the field effect transistor of the present invention can change the properties according to an external stimulus such as a chemical substance, and therefore can also be used as an FET sensor.

The operating properties of the field effect transistor are determined according to the carrier mobility and electric conductivity of the semiconductor layer, the capacitance of the insulator layer, the configuration of the element (distance and width between the source and drain electrodes, the film thickness of the insulator layer, and the like), and the like. A preferable semiconductor material used in the field effect transistor is those having a higher carrier mobility when the semiconductor layer is formed of the semiconductor material. The heterocyclic compound represented by the compound (1) in the present invention has excellent film forming properties. Further, the pentacene derivative and the like are compound unstable and difficult to handle because these compounds are decomposed by moisture contained in the air or the like. When the heterocyclic compound represented by the compound (1) of the present invention is used as the semiconductor material, however, the heterocyclic compound represented by the compound (1) exhibits advantages in that stability is high and life is long even after creation of the semiconductor layer. Moreover, the transistor having the semiconductor layer formed of the heterocyclic compound represented by the compound (1) has a low threshold voltage. For this reason, driving voltage reduces in practical use, and power consumption is smaller than that of the conventional transistor, enabling energy saving. For example, the transistor of the present invention is effective in portable displays and the like in which drive for a longer time is required during using a rechargeable battery. Moreover, a lower threshold voltage reduces energy consumption. Further, a lower threshold voltage reduces the barrier against injection of charges from the electrode to the semiconductor film. It is expected that such a lower threshold voltage also is effective in improving the durability of the semiconductor element and the semiconductor device itself having the semiconductor element.

EXAMPLES

Hereinafter, the present invention will be more specifically described using Examples, but the present invention will not be limited to these examples. In Examples, "parts" indicate "parts by mass" and "%" indicates "% by mass" unless otherwise specified. The reaction temperatures described in Examples are inner temperature of reaction systems unless otherwise specified.

The formulas of a variety of compounds obtained in Synthesis Examples were determined when necessary by performing a variety of measurements of mp (melting point), NMR (1H, 13C), IR (infrared absorption spectrum), MS (mass spectrometry spectrum), and element analysis. The measurement apparatuses are shown below.

mp: Yanagimoto micro melting point measurement apparatus MP-S3
NMR: JEOL Lambda 400 spectrometer
IR: SHIMADZU Fourier transform infrared spectrophotometer IR Prestige-21
MS spectrum: Shimadzu QP-5050A
element analysis: Parkin Elmer 2400CHN element analyzer First, synthesis of compounds will be specifically described.

Example 1

Synthesis of 6-n-decyl-2-methoxynaphthalene compound (compound (3)-64)

Example 1-1

Synthesis of 2-decanoyl-6-methoxynaphthalene

Under a nitrogen atmosphere, 2-methoxynaphthalene (64 g, 0.41 mol) easily available from a reagent manufacturer was dissolved in nitromethane (150 ml) dried with a molecular sieve 3A. Under an ice bath, aluminum chloride (80 g, 0.60 mol) was added. Subsequently, decanoyl chloride (92 ml, 0.45 mol) was dropped into the solution under the ice bath. The solution was stirred under room temperature for 5 hours, and water (100 ml) was dropped into the solution under the ice bath. The reaction solution was extracted with methylene chloride (200 ml×4), and the obtained organic layer was washed with water (100 ml×3). The organic layer was dried with anhydrous magnesium sulfate, and filtered. Then, the solvent was distilled away under reduced pressure. The obtained yellow solid was recrystallized from hexane to obtain 2-decanoyl-6-methoxynaphthalene (102 g, 82%) as a white solid.

$^1$H-NMR (270 MHz, CDCl$_3$) δ 0.88 (t, 2H, J=6.5 Hz), 1.18-1.49 (br, 16H), 1.78 (m, 2H), 3.07 (t, 2H, J=7.4 Hz), 3.95 (s, 3H), 7.16 (d, 1H, J=2.6 Hz), 7.20 (dd, 1H, J=8.9 Hz, 2.3 Hz), 7.77 (d, 1H, J=8.6 Hz), 7.86 (d, 1H, J=8.9 Hz), 8.01 (dd, 1H, J=8.6 Hz, 1.6 Hz), 8.40 (s, 1H); EIMS (70 eV) m/z=312 (M$^+$)

Example 1-2

Synthesis of 6-n-decyl-2-hydroxynaphthalene

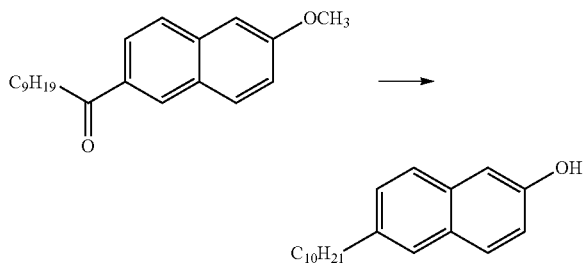

Under a nitrogen atmosphere, 2-decanoyl-6-methoxynaphthalene (9.4 g, 30 mmol) and potassium hydroxide (67 g, 1.2 mol) were dissolved in hydrazine monohydrate (70 ml, 1.4 mol) and diethylene glycol (200 ml). The solution was refluxed for 17 hours, and water (36 ml) was added. Under a stream of nitrogen, the solution was distilled to distill away an excessive amount of hydrazine and water. Further, the solution was refluxed under a nitrogen atmosphere for 41 hours. Subsequently, while using an ice bath, the solution was cooled by putting ice into the reaction solution, hydrochloric acid was slowly added until the solution became neutral. The reaction solution was extracted with ether (100 ml×3), and the obtained organic layer was washed with saturated saline water (100 ml×5). The organic layer was dried with anhydrous magnesium sulfate, and filtered. Then, the solvent was distilled away under reduced pressure. The obtained brown solid was recrystallized from hexane to obtain 6-decyl-2-hydroxynaphthalene (7.3 g, 90%) as a white solid.

$^1$H-NMR (270 MHz, CDCl$_3$) δ 0.88 (t, 2H, J=6.5 Hz), 1.18-1.43 (br, 17H), 1.59-1.75 (br, 3H), 2.72 (t, 2H, J=7.7 Hz), 4.99 (s, 1H), 7.07 (dd, 1H, J=8.9 Hz, 2.6 Hz), 7.11 (d, J=2.3 Hz), 7.28 (dd, 1H, J=8.4 Hz, 1.8 Hz), 7.53 (br, 1H), 7.60 (d, 1H, J=8.6 Hz), 7.68 (d, 1H, J=8.9 Hz); EIMS (70 eV) m/z=284 (M$^+$)

Example 1-3

Synthesis of 6-n-decyl-2-methoxynaphthalene (compound (3)-64)

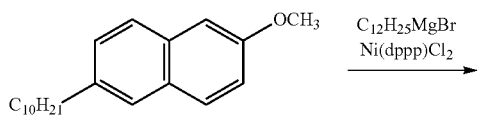

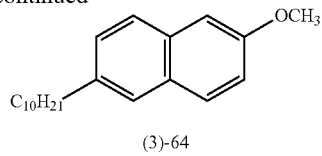

(3)-64

Under a nitrogen atmosphere, 6-n-decyl-2-hydroxynaphthalene (5.68 g, 20 mmol) and a THF (200 ml) solution of 55% NaH (oil dispersion, 880 mg, 20 mmol) were stirred at room temperature for 40 minutes. CH$_3$I (1.48 ml, 24 mmol) was added to the mixed solution, and the mixed solution was heated under reflux for 12 hours. Water (20 ml) was added to the mixture at 0° C., and the mixture was washed with saline water. Organic layers were combined, and dried with MgSO$_4$, and condensed with an evaporator. The condensed solution was recrystallized from methanol to obtain 6-n-decyl-2-methoxynaphthalene (compound (3)-64) (5.0 g, 85%) as a white solid.

$^1$H-NMR (270 MHz, CDCl$_3$) δ 0.88-1.70 (aliphatic), 2.72 (t, 2H, J=7.2 Hz), 3.90 (s, 3H), 7.09-7.13 (m, 2H), 7.29 (dd, 1H, J=8.2 Hz, 1.6 Hz), 7.53 (br, 1H), 7.64 (d, 1H, J=2.0 Hz), 7.68 (d, 1H, J=3.3 Hz); EIMS (70 eV) m/z=298 (M$^+$)

Example 2

Synthesis of 6-n-decyl-2-methoxynaphthalene (compound (3)-64) by another method

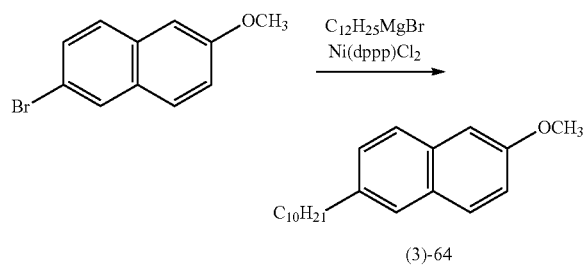

(3)-64

A THF solution of n-decyl magnesium bromide (prepared as a THF (2 ml) solution of n-decyl bromide (2.2 ml, 11 mmol) and Mg (292 mg, 12 mmol)) was added to 6-bromo-2-methoxynaphthalene (2.37 g, 10 mmol) easily available from a reagent manufacturer and a THF (10 ml) solution of Ni(dppp)Cl$_2$ (271 mg, 0.5 mmol), and the mixture was heated under reflux for 19 hours. After cooling, the mixed solution was diluted with water (10 ml), and non-reacted Mg was filtered out. The filtered solution was extracted with ether (5 ml×3). The extracted organic phases were collected (10 ml×3), and dried with MgSO$_4$, and condensed with an evaporator. The condensed organic phase was recrystallized with hexane to obtain 6-n-decyl-2-methoxynaphthalene (compound (3)-64) as a light yellow solid.

mp 48.6 to 49.3° C.; $^1$H NMR (270 MHz, CDCl$_3$) δ 0.87 (t, J=6.7 Hz, 3H), 1.25-1.32 (m, 14H), 1.67 (quint, J=7.7 Hz, 2H), 2.72 (t, J=7.2 Hz, 2H), 3.90 (s, 3H), 7.09-7.13 (m, 2H), 7.29 (dd, J=8.2 Hz, 1.6 Hz, 1H), 7.53 (brs, 1H), 7.64 (d, J=2.0 Hz, 1H), 7.68 (d, J=3.3 Hz, 1H); $^{13}$C NMR (100 MHz, CDCl$_3$); δ 14.1, 22.7, 29.4, 29.6 (×3), 31.5, 31.9, 35.9, 45.2, 105.6, 118.5, 126.1, 126.0, 127.9, 128.9, 129.1, 132.9, 138.1, 157.0; EIMS (70 eV) m/z=298 (M$^+$); Anal. Calcd for C$_{21}$H$_{30}$O: C, 84.51; H, 10.13%. Found: C, 84.62; H, 10.41%.

Example 3

Synthesis of 7-decyl-2-methoxynaphthalene (compound (3)-12)

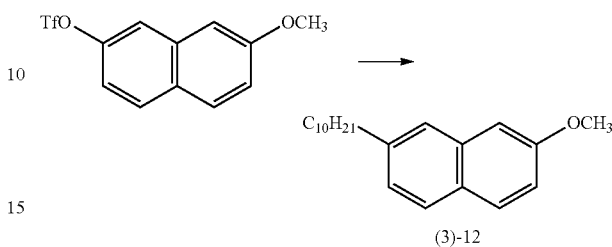

(3)-12

1-Decyne (1.2 g, 6.5 mmol), PdCl$_2$(PPh$_3$)$_2$ (0.12 g, 0.16 mmol), CuI (13 mg, 0.065 mmol), and triethylamine (14 ml, 9.8 mmol) were added to a THF (20 ml) solution of 7-methoxy-2-naphthyltrifluoromethane sulfonate (1.0 g, 3.3 mmol). The solution was mixed at room temperature for 4 hours, and diluted with water (30 ml). The solution was made acidic with diluted hydrochloric acid (2 M), and extracted with dichloromethane (30 ml×3). The extracted solution was washed with water (100 ml×3), and dried with MgSO$_4$. The solution was condensed, and subjected to column chromatography (silica gel, developed with dichloromethane) to obtain 7-decyn-1-yl-2-methoxynaphthalene as a light yellow oil product. The obtained 7-decyn-1-yl-2-methoxynaphthalene (2.8 mmol) and a THF (13 ml) of 10% Pd/C (0.16 g) were placed in a 50 ml round-bottomed flask. Under a hydrogen atmosphere, the solution was stirred until the reaction was completed (approximately 12 hours) while the reaction was tracked using TLC. When the reaction was completed, a catalyst was filtered out, and the filtrate was condensed. The condensed solution was refined by column chromatography (silica gel, developed with dichloromethane) to obtain 7-decyl-2-methoxynaphthalene (compound (3)-12) (0.80 g, 82%).

mp 29.9 to 30.8° C.; $^1$H NMR (270 MHz, CDCl$_3$) δ 0.88 (t, J=7.0 Hz, 3H), 1.27-1.171 (m, 16H), 2.74 (t, J=7.7 Hz, 2H), 3.92 (s, 3H), 7.07 (dd, J=9.7, 2.4 Hz, 1H), 7.09 (s, 1H), 7.19 (dd, J=8.3, 1.7 Hz, 1H), 7.51 (s, 1H), 7.68 (d, J=8.3 Hz, 1H), 7.70 (d, J=9.7 Hz, 1H); $^{13}$C NMR (100 MHz, CDCl$_3$); δ 14.4, 23.0, 29.6, 29.7, 29.9, 30.2 (×2), 31.7, 32.3, 36.5, 55.6, 105.8, 118.1, 125.6, 125.7, 127.8 (×2), 129.4, 135.1, 141.4, 158.0; EIMS (70 eV) m/z=298 (M$^+$); Anal. Calcd for C$_{21}$H$_{30}$O: C, 84.51; H, 10.13%. Found: C, 84.48; H, 10.44%.

Example 4

Synthesis of 7-phenyl-2-methoxynaphthalene (compound (3)-22)

n-Hydrate of potassium phosphate (34 g, 0.16 mol) and phenylboric acid (3.7 g, 30 mmol) were added to a DMF (350 ml) solution of 7-methoxy-2-naphthyltrifluoromethane sulfonate (6.1 g, 20 mmol). The solution was bubbled with nitrogen for 30 minutes to perform replacement with nitrogen. PdCl$_2$(PPh$_3$)$_2$ (0.71 g, 1 mmol) was added, and the solution was heated for 4 hours at 80° C. A saturated ammonium chloride aqueous solution (500 ml) was added to the obtained mixture. Crystals deposited by this operation was filtered out, washed with water (100 ml×3), and dried with an electric dryer (60° C.). The crude product was refined by column chromatography (silica gel, developed with dichloromethane) to obtain 7-phenyl-2-methoxynaphthalene (compound (3)-22), 3.4 g).

yield of 73%; yellow crystal (recrystallized with hexane); mp 65.4 to 66.3° C.; $^1$H NMR (400 MHz, CDCl$_3$) δ 3.95 (s, 3H), 7.15 (dd, J=8.9, 2.5 Hz, 1H), 7.38 (tt, J=7.4, 1.2 Hz, 1H), 7.46-7.50 (m, 2H), 7.60 (dd, J=8.5, 1.6 Hz, 1H), 7.70-7.72 (m, 2H), 7.76 (d, J=8.9 Hz, 1H), 7.84 (d, J=8.5 Hz, 1H), 7.95 (d, J=1.6 Hz, 1H); $^{13}$C NMR (100 MHz, CDCl$_3$) δ 55.7, 106.5, 119.1, 123.7, 125.1, 127.7, 127.8, 128.5 •(×2), 129.2, 129.5, 135.2, 139.5, 141.7, 158.4; EI-MS, m/z=234 (M$^+$); Anal. Calcd for C$_{17}$H$_{14}$O: C, 87.15; H, 6.02%.

Found: C, 87.23; H, 6.03%.

Example 5

Synthesis of 6-phenyl-2-methoxynaphthalene (compound (3)-31)

A target product 6-phenyl-2-methoxynaphthalene (compound (3)-31) was obtained at a yield of 90% from 6-bromo-2-methoxynaphthalene (easily available from a reagent manufacturer) and phenylboric acid by the same operation as that in the method for synthesizing 7-phenyl-2-methoxynaphthalene according to Example 4.

mp 135.4 to 136.4° C.; $^1$H NMR (400 MHz, CDCl$_3$) δ 3.95 (s, 3H), 7.17 (s, 1H), 7.19 (dd, J=7.9, 2.5 Hz, 1H), 7.38 (tt, J=7.4, 1.2 Hz, 1H), 7.45-7.49 (m, 2H), 7.72 (dd, J=8.5, 1.8 Hz, 1H), 7.70-7.72 (m, 2H), 7.80 (d, J=7.9 Hz, 1H), 7.82 (d, J=7.9 Hz, 1H), 7.98 (d, J=1.8 Hz, 1H); EI-MS, m/z=234 (M$^+$); Anal. Calcd for C$_{17}$H$_{14}$O: C, 87.15; H, 6.02%. Found: C, 86.86; H, 5.94%.

Example 6

Synthesis of 6-tolyl-2-methoxynaphthalene (compound (3)-32)

6-Tolyl-2-methoxynaphthalene (compound (3)-32, 33.3 g, yield of 82%) was obtained by the same operation as that in the method for synthesizing 7-phenyl-2-methoxynaphthalene according to Example 4 except that 6-bromo-2-methoxynaphthalene (38.9 g, 0.16 mol) was used instead of 7-methoxy-2-naphthyltrifluoromethane sulfonate and 4-methylphenylboric acid (25.0 g, 0.21 mol) was used instead of 4-phenylboric acid.

EI-MS, m/z=248 (M$^+$)

Example 7

Synthesis of 7-tolyl-2-methoxynaphthalene (compound (3)-23)

7-Tolyl-2-methoxynaphthalene (compound (3)-23, 22.5 g, yield of 96%) was obtained using 7-methoxy-2-naphthyltrifluoromethane sulfonate (30.63 g, 0.10 mol) and 4-methylphenylboric acid (16.12 g, 0.12 mol) by the same operation as that in the method for synthesizing 7-phenyl-2-methoxynaphthalene according to Example 4.

EI-MS, m/z=248 (M$^+$)

Example 8

Synthesis of 6-biphenyl-2-methoxynaphthalene (compound (3)-33)

6-Biphenyl-2-methoxynaphthalene (compound (3)-33, 24.8 g, yield of 84%) was obtained by the same operation as that in the method for synthesizing 7-phenyl-2-methoxynaphthalene according to Example 4 except that 6-bromo-2-methoxynaphthalene (22.5 g, 94.8 mmol) was used instead of 7-methoxy-2-naphthyltrifluoromethane sulfonate and 4-biphenylboric acid (23.48 g, 119 mmol) was used.

EI-MS, m/z=310 (M$^+$)

Example 9

Synthesis of 7-biphenyl-2-methoxynaphthalene (compound (3)-24)

7-Biphenyl-2-methoxynaphthalene (compound (3)-24, 21.9 g, yield of 74%) was synthesized by the same operation as that in the method for synthesizing 7-phenyl-2-methoxynaphthalene according to Example 4 using 7-methoxy-2-naphthyltrifluoromethane sulfonate (29.05 g, 94.8 mmol) and 4-biphenylboric acid (23.48 g, 119 mmol).

EI-MS, m/z=310 (M$^+$)

Example 10

Synthesis of 7-butyl-2-methoxynaphthalene (compound (3)-04)

Using 7-methoxy-2-naphthyltrifluoromethanesulfonate (30.63 g, 0.10 mol) and butyne gas (a product manufactured by TOKYO CHEMICAL INDUSTRY CO., LTD., 100 g, large excess), 7-butyn-1-yl-2-methoxynaphthalene was synthesized by the same operation as that in the method for synthesizing 7-decyl-2-methoxynaphthalene according to Example 3, and subjected to column chromatography (silica gel, developed with a mixture of toluene and hexane) to obtain a light yellow oil product of 7-butyn-1-yl-2-methoxynaphthalene (18.1 g, yield of 56%). The obtained 7-butyn-1-yl-2-methoxynaphthalene (total amount) was subjected to catalytic reduction in toluene (275 ml) under a hydrogen atmosphere by adding 10% Pd/C (1.83 g). The obtained product was subjected to column chromatography (silica gel, developed with a mixture of toluene and hexane) to obtain 7-butyl-2-methoxynaphthalene (compound (3)-04, 17.80 g, yield of 97%).

EI-MS, m/z=214 (M$^+$)

Example 11

Synthesis of 7-hexyl-2-methoxynaphthalene (compound (3)-08)

Using 7-methoxy-2-naphthyltrifluoromethanesulfonate (30.63 g, 0.10 mol) and 1-hexyne (10.27 g, 0.125 mol), 7-hexyn-1-yl-2-methoxynaphthalene was synthesized by the same operation as that in the method for synthesizing 7-decyl-2-methoxynaphthalene according to Example 3, and subjected to column chromatography (silica gel, developed with a mixture of toluene and hexane) to obtain a light yellow oil product of 7-hexyn-1-yl-2-methoxynaphthalene (20.5 g, yield of 86%). The obtained 7-hexyn-1-yl-2-methoxynaphthalene (total amount) was subjected to catalytic reduction in toluene (275 ml) under a hydrogen atmosphere by adding 10% Pd/C (1.83 g). The obtained product was subjected to column chromatography (silica gel, developed with a mixture of toluene and hexane) to obtain 7-hexyl-2-methoxynaphthalene (compound (3)-08, 20.70 g, yield of 99%).

EI-MS, m/z=242 (M$^+$)

Example 12

Synthesis of 7-octyl-2-methoxynaphthalene (compound (3)-10)

Using 7-methoxy-2-naphthyltrifluoromethanesulfonate (30.63 g, 0.10 mol) and 1-octyne (13.78 g, 0.125 mol), 7-octyn-1-yl-2-methoxynaphthalene was synthesized by the same operation as that in the method for synthesizing 7-decyl-2-methoxynaphthalene according to Example 3, and subjected to column chromatography (silica gel, developed with a mixture of toluene and hexane) to obtain a light yellow oil product of 7-octyn-1-yl-2-methoxynaphthalene (22.9 g, yield of 86%). The obtained 7-octyn-1-yl-2-methoxynaphthalene (total amount) was subjected to catalytic reduction in toluene (213 ml) under a hydrogen atmosphere by adding 10% Pd/C (2.13 g). The obtained product was subjected to column chromatography (silica gel, developed with a mixture of toluene and hexane) to obtain 7-octyl-2-methoxynaphthalene (compound (3)-10, 24.30 g, yield of 90%).

EI-MS, m/z=270 ($M^+$)

Example 13

Synthesis of 7-dodecyl-2-methoxynaphthalene (compound (3)-14)

Using 7-methoxy-2-naphthyltrifluoromethanesulfonate (30.63 g, 0.10 mol) and 1-dodecyne (20.79 g, 0.125 mol), 7-dodecyn-1-yl-2-methoxynaphthalene was synthesized by the same operation as that in the method for synthesizing 7-decyl-2-methoxynaphthalene according to Example 3, and subjected to column chromatography (silica gel, developed with a mixture of toluene and hexane) to obtain a light yellow oil product of 7-dodecyn-1-yl-2-methoxynaphthalene (32.0 g, quantitative). The obtained 7-dodecyn-1-yl-2-methoxynaphthalene (total amount) was subjected to catalytic reduction in toluene (316 ml) under a hydrogen atmosphere by adding 10% Pd/C (2.11 g). The obtained product was subjected to column chromatography (silica gel, developed with a mixture of toluene and hexane) to obtain 7-dodecyl-2-methoxynaphthalene (compound (3)-14, 31.10 g, yield of 96%).

EI-MS, m/z=326 ($M^+$)

Examples in which the compound (4) was derived from the compound (3) will be shown below.

Example 14

Synthesis of 6-n-decyl-3-methylthio-2-methoxynaphthalene (compound (4)-64)

A hexane solution of 1.57 Mn—BuLi (28 ml, 44 mmol) was added to a THF (100 ml) solution of 6-n-decyl-2-methoxynaphthalene (compound (3)-64) (12 g, 40 mmol) at −78° C., and the solution was stirred at room temperature for 1 hour. Dimethyl disulfide (4.4 ml, 48 mmol) was added to the solution at −78° C., and the solution was stirred at room temperature for 18 hours. The reaction solution was added to a saturated ammonium chloride aqueous solution (50 ml), and extracted with ether (30 ml×3). The extracted solutions obtained by repeating the extraction 3 times were collected, washed with a saturated saline water (30 ml×3), and dried with $MgSO_4$. The dried product was condensed with an evaporator to obtain 6-n-decyl-3-methylthio-2-methoxynaphthalene (compound (4)-64) (15.2 g, quantitative) as a yellow oil. The compound can be used in the subsequent reaction without performing further refining.

$^1$H NMR (400 MHz, $CDCl_3$) δ 0.87 (t, J=6.7 Hz, 3H), 1.25-1.32 (m, 14H), 1.67 (quint, J=7.7 Hz, 2H), 2.72 (t, J=7.2 Hz, 2H), 2.53 (s, 3H), 2.72 (t, J=7.8 Hz, 2H), 3.98 (s, 3H), 7.05 (s, 1H), 7.23 (d, J=6.8 Hz, 1H), 7.40 (s, 1H), 7.48 (s, 1H), 7.62 (d, J=8.8 Hz, 1H); $^{13}$C NMR (100 MHz, $CDCl_3$); δ 14.1, 14.6, 22.7, 29.4, 29.6 (×3), 31.5, 31.9, 36.0, 55.8, 104.6, 122.9, 125.0, 126.3, 127.0, 129.4, 130.4, 138.7, 154.0; EIMS (70 eV) m/z=344 ($M^+$). Anal Calcd for $C_{22}H_{32}OS$: C, 76.69; H, 9.36%. Found: C, 76.83; H, 9.66%.

Example 15

Synthesis of 7-decyl-3-methylthio-2-methoxynaphthalene (compound (4)-12)

7-Decyl-3-methylthio-2-methoxynaphthalene (compound (4)-12) was synthesized from 7-decyl-2-methoxynaphthalene (compound (3)-12) and dimethyl disulfide by the same method as that in Example 14 (yield of 93%, recrystallized from hexane to obtain yellow crystals).

mp 49.5 to 50.4° C.; $^1$H NMR (500 MHz, $CDCl_3$) δ 0.87 (t, J=6.8 Hz, 3H), 1.24-1.69 (m, 16H), 2.53 (s, 3H), 2.72 (t, J=7.8 Hz, 2H), 3.99 (s, 3H), 7.03 (s, 1H), 7.18 (d, J=8.4 Hz, 1H), 7.44 (s, 1H), 7.48 (s, 1H), 7.62 (d, J=8.4 Hz, 1H); $^{13}$CNMR (126 MHz, $CDCl_3$); δ 14.5, 15.1, 23.0, 29.7 (×2), 29.9 (×2), 30.0, 31.7, 32.2, 36.4 56.2, 104.8, 123.7, 125.4, 126.0, 126.6, 128.0, 128.6, 132.7, 140.6, 155.0; EIMS (70 eV) m/z=344 ($M^+$). Anal Calcd for $C_{22}H_{32}OS$: C, 76.69; H, 9.36%. Found: C, 76.83; H, 9.66%.

Example 16

3-methylthio-7-phenyl-2-methoxynaphthalene (compound (4)-22)

3-Methylthio-7-phenyl-2-methoxynaphthalene (compound (4)-22) was obtained by the same method as that in Example 14 from 7-phenyl-2-methoxynaphthalene (compound (3)-22) and dimethyl disulfide at a yield of 77% (recrystallized from hexane to obtain yellow crystals).

mp 149 to 150° C.; $^1$H NMR (400 MHz, $CDCl_3$) δ 2.56 (s, 3H), 4.03 (s, 3H), 7.15 (s, 1H), 7.38 (tt, J=7.4, 1.3 Hz, 1H), 7.46-7.49 (m, 2H), 7.47 (s, 1H), 7.61 (dd, J=8.4, 1.8 Hz, 1H), 7.70-7.72 (m, 2H), 7.77 (d, J=8.5 Hz, 1H), 7.92 (d, J=1.8 Hz, 1H); EI-MS, m/z=280 ($M^+$); Anal. Calcd for $C_{18}H_{16}OS$: C, 77.11; H, 5.75%. Found: C, 77.05; H, 5.64%.

Example 17

Synthesis of 3-methylthio-6-phenyl-2-methoxynaphthalene (compound (4)-31)

3-Methylthio-6-phenyl-2-methoxynaphthalene (compound (4)-31) was synthesized from 6-phenyl-2-methoxynaphthalene (compound (3)-31) and dimethyl disulfide by the same method as that in Example 14.

mp 124 to 125.2° C.; $^1$H NMR (400 MHz, $CDCl_3$) δ 2.56 (s, 3H), 4.02 (s, 3H), 7.11 (s, 1H), 7.36 (tt, J=7.4, 1.3 Hz, 1H), 7.45-7.50 (m, 2H), 7.53 (s, 1H), 7.66 (dd, J=8.5, 1.6 Hz, 1H), 7.69-7.72 (m, 2H), 7.77 (d, J=8.5 Hz, 1H), 7.92 (d, J=1.6 Hz, 1H); $^{13}$C NMR (100 MHz, $CDCl_3$) δ 14.9, 56.3, 104.8, 123.7, 124.8, 125.4, 127.3, 127.4, 127.6, 129.2, 129.9, 130.6, 131.6, 137.2, 141.6; EI-MS, m/z=280 ($M^+$); Anal. Calcd for $C_{18}H_{16}OS$: C, 77.11; H, 5.75%. Found: C, 77.22; H, 5.75%.

Example 18

Synthesis of 6-tolyl-3-methylthio-2-methoxynaphthalene (compound (4)-32)

6-Tolyl-3-methylthio-2-methoxynaphthalene (compound (4)-32, 19.22 g, 49%) was obtained from 6-tolyl-2-methoxynaphthalene (compound (3)-32, 33.3 g) and dimethyl disulfide by the same method as that in Example 14. The process can go to the subsequent reaction without performing further refining.
EI-MS, m/z=294 (M$^+$)

Example 19

Synthesis of 7-tolyl-3-methylthio-2-methoxynaphthalene (compound (4)-23)

7-Tolyl-3-methylthio-2-methoxynaphthalene was synthesized from 7-tolyl-2-methoxynaphthalene (compound (3)-23, 22.2 g, 89 mmol) by the same method as that in Example 14, and recrystallized from toluene to obtain a compound (compound (4)-23, 11.5 g, yield of 44%). The process can go to the subsequent reaction without performing further refining.
EI-MS, m/z=294 (M$^+$)

Example 20

Synthesis of 6-biphenyl-3-methylthio-2-methoxynaphthalene (compound (4)-33)

6-Biphenyl-3-methylthio-2-methoxynaphthalene (compound (4)-33, 22.3 g, 81%) was obtained from 6-biphenyl-2-methoxynaphthalene (compound (3)-33, 24.0 g) by the same method as that in Example 14. The process can go to the subsequent reaction without performing further refining.
EI-MS, m/z=356 (M$^+$)

Example 21

Synthesis of 7-biphenyl-3-methylthio-2-methoxynaphthalene (compound (4)-24)

7-Biphenyl-3-methylthio-2-methoxynaphthalene (compound (4)-24) was synthesized from 7-biphenyl-2-methoxynaphthalene (compound (3)-24, 21.5 g) by the same method as that in Example 14, and recrystallized from toluene to obtain a compound (4)-24 (16.0 g, yield of 65%). The process can go to the subsequent reaction without performing further refining.
EI-MS, m/z=356 (M$^+$)

Example 22

Synthesis of 7-butyl-3-methylthio-2-methoxynaphthalene (compound (4)-04)

7-Butyl-3-methylthio-2-methoxynaphthalene (compound (4)-04, 22.3 g, yield of 100%) was obtained from 7-butyl-2-methoxynaphthalene (compound (3)-04, 17.80 g, 83.1 mmol) by the same method as that in Example 14. The process can go to the subsequent reaction without performing further refining.
EI-MS, m/z=260 (M$^+$)

Example 23

Synthesis of 7-hexyl-3-methylthio-2-methoxynaphthalene (compound (4)-08)

7-Hexyl-3-methylthio-2-methoxynaphthalene (compound (4)-08, 24.7 g, quantitative) was obtained from 7-hexyl-2-methoxynaphthalene (compound (3)-08) by the same method as that in Example 14. The process can go to the subsequent reaction without performing further refining.
EI-MS, m/z=288 (M$^+$)

Example 24

Synthesis of 7-octyl-3-methylthio-2-methoxynaphthalene (compound (4)-10)

7-Octyl-3-methylthio-2-methoxynaphthalene (compound (4)-10, 27.09 g, yield of 95%) was obtained from 7-octyl-2-methoxynaphthalene (compound (3)-10) by the same method as that in Example 14. The process can go to the subsequent reaction without performing further refining.
EI-MS, m/z=316 (M$^+$)

Example 25

Synthesis of 7-dodecyl-3-methylthio-2-methoxynaphthalene (compound (4)-14)

7-Dodecyl-3-methylthio-2-methoxynaphthalene (compound (4)-14, 34.1 g, yield of 96%) was obtained from 7-dodecyl-2-methoxynaphthalene (compound (3)-14) by the same method as that in Example 14. The process can go to the subsequent reaction without performing further refining.
EI-MS, m/z=372 (M$^+$)

The following operation can perform on the substituent in the compound (4) to easily convert the compound (4) to a derivative having another substituent.

Synthesis Example 1

Synthesis of 6-decyl-3-methylthio-2-(trifluoromethanesulfonyloxy)naphthalene (compound (4)-81)

Synthesis Example 1-1

Synthesis of 6-decyl-3-methylthio-2-hydroxynaphthalene

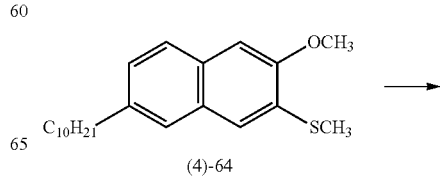

(4)-64

-continued

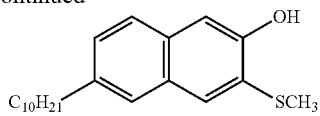

A dichloromethane (50 ml) solution of 6-decyl-3-methylthio-2-methoxynaphthalene (compound (4)-64) (28 g, 81 mmol) was added to a dichloromethane solution of BBr$_3$ (ca.2 M 70 ml, 140 mmol) at −78° C. The solution was stirred at room temperature for 12 hours. Ice (approximately 20 g) was added to the mixture. The reaction solution was extracted with dichloromethane (20 ml×3). The organic layers obtained by repeating the extraction three times were collected, washed with saturated saline water (30 ml×3), dried with MgSO$_4$, and condensed. The residue was refined by column chromatography (silica gel, developed at dichloromethane: hexane=1:1), and recrystallized with hexane to obtain 6-decyl-3-methylthio-2-hydroxynaphthalene (18.1 g, 72%) as white crystals.

mp 65.5 to 66.0° C.; $^1$H NMR (270 MHz, CDCl$_3$) δ 0.88 (t, J=6.7 Hz, 3H), 1.26-1.32 (m, 14H), 1.67 (quint, J=7.7 Hz, 2H), 2.41 (s, 3H), 2.71 (t, J=7.3 Hz, 2H), 6.57 (s, 1H), 7.28 (s, 1H), 7.28 (dd, J=8.2 Hz, 1.6 Hz, 1H), 7.48 (brs, 1H), 7.61 (d, J=8.6 Hz, 1H), 7.94 (s, 1H); $^{13}$C NMR (100 MHz, CDCl$_3$) δ 14.1, 19.9, 22.7, 29.3, 29.6 (×3), 31.4, 31.9, 35.9, 109.1, 124.1, 125.7, 126.3, 128.7, 129.1, 133.5 (×2), 138.5, 152.1; IR (KBr) ν 3402 cm$^{-1}$ (OH); EIMS (70 eV) m/z=330 (M$^+$); Anal. Calcd for C$_{21}$H$_{30}$OS: C, 76.31; H, 9.15%. Found: C, 76.34; H, 9.23%.

Synthesis Example 1-2

Synthesis of 6-decyl-3-methylthio-2-(trifluoromethanesulfonyloxy)naphthalene (compound (4)-81)

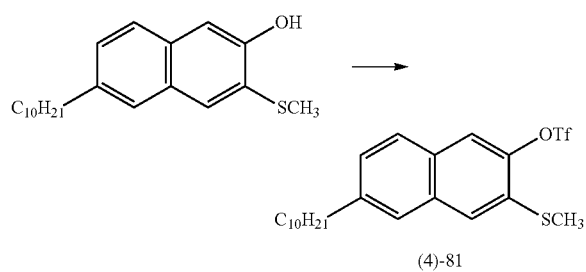

Trifluoromethanesulfonic anhydride (3 ml, 15 mmol) was added to a dichloromethane (50 ml) solution of the obtained 6-decyl-3-methylthio-2-hydroxynaphthalene (3.63 g, 10 mmol) and pyridine (2.5 ml, 30 mmol) at 0° C. This solution was stirred at room temperature for 25 minutes. Then, the mixture was diluted with water (20 ml), and hydrochloric acid (4 M, 20 ml) was added. The mixture was extracted with dichloromethane (30 ml×3). The organic phases obtained by repeating the extraction three times were collected, washed with saturated saline water (30 ml×3), dried with MgSO$_4$, and condensed to obtain 6-decyl-3-methylthio-2-(trifluoromethanesulfonyloxy)naphthalene (compound (4)-81) (4.89 g, 99%).

mp 42.0 to 42.9° C.; $^1$H NMR (270 MHz, CDCl$_3$) δ 0.88 (t, J=6.7 Hz, 3H), 1.26-1.32 (m, 14H), 1.68 (quint, J=7.7 Hz, 2H), 2.59 (s, 3H), 2.76 (t, J=7.3 Hz, 2H), 7.36 (dd, J=8.7 Hz, 1.8 Hz, 1H), 7.57 (brs, 1H), 7.63 (s, 1H), 7.68 (s, 1H), 7.72 (d, J=8.2 Hz, 1H); $^{13}$C NMR (100 MHz, CDCl$_3$) δ 14.1, 15.8, 22.7, 29.3 (×2), 29.5, 29.6 (×2), 31.2, 31.9, 36.1, 118.7 (q, J=319 Hz), 119.2, 125.2, 126.3, 127.7, 128.4, 129.4, 130.7, 133.0, 142.7, 144.8; IR (KBr) ν 1423, 1211 cm$^{-1}$ (—O—SO$_2$—); EIMS (70 eV) m/z=462 (M$^+$); Anal. Calcd for C$_{22}$H$_{29}$F$_3$O$_3$S$_2$: C, 57.12; H, 6.32%. Found C, 56.91; H, 6.15%.

Synthesis Example 2

Synthesis of 7-decyl-3-methylthio-2-(trifluoromethanesulfonyloxy)naphthalene (compound (4)-77)

Synthesis Example 2-1

Synthesis of 7-decyl-3-methylthio-2-hydroxynaphthalene

7-Decyl-3-methylthio-2-methoxynaphthalene (compound (4)-12) synthesized in Example 15 was demethylated by the operation in (Synthesis Example 1-1) to obtain 7-decyl-3-methylthio-2-hydroxynaphthalene.

yield of 85%; yellow crystal (recrystallized with hexane); mp 64.4 to 65.4° C.; $^1$H NMR (400 MHz, CDCl$_3$) δ 0.88 (t, J=6.9 Hz, 3H), 1.24-1.72 (m, 16H), 2.40 (s, 3H), 2.72 (t, J=7.7 Hz, 2H), 6.63 (s, 1H), 7.17 (dd, J=8.4, 1.6 Hz, 1H), 7.45 (s, 1H), 7.63 (d, J=8.4 Hz, 1H), 7.97 (s, 1H); $^{13}$C NMR (100 MHz, CDCl$_3$) δ 14.4, 20.4, 23.0, 29.6, 29.7, 29.9 (×2), 31.6, 32.2, 36.5, 109.1, 123.4, 125.2, 125.9, 127.5, 127.8, 134.5, 135.8, 142.3, 153.2; IR (KBr) ν 3402 cm$^{-1}$ (OH); EI-MS, m/z=330 (M$^+$); Anal. Calcd for C$_{21}$H$_{30}$OS: C, 76.31; H, 9.15%. Found: C, 76.62; H, 9.38%.

Synthesis Example 2-2

Synthesis of 7-decyl-3-methylthio-2-(trifluoromethanesulfonyloxy)naphthalene (compound (4)-77)

7-Decyl-3-methylthio-2-hydroxynaphthalene was trifluoromethanesulfonylated by the same operation as that in (Synthesis Example 1-2) to obtain 7-decyl-3-methylthio-2-(trifluoromethanesulfonyloxy)naphthalene (compound (4)-77).

yield of 94%; yellow crystal (recrystallized with hexane); mp 149 to 150° C.; $^1$H NMR (400 MHz, CDCl$_3$) δ 2.44 (s, 3H), 6.64 (s, 1H), 7.38-7.40 (m, 2H), 7.48 (tt, J=7.6, 1.8 Hz, 1H), 7.60 (d, J=8.5 Hz, 1H), 7.70-7.72 (m, 2H), 7.80 (dd, J=8.5, 2.0 Hz, 1H), 7.88 (s, 1H), 8.02 (d, J=2.0 Hz, 1H); $^{13}$C NMR (126 MHz, CDCl$_3$) δ 14.4, 16.4, 23.0, 29.6, 29.7, 29.8, 29.9, 30.0, 31.5, 32.2, 36.3, 119.0 (q, J=320 Hz), 119.3, 126.6, 127.0, 127.5, 129.7, 129.9, 131.6, 131.8, 142.1, 125.9; IR (neat) ν 1427, 1213 cm$^{-1}$ (—O—SO$_2$—); EI-MS, m/z=266 (M$^+$); Anal. Calcd for C$_{17}$H$_{14}$OS: C, 76.66; H, 5.30%. Found: C, 76.97; H, 5.14%.

Synthesis Example 3

Synthesis of 3-methylthio-7-phenyl-2-(trifluoromethanesulfonyloxy)naphthalene (compound (4)-72)

Synthesis Example 3-1

Synthesis of 3-methylthio-7-phenyl-2-naphthol

3-Methylthio-7-phenyl-2-methoxynaphthalene (compound (4)-22) synthesized in Example 16 was demethylated by the operation in (Synthesis Example 1-1) to obtain 3-methylthio-7-phenyl-2-naphthol.

yield of 94%; yellow crystal (recrystallized with hexane);
mp 149 to 150° C.; $^1$H NMR (400 MHz, CDCl$_3$) δ 2.44 (s, 3H), 6.64 (s, 1H), 7.38-7.40 (m, 2H), 7.48 (tt, J=7.6, 1.8 Hz, 1H), 7.60 (d, J=8.5 Hz, 1H), 7.70-7.72 (m, 2H), 7.80 (dd, J=8.5, 2.0 Hz, 1H), 7.88 (s, 1H), 8.02 (d, J=2.0 Hz, 1H); $^{13}$C NMR (100 MHz, CDCl$_3$) δ 20.2, 109.8, 124.1, 124.7, 127.7, 127.9, 128.5, 129.2 (×2), 134.1, 135.7, 140.1, 141.3, 153.4; IR (KBr) ν 3497 cm$^{-1}$ (OH); EI-MS, m/z=266 (M$^+$); Anal. Calcd for C$_{17}$H$_{14}$OS: C, 76.66; H, 5.30%. Found: C, 76.97; H, 5.14%.

Synthesis Example 3-2

Synthesis of 3-methylthio-7-phenyl-2-(trifluoromethanesulfonyloxy)naphthalene (compound (4)-72)

3-Methylthio-7-phenyl-2-naphthol was trifluoromethanesulfonylated by the same operation as that in Synthesis Example 1-2 to obtain 3-methylthio-7-phenyl-2-(trifluoromethanesulfonyloxy)naphthalene (compound (4)-72).
yield of 98%; yellow crystal (recrystallized with hexane);
mp 87.8 to 88.7° C.; $^1$H NMR (400 MHz, CDCl$_3$) δ 2.62 (s, 3H), 7.41 (tt, J=7.2, 1.2 Hz, 1H), 7.45-7.52 (m, 2H), 7.68-7.71 (m, 2H), 7.72 (s, 1H), 7.79 (s, 1H), 7.82 (dd, J=8.4, 1.6 Hz, 1H), 7.87 (d, J=8.4 Hz, 1H), 8.00 (s, 1H); $^{13}$C NMR (126 MHz, CDCl$_3$) δ 16.0, 119.0 (q, J=321 Hz), 120.0, 125.9, 126.8, 127.6, 127.7, 127.8, 128.2, 129.3, 131.3, 131.7, 132.3, 139.8, 140.5, 146.0; IR (KBr) ν 1425, 1209 cm$^{-1}$ (O—SO$_2$—); EI-MS, m/z=398 (M$^+$); Anal. Calcd for C$_{18}$H$_{13}$O$_3$S$_2$F$_3$: C, 54.26; H, 3.29%. Found: C, 54.42; H, 3.08%.

Synthesis Example 4

Synthesis of 3-methylthio-6-phenyl-2-(trifluoromethanesulfonyloxy)naphthalene (compound (4)-73)

Synthesis Example 4-1

Synthesis of 3-methylthio-6-phenyl-2-naphthol

The 3-methylthio-6-phenyl-2-methoxynaphthalene (compound (4)-31) obtained in Example 17 was demethylated by the operation in Synthesis Example 1-1 to obtain 3-methylthio-6-phenyl-2-naphthol.
yield of 73%; yellow crystal (recrystallized with hexane);
mp 128.9 to 129.8° C.; $^1$H NMR (400 MHz, CDCl$_3$) δ 2.45 (s, 3H), 6.63 (s, 1H), 7.35 (s, 1H), 7.37 (tt, J=7.4, 1.3 Hz, 1H), 7.45-7.50 (m, 2H), 7.72 (dd, J=8.5, 1.8 Hz, 1H), 7.76 (d, J=8.6 Hz, 1H) 7.68-7.72 (m, 2H), 7.76 (d, J=8.5 Hz, 1H), 7.92 (d, J=1.8 Hz, 1H); $^{13}$C NMR (100 MHz, CDCl$_3$) δ 20.2, 109.4, 125.2, 125.5, 127.1, 127.3, 127.5, 127.6, 129.2, 129.5, 134.5 (×2), 137.0, 141.3, 153.1; IR (KBr) ν 3402 cm$^{-1}$ (OH); EI-MS, m/z=266 (M$^+$); Anal. Calcd for C$_{17}$H$_{14}$OS: C, 76.66; H, 5.30%. Found: C, 76.50; H, 5.15%.

Synthesis Example 4-2

Synthesis of 3-methylthio-6-phenyl-2-(trifluoromethanesulfonyloxy)naphthalene (compound (4)-73)

3-Methylthio-6-phenyl-2-naphthol was trifluoromethanesulfonylated by the same operation as that in Synthesis Example 1-2 to obtain 3-methylthio-6-phenyl-2-(trifluoromethanesulfonyloxy)naphthalene (compound (4)-73).
yield: quantitative; yellow crystal (recrystallized with hexane);
mp 79.4 to 80.3° C.; $^1$H NMR (400 MHz, CDCl$_3$) δ 2.62 (s, 3H), 7.42 (tt, J=7.4, 1.3 Hz, 1H), 7.43-7.52 (m, 2H), 7.68-7.71 (m, 2H), 7.74 (s, 1H), 7.75 (s, 1H), 7.77 (dd, J=8.5, 1.8 Hz, 1H), 7.88 (d, J=8.5 Hz, 1H), 7.99 (d, J=1.8 Hz, 1H); $^{13}$C NMR (126 MHz, CDCl$_3$) δ 16.0, 119.0 (q, J=321 Hz), 119.6, 124.9, 126.8, 127.1, 127.8, 128.2, 128.7, 129.3, 130.5, 131.9, 133.4, 140.7, 140.9, 145.6; IR (KBr) ν 1429, 1225 cm$^{-1}$ (O—SO$_2$—); EI-MS, m/z=398 (M$^+$); Anal. Calcd for C$_{18}$H$_{13}$O$_3$S$_2$F$_3$: C, 54.26; H, 3.29%. Found: C, 54.17; H, 3.01%.

Synthesis Example 5

Synthesis of 6-tolyl-3-methylthio-2-trifluoromethanesulfonyloxynaphthalene (compound (4)-83)

6-Tolyl-3-methylthio-2-methoxynaphthalene (compound (4)-32, 10.5 g) obtained in Example 18 was demethylated with a dichloromethane solution of BBr$_3$ by the same method as that in Synthesis Example 1-1, and subsequently trifluoromethanesulfonylated to obtain 6-tolyl-3-methylthio-2-trifluoromethanesulfonyloxynaphthalene (compound (4)-83, 12.5 g, yield of 85%).
EI-MS, m/z=412 (M$^+$)

Synthesis Example 6

Synthesis of 7-tolyl-3-methylthio-2-trifluoromethanesulfonyloxynaphthalene (compound (4)-82)

7-Tolyl-3-methylthio-2-methoxynaphthalene (compound (4)-23, 15.4 g) obtained in Example 19 was demethylated with a dichloromethane solution of BBr$_3$ by the same method as that in Synthesis Example 1-1, and subsequently trifluoromethanesulfonylated to obtain 7-tolyl-3-methylthio-2-trifluoromethanesulfonyloxynaphthalene (compound (4)-82, 8.62 g, yield of 67%).
EI-MS, m/z=412 (M$^+$)

Synthesis Example 7

Synthesis of 6-biphenyl-3-methylthio-2-trifluoromethanesulfonyloxynaphthalene (compound (4)-85)

6-Biphenyl-3-methylthio-2-methoxynaphthalene obtained in Example 20 (compound (4)-33, 15.4 g) was demethylated with a dichloromethane solution of BBr$_3$ by the same method as that in (Synthesis Example 1-1), and subsequently trifluoromethanesulfonylated to obtain 6-biphenyl-3-methylthio-2-trifluoromethanesulfonyloxynaphthalene (compound (4)-85, 15.9 g, yield of 77%).
EI-MS, m/z=474 (M$^+$)

Synthesis Example 8

Synthesis of 7-biphenyl-3-methylthio-2-trifluoromethanesulfonyloxynaphthalene (compound (4)-84)

7-Biphenyl-3-methylthio-2-methoxynaphthalene (compound (4)-24, 15.8 g) obtained in Example 21 was demethylated with a dichloromethane solution of BBr₃ by the same method as that in Synthesis Example 1-1, and subsequently trifluoromethanesulfonylated to obtain 7-biphenyl-3-methylthio-2-trifluoromethanesulfonyloxynaphthalene (compound (4)-84, 18.9 g, yield of 93%).

EI-MS, m/z=474 (M⁺)

Synthesis Example 9

Synthesis of 7-butyl-3-methylthio-2-trifluoromethanesulfonyloxynaphthalene (compound (4)-74)

7-Butyl-3-methylthio-2-methoxynaphthalene (compound (4)-04, 21.63 g, 83.1 mmol) obtained in Example 22 was demethylated with a dichloromethane solution of BBr₃ by the same method as that in Synthesis Example 1-1, and subsequently trifluoromethanesulfonylated to obtain 7-butyl-3-methylthio-2-trifluoromethanesulfonyloxynaphthalene (compound (4)-74, 18.5 g, yield of 59%).

EI-MS, m/z=378 (M⁺)

Synthesis Example 10

Synthesis of 7-hexyl-3-methylthio-2-trifluoromethanesulfonyloxynaphthalene (compound (4)-75)

7-Hexyl-3-methylthio-2-methoxynaphthalene (compound (4)-08, 24.7 g) obtained in Example 23 was demethylated with a dichloromethane solution of BBr₃ by the same method as that in (Synthesis Example 1-1), and subsequently trifluoromethanesulfonylated to obtain 7-hexyl-3-methylthio-2-trifluoromethanesulfonyloxynaphthalene (compound (4)-75, 23.5 g, yield of 70%).

EI-MS, m/z=406 (M⁺)

Synthesis Example 11

Synthesis of 7-octyl-3-methylthio-2-trifluoromethanesulfonyloxynaphthalene (compound (4)-76)

7-Octyl-3-methylthio-2-methoxynaphthalene (compound (4)-10, 27.09 g) obtained in Example 24 was demethylated with a dichloromethane solution of BBr₃ by the same method as that in Synthesis Example 1-1, and subsequently trifluoromethanesulfonylated to obtain 7-octyl-3-methylthio-2-trifluoromethanesulfonyloxynaphthalene (compound (4)-76, 25.00 g, yield of 64%).

EI-MS, m/z=434 (M⁺)

Synthesis Example 12

Synthesis of 7-dodecyl-3-methylthio-2-trifluoromethanesulfonyloxynaphthalene (compound (4)-78)

7-Dodecyl-3-methylthio-2-methoxynaphthalene (compound (4)-14, 34.1 g) obtained in Example 25 was demethylated with a dichloromethane solution of BBr₃ by the same method as that in Synthesis Example 1-1, and subsequently trifluoromethanesulfonylated to obtain 7-dodecyl-3-methylthio-2-trifluoromethanesulfonyloxynaphthalene (compound (4)-78, 33.7 g, yield of 72%).

EI-MS, m/z=490 (M⁺)

Synthesis Example 13

Synthesis of 1,2-bis(tributylstanyl)ethylene (compound (5)-05)

Synthesis Example 13-1

Synthesis of tributylstanylacetylene

Under a nitrogen atmosphere, tributyltinchloride (8.6 ml, 32 mmol) was added to a THF (60 ml) solution of xylene of 18 w % Na acetylene and a dispersion oil of a mineral oil (10 ml, 8.5 g, 32 mmol) at 0° C. The solution was stirred at room temperature for 17 hours. Then, the mixture was extracted with hexane, and washed with saline water. The organic phases were mixed, and the mixture was dried with MgSO₄, and condensed. The condensed product was distilled at reduced pressure (85 to 120° C., approximately 0.7 mmHg) to obtain tributylstanylacetylene (3.6 g, 34%) as a colorless oily substance.

¹H-NMR (400 MHz, CDCl₃) δ 0.91 (t, 9H, J=8.0 Hz), 1.02 (t, 8H, J=8.0 Hz), 1.35 (sextet, 6H, J=8.0 Hz), 1.58 (quintet, 6H, J=8.0 Hz), 2.20 (s, 1H)

Synthesis Example 13-2

Synthesis of 1,2-bis(tributylstanyl)ethylene (compound (5)-05)

Under a nitrogen atmosphere, azobisisobutyronitrile (100 mg, 0.60 mmol) was added to a toluene (20 ml) solution of tributylstanylacetylene (1.6 g, 5 mmol) and tributyltinhydride (1.3 ml, 5 mmol). The mixture was heated and stirred for 17 hours at 90° C. Water (20 ml) was added, and the mixture was condensed. The mixture was extracted with hexane. The extracted solution was washed with saline water to obtain 1,2-bis(tributylstanyl)ethylene (compound (5)-05) (3.0 g, 90%) as a colorless oily substance.

¹H-NMR (400 MHz, CDCl₃) δ 0.86-0.91 (multiplet, 15H), 1.31 (sextet, 6H, J=8.0 Hz), 1.50 (quintet, 6H, J=8.0 Hz), 6.88 (s, 2H)

Example 26

Synthesis of trans-1,2-bis(6-decyl-3-methylthionaphthalen-2-yl)ethylene (compound (6)-64)

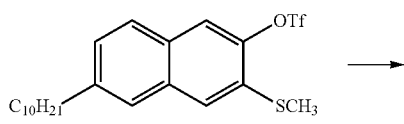

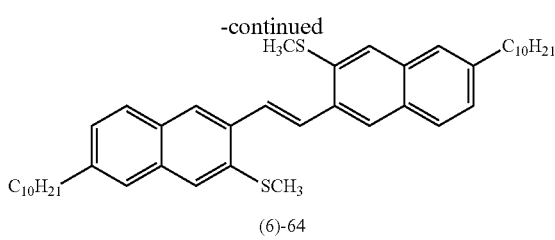

(6)-64

Pd(PPh$_3$)$_4$ (322 mg, 0.29 mmol, 7 mol %) was added to a DMF (40 ml) solution of 6-decyl-3-methylthio-2-(trifluoromethanesulfonyloxy)naphthalene (compound (4)-81) (1.9 g, 4.1 mmol) and 1,2-bis(tributylstanyl)ethylene (compound (5)-05). The mixture was heated and stirred at 90° C. for 17 hours in a dark place, diluted with water, and extracted with chloroform. The extracted solution was dried with MgSO$_4$, and condensed. The residue was refined by column chromatography (silica gel, developed with dichloromethane) to obtain trans-1,2-bis(6-decyl-3-methylthionaphthalen-2-yl) ethylene (compound (6)-64) (2.3 g, quantitative) as a yellow solid.

mp 116.8 to 117.7° C.; $^1$H NMR (400 MHz, CDCl$_3$) δ 0.88 (t, J=6.4 Hz, 6H), 1.29-1.70 (m, 32H), 2.58 (s, 6H), 2.75 (t, J=8.4 Hz, 4H), 7.29 (dd, J=8.8, 1.6 Hz, 2H), 7.52 (s, 2H), 7.59 (s, 2H), 7.64 (s, 2H), 7.76 (d, J=8.4 Hz, 2H), 8.06 (s, 2H); $^{13}$C NMR (100 MHz, CDCl$_3$) δ 14.4, 16.8, 23.0, 24.2, 29.6, 29.8, 29.9, 30.0, 31.7, 32.2, 36.5, 124.3, 125.2, 125.3, 127.6, 128.0, 128.4, 130.3, 133.9, 134.5, 136.0, 141.6; EI-MS m/z=652 (M$^+$).

Example 27

Synthesis of trans-1,2-bis(7-decyl-3-methylthionaphthalen-2-yl)ethylene (compound (6)-12)

Trans-1,2-bis(7-decyl-3-methylthionaphthalen-2-yl)ethylene (compound (6)-12) was obtained from 7-decyl-3-methylthio-2-(trifluoromethanesulfonyloxy)naphthalene (compound (4)-77) and 1,2-bis(tributylstanyl)ethylene (compound (5)-05) by the same operation as that in Example 26. yield of 98%; yellow crystal (recrystallized with hexane);

mp 87.8-88.7° C.; $^1$H NMR (400 MHz, CDCl$_3$) δ 2.62 (s, 3H), 7.41 (tt, J=7.2, 1.2 Hz, 1H), 7.45-7.52 (m, 2H), 7.68-7.71 (m, 2H), 7.72 (s, 1H), 7.79 (s, 1H), 7.82 (dd, J=8.4, 1.6 Hz, 1H), 7.87 (d, J=8.4 Hz, 1H), 8.00 (s, 1H); EI-MS, m/z=398 (M$^+$); Anal. Calcd for C$_{18}$H$_{13}$O$_3$S$_2$F$_3$: C, 54.26; H, 3.29%. Found: C, 54.42; H, 3.08%.

Example 28

Synthesis of trans-1,2-bis(3-methylthio-7-phenylnaphtho-2-yl)ethylene (compound (6)-22)

Trans-1,2-bis(3-methylthio-7-phenylnaphtho-2-yl)ethylene (compound (6)-22) was obtained from 3-methylthio-7-phenyl-2-(trifluoromethanesulfonyloxy)naphthalene (compound (4)-72) and 1,2-bis(tributylstanyl)ethylene (compound (5)-05) by the same operation as that in Example 26.

yield of 63%; yellow solid (recrystallized with hexane);
mp 87.8 to 88.7° C.; $^1$H NMR (400 MHz, CDCl$_3$) δ 2.63 (s, 6H), 7.40 (tt, J=7.4, 1.2 Hz, 2H), 7.48-7.52 (m, 4H), 7.68 (s, 2H), 7.73-7.76 (m, 4H), 7.72 (s, 2H), 7.72 (d, J=8.2 Hz, 2H), 7.83 (d, J=8.2 Hz, 2H), 8.08 (s, 2H), 8.17 (s, 2H); EI-MS, m/z=524 (M$^+$); Anal. Calcd for C$_{34}$H$_{25}$S$_2$: C, 82.40; H, 5.38%. Found: C, 82.38; H, 5.22%.

Example 29

Synthesis of trans-1,2-bis(3-methylthio-6-phenylnaphtho-2-yl)ethylene (compound (6)-31)

Trans-1,2-bis(3-methylthio-6-phenylnaphtho-2-yl)ethylene (compound (6)-31) was obtained from 3-methylthio-6-phenyl-2-(trifluoromethanesulfonyloxy)naphthalene (compound (4)-73) and 1,2-bis(tributylstanyl)ethylene (compound (5)-05) by the same operation as that in Example 26.

yield of 57%; yellow solid (recrystallized with hexane);
mp 191.5 to 192.4° C.; $^1$H NMR (400 MHz, CDCl$_3$) δ 2.64 (s, 6H), 7.40 (tt, J=7.2, 1.6 Hz, 2H), 7.48-7.53 (m, 4H), 7.71 (s, 2H), 7.72 (s, 2H), 7.73-7.76 (m, 4H), 7.76 (d, J=8.7 Hz, 2H), 7.94 (d, J=8.7 Hz, 2H), 7.97 (s, 2H), 8.14 (s, 2H); EI-MS, m/z=524 (M$^+$); Anal. Calcd for C$_{34}$H$_{25}$S$_2$: C, 82.40; H, 5.38%. Found: C, 82.22; H, 5.29%.

Example 30

Synthesis of trans-1,2-bis(6-tolyl-3-methylthionaphthalen-2-yl)ethylene (compound (6)-32)

Trans-1,2-bis(6-tolyl-3-methylthionaphthalen-2-yl)ethylene (compound (6)-32, 2.0 g, yield of 24%) as a light yellow solid was obtained from 6-tolyl-3-methylthio-2-trifluoromethanesulfonyloxynaphthalene (compound (4)-83, 12.5 g) by the same operation as that in Example 26.

EI-MS, m/z=552 (M$^+$)

Example 31

Synthesis of trans-1,2-bis(7-tolyl-3-methylthionaphthalen-2-yl)ethylene (compound (6)-23)

Trans-1,2-bis(7-tolyl-3-methylthionaphthalen-2-yl)ethylene (compound (6)-23, 3.64 g, yield of 64%) as a light yellow solid was obtained from 7-tolyl-3-methylthio-2-trifluoromethanesulfonyloxynaphthalene (compound (4)-82, 8.50 g) by the same operation as that in Example 26.

EI-MS, m/z=552 (M$^+$)

Example 32

Synthesis of trans-1,2-bis(6-biphenyl-3-methylthionaphthalen-2-yl)ethylene (compound (6)-33)

Trans-1,2-bis(6-biphenyl-3-methylthionaphthalen-2-yl)ethylene (compound (6)-33, 8.52 g, yield of 76%) as a light yellow solid was obtained from 6-biphenyl-3-methylthio-2-trifluoromethanesulfonyloxynaphthalene (compound (4)-85, 15.8 g) by the same operation as that in Example 26.

EI-MS, m/z=676 (M$^+$)

Example 33

Synthesis of trans-1,2-bis(7-biphenyl-3-methylthionaphthalen-2-yl)ethylene (compound (6)-24)

Trans-1,2-bis(7-biphenyl-3-methylthionaphthalen-2-yl)ethylene (compound (6)-24, 11.56 g, yield of 86%) as a light yellow solid was obtained from 7-biphenyl-3-methylthio-2-trifluoromethanesulfonyloxynaphthalene (compound (4)-84, 18.9 g) by the same operation as that in Example 26.

EI-MS, m/z=676 (M$^+$)

Example 34

Synthesis of trans-1,2-bis(7-butyl-3-methylthionaphthalen-2-yl)ethylene (compound (6)-04)

Trans-1,2-bis(7-butyl-3-methylthionaphthalen-2-yl)ethylene (compound (6)-04) as a light yellow solid (5.32 g, yield of 45%) was obtained from 7-butyl-3-methylthio-2-trifluoromethanesulfonyloxynaphthalene (compound (4)-74, 18.20 g, 47.6 mmol) by the same operation as that in Example 26.

EI-MS, m/z=492 (M$^+$)

Example 35

Synthesis of trans-1,2-bis(7-hexyl-3-methylthionaphthalen-2-yl)ethylene (compound (6)-08)

Trans-1,2-bis(7-hexyl-3-methylthionaphthalen-2-yl)ethylene (compound (6)-08) as a light yellow solid (6.73 g, yield of 43%) was obtained from 7-hexyl-3-methylthio-2-trifluoromethanesulfonyloxynaphthalene (compound (4)-75, 23.3 g) by the same operation as that in Example 26.

EI-MS, m/z=540 (M$^+$)

Example 36

Synthesis of trans-1,2-bis(7-octyl-3-methylthionaphthalen-2-yl)ethylene (compound (6)-10)

Trans-1,2-bis(7-octyl-3-methylthionaphthalen-2-yl)ethylene (compound (6)-10) as a light yellow solid (7.46 g, yield of 43%) was obtained from 7-octyl-3-methylthio-2-trifluoromethanesulfonyloxynaphthalene (compound (4)-76, 25.00 g) by the same operation as that in Example 26.

EI-MS, m/z=596 (M$^+$)

Example 37

Synthesis of trans-1,2-bis(7-dodecyl-3-methylthionaphthalen-2-yl)ethylene (compound (6)-14)

Trans-1,2-bis(7-dodecyl-3-methylthionaphthalen-2-yl)ethylene (compound (6)-14) as a light yellow solid (8.08 g, yield of 40%) was obtained from 7-octyl-3-methylthio-2-trifluoromethanesulfonyloxynaphthalene (compound (4)-78, 27.8 g) by the same operation as that in Example 26.

EI-MS, m/z=709 (M$^+$)

Synthesis Example 14

Synthesis of 2,9-didecyldinaphtho[2,3-b:2',3'-f]thieno[2,3-b]thiophene (compound (2)-64)

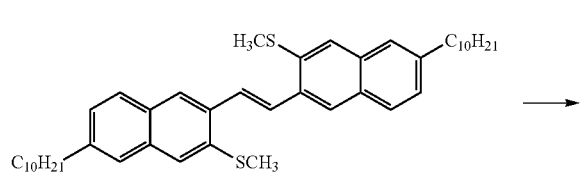

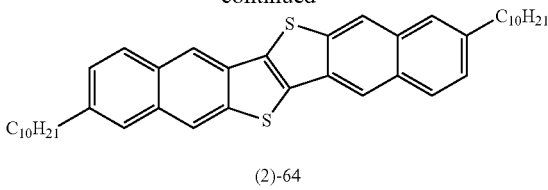

(2)-64

A chloroform (4 ml) solution of trans-1,2-bis(6-decyl-3-methylthionaphthalen-2-yl)ethylene (compound (6)-64) (38 mg, 58 mmol) and I$_2$ (470 mg, 1.8 mmol) was stirred at room temperature for 20 hours. The mixture was condensed, and methanol (5 ml) and a NaHSO$_3$ aqueous solution (5 ml) were added to the mixture. The mixture was filtered, and washed with water, acetone, methanol, and toluene to obtain 2,9-didecyldinaphtho[2,3-b:2',3'-f]thieno[2,3-b]thiophene (compound (2)-64) (29 mg, 81%) as a yellow solid.

EIMS (70 eV) m/z=620 (M$^+$).

Example 38

Synthesis of 3,10-didecyl dinaphtho[2,3-b:2',3'-f]thieno[2,3-b]thiophene (compound (1)-12)

3,10-Didecyldinaphtho[2,3-b:2',3'-f]thieno[2,3-b]thiophene (compound (1)-12) was obtained from trans-1,2-bis(7-decyl-3-methylthionaphthalene-2-yl)ethylene (compound (6)-12) by the same method as that in Synthesis Example 14.

yield of 71%; mp 187 to 188° C.;

$^1$H NMR (400 MHz, CDCl$_3$) δ 0.88 (t, J=6.9 Hz, 6H), 1.24-1.79 (m, 32H), 2.82 (t, J=7.7 Hz, 4H), 7.38 (dd, J=8.5, 1.6 Hz, 2H), 7.79 (s, 2H), 7.86 (d, J=8.5 Hz, 2H), 8.29 (s, 2H), 8.36 (s, 2H); EI-MS, m/z=620 (M$^+$); Anal. Calcd for C$_{42}$H$_{52}$S$_2$: C, 81.46; H, 8.43%. Found: C, 81.13; H, 8.43%.

Example 39

Synthesis of 3,10-diphenyl dinaphtho[2,3-b:2',3'-f]thieno[3,2-b]thiophene (3,10-PhDNTT) (compound (1)-22)

3,10-Diphenyldinaphtho[2,3-b:2',3'-f]thieno[3,2-b]thiophene (3,10-PhDNTT) (compound (1)-22) was obtained from trans-1,2-bis(3-methylthio-7-phenylnaphtho-2-yl)ethylene (compound (6)-22) by the same method as that in Synthesis Example 14. yield of 85%; mp>300° C.;

EI-MS, m/z=492 (M$^+$); Anal. Calcd for C$_{34}$H$_{20}$S$_2$: C, 82.89; H, 4.09%. Found: C, 82.80; H, 3.78%.

Example 40

Synthesis of 2,9-diphenyl dinaphtho[2,3-b:2',3'-f]thieno[3,2-b]thiophene (2,9-PhDNTT) (compound (1)-31)

2,9-Diphenyldinaphtho[2,3-b:2',3'-f]thieno[3,2-b]thiophene(2,9-PhDNTT) (compound (1)-31) was obtained from trans-1,2-bis(3-methylthio-6-phenylnaphtho-2-yl)ethylene (compound (6)-31) by the same method as that in Synthesis Example 14.

yield of 89%; mp>300° C.;

EI-MS, m/z=492 (M$^+$); Anal. Calcd for C$_{34}$H$_{20}$S$_2$: C, 82.89; H, 4.09%. Found: C, 82.73; H, 3.75%.

Example 41

Synthesis of 2,9-ditolyldinaphtho[2,3-b:2',3'-f]thieno [2,3-b]thiophene (compound (1)-32)

2,9-Ditolyldinaphtho[2,3-b:2',3'-f]thieno[2,3-b]thiophene (compound (1)-32) as a yellow solid (1.78 g, 95%) was obtained from trans-1,2-bis(6-tolyl-3-methylthionaphthalen-2-yl)ethylene (compound (6)-32, 2.0 g) by the same method as that in Synthesis Example 14.

EI-MS, m/z=520 (M$^+$), 427, 260 (M+/2).
thermal analysis (endothermic peak): 492° C. (TG-DTA was used, nitrogen)

Example 42

Synthesis of 3,10-ditolyldinaphtho[2,3-b:2',3'-f] thieno[2,3-b]thiophene (compound (1)-23)

3,10-Ditolyldinaphtho[2,3-b:2',3'-f]thieno[2,3-b]thiophene (compound (1)-23) as a yellow solid (3.38 g, quantitative) was obtained from trans-1,2-bis(7-tolyl-3-methylthionaphthalen-2-yl)ethylene (compound (6)-23, 3.60 g) by the same method as that in Synthesis Example 14.

EI-MS, m/z=520 (M$^+$), 427, 260 (M+/2), 172.
thermal analysis (endothermic peak): 401° C. (TG-DTA was used, nitrogen)

Example 43

Synthesis of 2,9-dibiphenyldinaphtho[2,3-b:2',3'-f] thieno[2,3-b]thiophene (compound (1)-33)

Trans-1,2-bis(6-biphenyl-3-methylthionaphthalen-2-yl) ethylene (compound (6)-33, 8.40 g) was reacted with iodine by the same method as that in Synthesis Example 14 to obtain 2,9-dibiphenyldinaphtho[2,3-b:2',3'-f]thieno[2,3-b] thiophene (compound (1)-33) as a yellow solid (7.76 g, 97%).

EI-MS, m/z=644 (M$^+$), 566, 490, 429, 322 (M+/2), 207.
thermal analysis (endothermic peak), no clear peak at less than 500° C. (TG-DTA was used, nitrogen)

Example 44

Synthesis of 3,10-dibiphenyldinaphtho[2,3-b:2',3'-f] thieno[2,3-b]thiophene (compound (1)-24)

Trans-1,2-bis(7-biphenyl-3-methylthionaphthalen-2-yl) ethylene (compound (6)-24, 11.50 g) was reacted with iodine by the same method as that in Synthesis Example 14 to obtain 3,10-dibiphenyldinaphtho[2,3-b:2',3'-f]thieno[2,3-b] thiophene (compound (1)-24) as a yellow solid (10.32 g, yield of 94%).

EI-MS, m/z=644 (M$^+$), 492, 429, 322 (M+/2), 270.
thermal analysis (endothermic peak), no clear peak at less than 500° C. (TG-DTA was used, nitrogen)

Example 45

Synthesis of 3,10-dibutyldinaphtho[2,3-b:2',3'-f] thieno[2,3-b]thiophene (compound (1)-04)

Trans-1,2-bis(7-butyl-3-methylthionaphthalen-2-yl)ethylene (compound (6)-04) was reacted with iodine by the same method as that in Synthesis Example 14 to obtain 3,10-dibutyldinaphtho[2,3-b:2',3'-f]thieno[2,3-b]thiophene (compound (1)-04) as a yellow solid (4.66 g, quantitative).

EI-MS, m/z=452 (M$^+$), 409, 366, 184, 183.
thermal analysis (endothermic peak): 185, 283° C. (DSC was used, nitrogen)

$^1$H NMR (400 MHz, CDCl$_3$) δ 0.98 (t, 6H), δ 1.35~1.50 (m, 4H), δ 1.70-1.80 (m, 4H), δ 2.80-2.90 (m, 4H) δ 7.39 (dd, 2H, ArH) δ 7.78 (s, 2H, ArH) δ 7.84 (d, 2H, ArH) δ 8.27 (s, 2H, ArH) δ 8.34 (s, 2H, ArH).

Example 46

Synthesis of 3,10-dihexyldinaphtho[2,3-b:2',3'-f] thieno[2,3-b]thiophene (compound (1)-08)

Trans-1,2-bis(7-hexyl-3-methylthionaphthalen-2-yl)ethylene (compound (6)-08, 6.50 g) was reacted with iodine by the same method as that in Synthesis Example 14 to obtain 3,10-dihexyldinaphtho[2,3-b:2',3'-f]thieno[2,3-b]thiophene (compound (1)-08) as a yellow solid (3.18 g, yield of 52%).

EI-MS, m/z=508 (M$^+$), 437, 366, 184, 183
thermal analysis (endothermic peak): 202, 259° C. (DSC was used, nitrogen)

$^1$H NMR (400 MHz, CDCl$_3$) δ 0.90 (t, 6H), δ 1.20~1.55 (m, 12H), δ 1.70-1.80 (m, 4H), δ 2.75-2.90 (m, 4H) δ 7.39 (dd, 2H, ArH) δ 7.78 (s, 2H, ArH) δ 7.84 (d, 2H, ArH) δ 8.27 (s, 2H, ArH) δ 8.34 (s, 2H, ArH).

Example 47

Synthesis of 3,10-dioctyldinaphtho[2,3-b:2',3'-f] thieno[2,3-b]thiophene (compound (1)-10)

Trans-1,2-bis(7-hexyl-3-methylthionaphthalen-2-yl)ethylene (compound (6)-10, 7.20 g, 12.1 mmol) was reacted with iodine by the same method as that in Synthesis Example 14 to obtain 3,10-dioctyldinaphtho[2,3-b:2',3'-f]thieno[2,3-b] thiophene (compound (1)-10) as a yellow solid (3.50 g, yield of 51%).

EI-MS, m/z=564 (M$^+$), 465, 366, 184, 183
thermal analysis (endothermic peak): 177, 237° C. (DSC was used, nitrogen) $^1$H NMR (400 MHz, CDCl$_3$) δ 0.88 (m, 6H), δ 1.10~1.50 (m, 20H), δ 1.60-1.85 (m, 4H), δ 2.70-2.90 (m, 4H) δ 7.36 (m, 2H, ArH) δ 7.77 (s, 2H, ArH) δ 7.83 (d, 2H, ArH) δ 8.26 (s, 2H, ArH) δ 8.30 (s, 2H, ArH).

Example 48

Synthesis of 3,10-didodecyldinaphtho[2,3-b:2',3'-f] thieno[2,3-b]thiophene (compound (1)-14)

Trans-1,2-bis(7-dodecyl-3-methylthionaphthalen-2-yl) ethylene (compound (6)-14, 7.80, 11 mmol) was reacted with iodine by the same method as that in Synthesis Example 14 to obtain 3,10-didodecyldinaphtho[2,3-b:2',3'-f]thieno[2,3-b] thiophene (compound (1)-14) as a yellow solid (6.26 g, yield of 84%).

EI-MS, m/z=677 (M$^+$), 521, 366, 184, 183
thermal analysis (endothermic peak): 100, 123, 158, 212° C. (DSC was used, nitrogen)

$^1$H NMR (400 MHz, CDCl$_3$) δ 0.80-0.90 (m, 6H), δ 1.20~1.60 (m, 36H), δ 1.70-1.85 (m, 4H), δ 2.80-2.90 (m, 4H) δ 7.36 (dd, 2H, ArH) δ 7.80 (s, 2H, ArH) δ 7.83 (d, 2H, ArH) δ 8.26 (s, 2H, ArH) δ 8.34 (s, 2H, ArH).

As above, development of the novel synthesis method enabled synthesis of a variety of DNTT derivatives (1) and (2) that are extremely high performance organic semiconductors having a substituent at various positions. Particularly, synthesis method of the present invention succeeded for the first time in synthesis of the compound (1) exhibiting excellent properties as the semiconductor.

Next, a novel heterocyclic compound represented by the compound (1) and a field effect transistor having a semiconductor layer comprising the compound, and a field effect transistor having a semiconductor layer comprising the compound (2) synthesized in the present invention will be specifically described.

Example 49

Creation of Top Contact Type Field Effect Transistor

An n-doped silicon wafer subjected to an octadecyltrichlorosilane treatment and having a 300 nm SiO$_2$ thermal oxide film (surface resistance of 0.02 Ω·cm or less) was placed inside of a vacuum deposition apparatus, and the air in the apparatus was discharged until the degree of vacuum of the air reached 5.0×10$^{-3}$ Pa or less. Each of the compounds (1)-12, (1)-22, and (1)-31 was deposited onto an electrode to have a thickness of 50 nm by a resistance heating deposition method under the condition of a substrate temperature of approximately 60° C. Thereby, a semiconductor layer (2) was formed. Next, a shadow mask for creating an electrode was attached to this substrate. The substrate was placed inside of the vacuum deposition apparatus, and the air in the apparatus was discharged until the degree of vacuum of the air reached 1.0×10$^{-4}$ Pa or less. The gold electrodes, that is, the source electrode (1) and the drain electrode (3) were deposited by the resistance heating deposition method to have a thickness of 40 nm. Thereby, a TC (top contact) type field effect transistor of the present invention was obtained.

Figure 3:
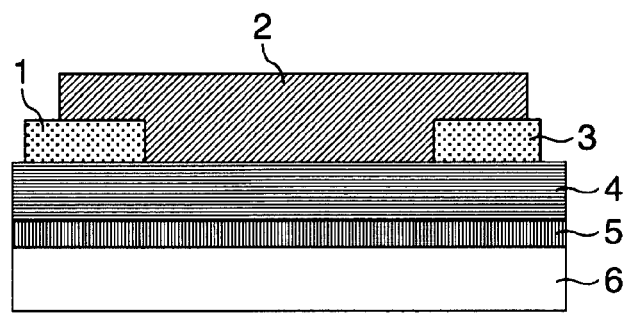
FIG. 3 is a schematic view showing a field effect transistor obtained in Comparative Example 1.

In the field effect transistor, the thermal oxide film in the n-doped silicon wafer having a thermal oxide film has the function of the insulator layer (4), and the n-doped silicon wafer has the functions of the substrate (6) and the gate electrode (5) (see FIG. 3).

The obtained field effect transistor was placed inside of a prober, and the semiconductor properties were measured using a semiconductor parameter analyzer 4155C (manufactured by Agilent Technologies, Inc.). For the semiconductor properties, the drain current-drain voltage was measured by scanning the gate voltage from 10 V to −100 V at 20 V steps, and scanning the drain voltage from 10 V to −100 V. Current saturation was observed. The obtained voltage current curve indicated that the element is a p type semiconductor. The calculated carrier mobility is shown in Table 7.

Comparative Example 1

Instead of the compound according to the present embodiment used in Example 49, DNTT (Ref-01), 3,10-DM-DNTT (Ref-02; a compound wherein R$^1$ in (1) was a methyl group), and 2,9-DM-DNTT (Ref-03; a compound wherein R$^2$ in (1) was a methyl group) were used, and TC type field effect transistors were obtained by the same operation as that in Example 49. The compounds used and the results are shown in Table 7.

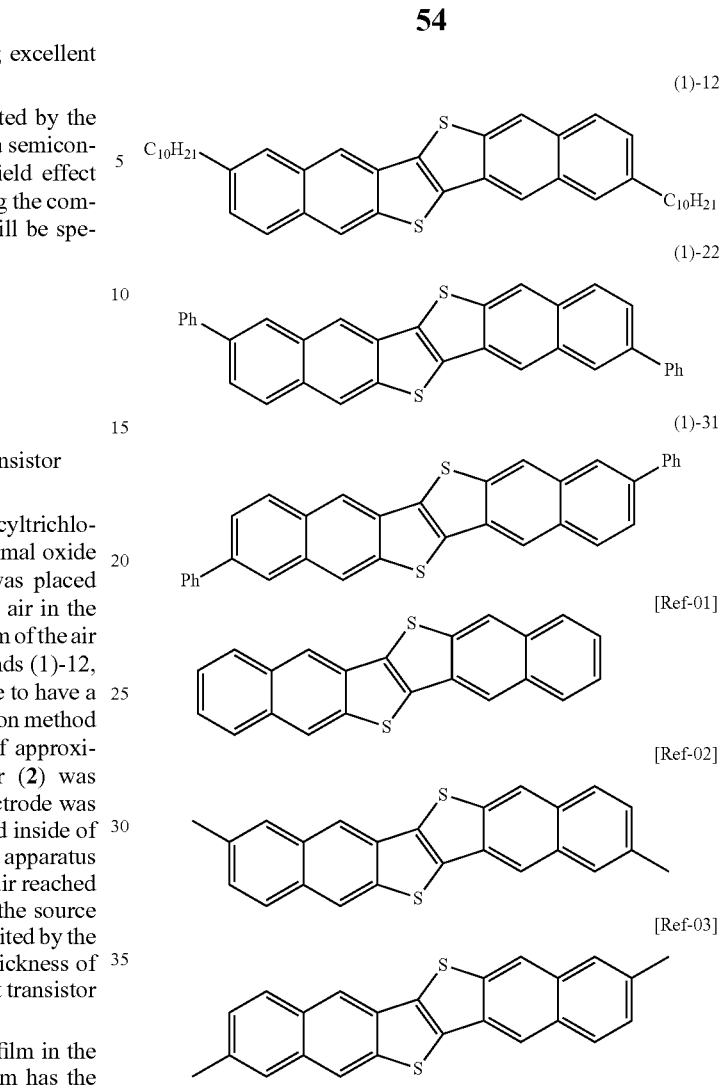

TABLE 7

| Compound No. | R$^1$ | R$^2$ | Mobility (cm$^2$/Vs) |
|---|---|---|---|
| (1)-12 | n-C$_{10}$H$_{21}$ | | 8.0 |
| (1)-22 | Ph | | 3.4 |
| (1)-31 | | Ph | 3.9 |
| Ref-01 | | | 3.0 |
| Ref-02 | Me | | 0.2 |
| Ref-03 | | Me | 0.2 |

Ref-02 and Ref-03, that is, the DNTT having a short alkyl chain exhibited only the properties not more than those of the DNTT scaffold (Ref-01). In the case where the compound (1) of the present invention was used to create a field effect transistor, however, the properties of the field effect transistor were extremely high as a field effect transistor formed by the deposition method using a standard organic substance as the semiconductor. The mobility of the field effect transistor was equal to that of the field effect transistor formed using a single crystal that is hardly realized in industrial scale. Such extremely high mobility was obtained by the vacuum evaporation method industrially suitable. The field effect transistor of this application having high performance extremely increased the industrial value, for example, extended the range of usable applications.

Example 50

Using the compounds of this application synthesized in Examples 38 to 48, and the compound Ref-01 in Comparative Example 1, and the compound (2)-64, TC type field effect transistors were created by the same operation as that in Example 49 except that a substrate treated with HMDS-SAM was used, the substrate temperature during deposition was 25° C. and 100° C., L=50 μm, and W=2000 μm. The semiconductor properties of the obtained transistors were measured according to Example 49. The calculated carrier mobility is shown in Table 8. These results show that the compound of this application exhibits high performance as a p type semiconductor material.

TABLE 8

| Compound No. | $R^1$ | $R^2$ | Mobility (cm$^2$/Vs) |
|---|---|---|---|
| (1)-04 | n-Bu | | 3.16 |
| (1)-08 | n-C$_6$H$_{13}$ | | 2.96 |
| (1)-10 | n-C$_8$H$_{17}$ | | 3.22 |
| (1)-12 | n-C$_{10}$H$_{21}$ | | 3.98 |
| (1)-14 | n-C$_{12}$H$_{25}$ | | 3.78 |
| (1)-22 | Ph | | 4.04 |
| (1)-23 | 4-Tolyl | | 1.78 |
| (1)-31 | | Ph | 2.06 |
| (1)-32 | | 4-Tolyl | 2.09 |
| (1)-33 | | PhPh | 1.86* |
| Ref-01 | | | 1.22 |

Example 51

Using the compound (1)-22 synthesized in Example 39 and the compound (2)-64 synthesized in Synthesis Example 14, TC type field effect transistors were created by the same operation as that in Example 49 except that a substrate treated with HMDS-SAM was used, the substrate temperature during deposition was 100° C., L=40 μm, and W=1500 μm. The obtained field effect transistors were subjected to a heat resistance test. The measurement results are shown in Table 9. Comparing the initial properties (μ=1.66 cm$^2$/Vs, Vth=−14 V, Ion/off~10$^9$), the mobility was approximately 1.6 cm$^2$/Vs even after annealing at 100° C. and 150° C., and the values of these properties were kept approximately equal to the initial values thereof. The properties were improved, for example, Vth was shifted to a low potential side. In contrast, the mobility of the compound (2)-64 reduced by half at approximately 120° C. From these experiments, it was found out that the compound having an aryl group to be substituted such as the compound (1)-22 of the present invention has high thermal stability, and can attain a transistor that can stand industrial processes.

TABLE 9

| | Compound No. | | | | | |
|---|---|---|---|---|---|---|
| | (1)-22 | | | (2)-64 | | |
| | μ/cm$^2$/Vs | V$_{th}$/V | I$_{on}$/I$_{off}$ | μ/cm$^2$/Vs | V$_{th}$/V | I$_{on}$/I$_{off}$ |
| Not annealed | 1.66 | −14.0 | 1.0 × 10$^9$ | 1.96 | 0.2 | 1.0 × 10$^9$ |
| Annealed (100° C.) | 1.59 | −8.8 | 1.0 × 10$^9$ | 1.52 | −1.0 | 1.0 × 10$^9$ |
| Annealed (150° C.) | 1.62 | −7.0 | 1.0 × 10$^9$ | 0.77 | 0.8 | 1.0 × 10$^9$ |

Example 52

Figure 4:
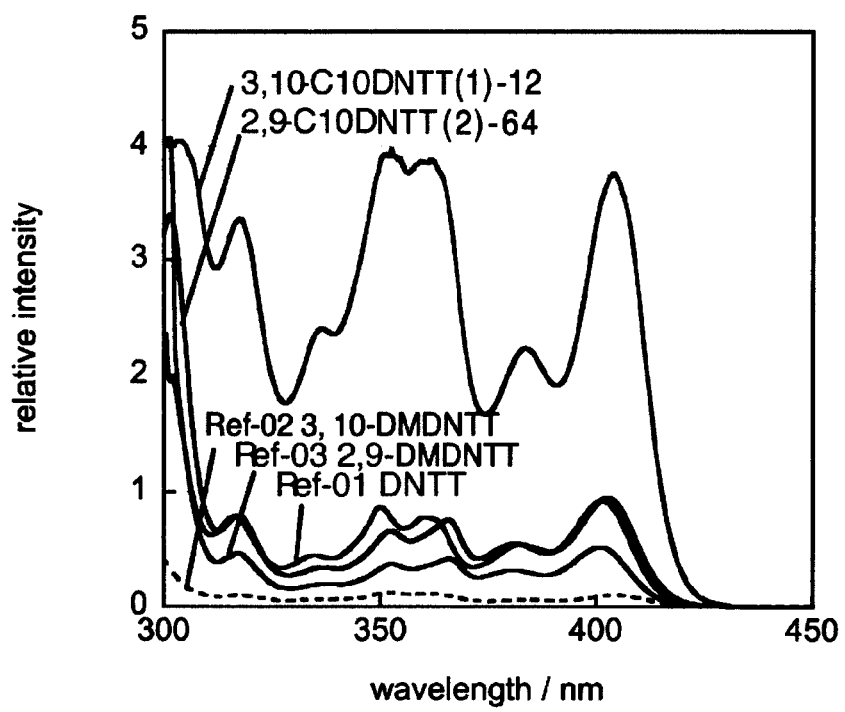
FIG. 4 shows light absorption spectrums of chloroform solutions of DNTTs.

Absorption spectrums of saturated solutions obtained by dissolving the DNTT having a C10 alkyl group at 2,9-positions (compound (2)-64), the DNTT having a C10 alkyl group at 3,10-positions (compound (1)-12), and the like in chloroform are shown in FIG. 4. In the case of the DNTT having a C10 long-chain alkyl group, from the results, the relative intensity of the longest absorption wavelength according to the substitution position was 3.9 in 3,10-C10-DNTT (compound (1)-12) wherein the relative intensity was 1 in 2,9-C10-DNTT (compound (2)-64). It was found out that 3,10-C10-DNTT (compound (1)-12) exhibited high solubility because of the difference in the substitution position. The solubility at 60° C. in toluene was 45 mg/L in 2,9-C10-DNTT (compound (2)-64) and >260 mg/L in 3,10-C10-DNTT (compound (1)-09). It was clearly found out that the solubility of 3,10-C10-DNTT (compound (1)-12) was also high in a heating state (Table 10).

TABLE 10

| Compound No. | $R^1$ | $R^2$ | Solubility ratio Chloroform | Solubility 60° C. toluene |
|---|---|---|---|---|
| (1)-12 | n-C$_{10}$H$_{21}$ | | 3.8 | >260 mg/L |
| (2)-64 | | n-C$_{10}$H$_{21}$ | 1 | 45 mg/L |

From FIG. 4 wherein the solubility of the DNTT was 1, the solubility ratio of the DNTT having a short alkyl chain Ref-02 was 0.1 and the solubility ratio of the DNTT having a short alkyl chain Ref-03 was 0.5. Ref-02 and Ref-03 do not dissolve in most of solvents as the DNTT scaffold (Ref-01, the compound does not dissolve in most of solvents). It was found out that the compound (1)-12 having an alkyl substituent at 3,10-positions has higher solvent solubility than that of the compound (2)-64 having an alkyl substituent at 2,9-positions. It was also found out that considering the solution process, the compound having an alkyl substituent at 3,10-positions has more excellent properties. Namely, use of such high solubility enables production of a field effect transistor by creating a practical ink for creating a semiconductor device or applying the ink created.

Example 53

An n-doped silicon wafer subjected to an octadecyltrichlorosilane treatment and having a 300 nm SiO$_2$ thermal oxide film (surface resistance of 0.02 Ω·cm or less) was placed inside of a vacuum deposition apparatus, and the air in the apparatus was discharged until the degree of vacuum reached 5.0×10$^{-3}$ Pa or less. Each of the compounds (1)-12 and 2-(64) was deposited onto an electrode to have a thickness of 50 nm by the resistance heating deposition method under the condition of the substrate temperature of approximately 100° C. Thereby, a semiconductor layer (2) was formed. Next, a shadow mask for creating an electrode (channel width of 1500 μm) having a channel length L of 40 μm or 190 μm was attached to this substrate. The substrate was placed inside of the vacuum deposition apparatus, and the air in the apparatus was discharged until the degree of vacuum reached 1.0×10$^{-4}$ Pa or less. The gold electrodes, namely, the source electrode (1) and the drain electrode (3) were deposited by the resistance heating deposition method to have a thickness of 40 nm. Thereby, a TC (top contact) type field effect transistor of the present invention was obtained. The results obtained by measuring these semiconductor properties in the same manner as in Example 49 are shown in Table 11. The results show that in the compound (1)-12 having a substituent at 3,10-positions, the mobility hardly reduced at L=40 μm and L=190 μm, and channel length dependency was small. Meanwhile, the compound (2)-64 having a substituent at 2,9-positions attained a transistor having the mobility 6.1 cm²/Vs at L=190 μm, but the channel length dependency was remarkable. At L=40 μm, the mobility reduced by half or less.

TABLE 11

| Compound No. | R¹ | R² | L (cm) | (cm²/Vs) | Vth (V) | Ion/off |
|---|---|---|---|---|---|---|
| (2)-64 | | n-C$_{10}$H$_{21}$ | 40 | 3.7 | −10 | 10$^8$ |
| (2)-64 | | n-C$_{10}$H$_{21}$ | 190 | 6.1 | −5 | 10$^9$ |
| (1)-12 | n-C$_{10}$H$_{21}$ | | 40 | 3.15 | −19 | 10$^9$ |
| (1)-12 | n-C$_{10}$H$_{21}$ | | 190 | 3.56 | −17 | 10$^8$ |

It is assumed that a shorter channel is demanded in creation of devices, and reduction in properties such as mobility needs to be prevented in such cases. The results indicated that use of the DNTT having a substituent at 3,10 positions and having small channel length dependency enables production of a field effect transistor that can stand practical use in devices.

As above, it revealed that the compound (DNTT having an alkyl substituent at 3,10-positions) wherein R¹ in the compound (1) of the present invention each independently represents a C2-C16 alkyl group and R² is a hydrogen atom has improved solubility compared to that of the DNTT having an alkyl substituent at 2,9-positions. It turned out that when at least one of R¹ and R² is an aryl group, heat resistance significantly improves compared to the DNTT in which the at least one of R¹ and R² is not substituted, and the properties as the organic semiconductor significantly improve. Thus, the present invention can attain an organic field effect transistor having excellent properties, and create an element exhibiting carrier mobility suitable for practical use. It revealed that the present invention has high industrial values such as adaptability to various device creation processes and extension of usable processes and applications areas.

REFERENCE SIGNS LIST

Same referential numerals are given to same elements in FIG. 1 to FIG. 3.
1 Source electrode
2 Semiconductor layer
3 Drain electrode
4 Insulator layer
5 Gate electrode
6 Substrate
7 Protective layer

The invention claimed is:

1. A heterocyclic compound represented by the following formula (1):

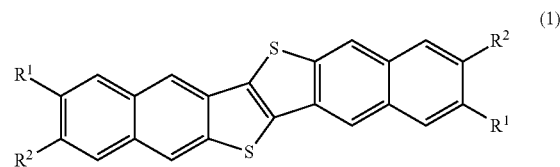

(1)

(wherein R¹ and R² each represent one of a hydrogen atom, a C2-C16 alkyl group, and an aryl group; when R¹ each independently represents a C2-C16 alkyl group or an aryl group, R² each represents a hydrogen atom or R² each independently represents an aryl group; and when R¹ represents a hydrogen atom, R² each independently represents an aryl group).

2. The heterocyclic compound according to claim 1, wherein in the formula (1), R¹ each independently is a linear C5-C12 alkyl group, and R² each is a hydrogen atom.

3. The heterocyclic compound according to claim 1, wherein in the formula (1), R¹ each independently is an aryl group having one of a phenyl structure, a naphthyl structure, and a biphenyl structure, and R² each is a hydrogen atom.

4. The heterocyclic compound according to claim 3, wherein in the formula (1), R¹ each independently is an aryl group selected from the group consisting of a phenyl group, a 4-alkylphenyl group, a 1-naphthyl group, and a biphenyl group, and R² is a hydrogen atom.

5. The heterocyclic compound according to claim 1, wherein in the formula (1), R¹ is a hydrogen atom, and R² each independently is an aryl group having one of a phenyl structure, a naphthyl structure, and a biphenyl structure.

6. The heterocyclic compound according to claim 5, wherein in the formula (1), R¹ each is a hydrogen atom, and R² each independently is an aryl group selected from the group consisting of a phenyl group, a 4-alkylphenyl group, a 1-naphthyl group, and a biphenyl group.

7. An organic semiconductor material comprising one or two or more heterocyclic compounds represented by the formula (1) according to claim 1.

8. An ink for creating a semiconductor device, comprising one or two or more heterocyclic compounds represented by the formula (1) according to claim 1.

9. A method for producing an organic thin film, which comprises applying the ink according to claim 8.

10. A method for producing a field effect transistor, comprising the step of forming an organic thin film on a substrate by the method according to claim 9.

11. An organic thin film comprising one or two or more heterocyclic compounds represented by the formula (1) according to claim 1.

12. A field effect transistor comprising an organic thin film according to claim 11.

13. The field effect transistor according to claim 12, wherein the field effect transistor is a bottom contact type.

14. The field effect transistor according to claim 12, wherein the field effect transistor is a top contact type.

15. A method for producing an organic thin film, wherein the organic thin film according to claim 11 is formed by a deposition method.

16. A method for producing a field effect transistor, comprising the step of forming an organic thin film on a substrate by the method according to claim 15.

17. A method for producing an intermediate compound represented by a formula (4) in production of a heterocyclic compound represented by a formula (2), the method comprising reacting a compound represented by a formula (3) with dimethyl disulfide:

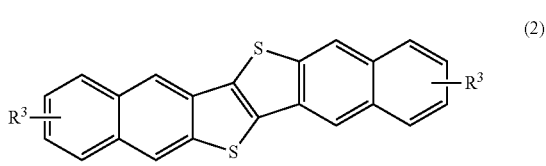

(2)

(wherein R³ represents a substituent);

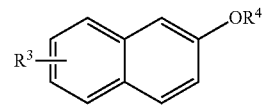
(3)
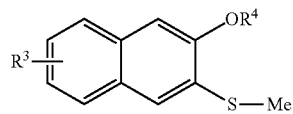
(4)
(wherein R³ and R⁴ represent a substituent).
18. A method for producing an intermediate compound represented by a formula (6) in production of a heterocyclic compound represented by a formula (2), the method comprising reacting a compound represented by a formula (4) with a tin compound represented by a formula (5):
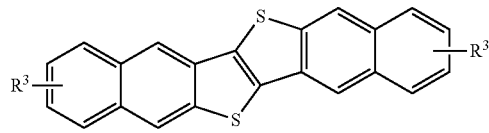
(2)
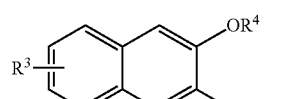
(4)
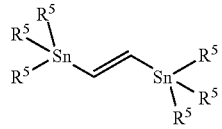
(5)
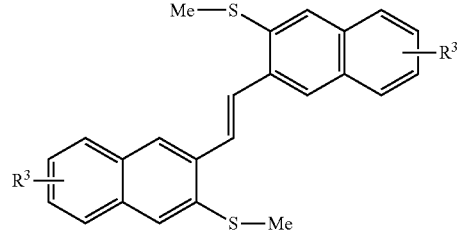
(6)
(wherein R³, R⁴, and R⁵ represent a substituent).
* * * * *